(12) United States Patent
Waisman et al.

(10) Patent No.: US 7,626,008 B2
(45) Date of Patent: Dec. 1, 2009

(54) ANTI-ANGIOGENIC POLYPEPTIDES

(76) Inventors: David M. Waisman, 136 NW. Silvergrove Manor, Calgary, AB (CA) T3B 5K6; Geeth Kassam, 6363 Christie Ave, #412, Emeryville, CA (US) 94608; Mijung Kwon, 1005-3031 Hospital Drive NW., Calgary, AB (CA) T2N 2T8

( * ) Notice: Subject to any disclaimer, the term of this patent is extended or adjusted under 35 U.S.C. 154(b) by 0 days.

(21) Appl. No.: 12/183,896

(22) Filed: Jul. 31, 2008

(65) Prior Publication Data
US 2009/0061510 A1    Mar. 5, 2009

Related U.S. Application Data

(62) Division of application No. 10/415,012, filed as application No. PCT/US01/44515 on Nov. 28, 2001, now Pat. No. 7,420,036.

(60) Provisional application No. 60/253,725, filed on Nov. 29, 2000.

(51) Int. Cl.
*C12N 15/11* (2006.01)
(52) U.S. Cl. .................................. 536/23.1
(58) Field of Classification Search ............... None
See application file for complete search history.

(56) References Cited

U.S. PATENT DOCUMENTS 4,462,980 A    7/1984    Diedrichsen et al.

FOREIGN PATENT DOCUMENTS

| WO | WO 99/16889 | 4/1999 |
|---|---|---|
| WO | WO 02/44328 | 6/2002 |

OTHER PUBLICATIONS

Overbeek (1994, "Factors affecting transgenic animal production," Transgenic animal technology, pp. 96-98).*
Wall, 1996 Theriogenology, vol. 45, pp. 57-68.*
Houdebine, 1994, J. Biotech. vol. 34, pp. 269-287.*
Cameron, 1997, Molec. Biol. 7, pp. 253-265.*
Niemann, 1997, Transg. Res. 7, pp. 73-75.*
Mullins 1993, Hypertension, vol. 22, pp. 630-633.*
Mullins 1990, Nature, vol. 344, 541-544.*
Hammer 1990, Cell, vol. 63, 1099-1112.*
Mullins, 1989, EMBO J., vol. 8, pp. 4065-4072.*
Taurog, 1988, Jour. Immunol., vol. 141, pp. 4020-4023.*
Mullins 1996, J. Clin. Invest. vol. 98, pp. S37-S40.*
Menhart, et al., "Construction, expression, and purification of recombinant kringle 1 of human plasminogen and analysis of its interaction with w-amino acid," Biochemistry 30:1948-1957, 1991.
Cao et al., "Kringle domains of human angiostain. Characterization of the anti-prolferative activity on endothelial cells." J Biol Chem., 1996, vol. 271, No. 46, pp. 29461-29467.
Heidtmann et al., "Generation of angiostain-like fragments from plasminogen by prostate-specific antigen." Br J Cancer, 1999, vol. 81, No. 8, pp. 1269-1273.

Macdonald et al., "The tumor-supressing activity of angiostain protein resides within kringles 1 to 3." Biochem Biophys Res Commun., 1999, vol. 254, No. 2, pp. 469-477.
Soff, "Angiostain and angiostatin-related proteins." Cancer Metastases Rev., 2000, vol. 19, No. (1-2), pp. 97-107.
Ballagamba et al, "Tyrosine phosphorylation of annexin II tetramer is stimulated by membrane binding." J Biol Chem., 1997, vol. 272, No. 6, pp. 3195-3199.
Brooks et al., "Ca2+-dependent and phospholipid-independent binding of annexin 2 and annexin 5." Biochem J., 2002, vol. 367, Pt 3, pp. 895-900.
Caplan et al, "Regulation of annexin A2 by reversible glutathionylation." J Biol Chem., 2004, vol. 279, No. 9, pp. 7740-7750.
Choi et al., "Annexin II tetramer inhibits plasmin-dependent fibrinolysis." Biochemistry, 1998, vol. 37, No. 2, pp. 648-655.
Choi et al., "Regulation of plasmin-dependent fibrin clot lysis by annexin II heterotetramer." J Biol Chem., 2001, vol. 276, No. 27, pp. 25212-25221.
Choi et al., "p11 regulates extracellular plasmin production and invasiveness of HT1080 fibrosarcoma cells." FASEB J., 2003, vol. 17, No. 2, pp. 235-246.
Falcone et al., "Macrophage formation of angiostatin during inflammation. A byproduct of the activation of plasminogen." J Biol Chem., 1998, vol. 273, No. 47, pp. 31480-31485.
Filipenko et al., "Characterization of the Ca2+-binding sites of annexin II tetramer." J Biol Chem., 2000, vol. 275, No. 49, pp. 38877-38884.
Filipenko et al., "The C terminus of annexin II mediates binding to F-actin." J Biol Chem., 2001, vol. 276, No. 7, pp. 5310-5315.
Filipenko et al., "Annexin A2 is a novel RNA-binding protein." J Biol Chem., 2004, vol. 279, No. 10, pp. 8723-8731.
Fitzpatrick et al., "Fucoidan-dependent conformational changes in annexin II tetramer." Biochemistry, 2000, vol. 39, No. 9, pp. 2140-2148.
Fitzpatrick et al., "Regulation of plasmin activity by annexin II tetramer." Biochemistry, 2000, vol. 39, No. 5, pp. 1021-1028.
Fogg et al., "The p11 subunit of annexin II heterotetramer is regulated by basic carboxypeptidase." Biochemistry, 2002, vol. 41, No. 15, pp. 4953-4961.
Gately et al., "The mechanism of cancer-mediated conversion of plasminogen to the angiogenesis inhibitor angiostatin." Proc Natl Acad Sci U S A, 1997, vol. 94, No. 20, pp. 10868-10872.
Johnsson et al., "Alkylation of cysteine 82 of p11 abolishes the complex formation with the tyrosine-protein kinase substrate p36 (annexin 2, calpactin 1, lipocortin 2)." J Biol Chem., 1990, vol. 265, No. 24, pp. 14464-14468.
Kang et al., "Characterization of human recombinant annexin II tetramer purified from bacteria: role of N-terminal acetylation." Biochemistry, 1997, vol. 36, No. 8, pp. 2041-2050.
Kassam et al. "Characterization of the heparin binding properties of annexin II tetramer." J Biol Chem., 1997, vol. 272, No. 24, pp. 15093-15100.
Kassam et al., "The role of annexin II tetramer in the activation of plasminogen." J Biol Chem., 1998, vol. 273, No. 8, pp. 4790-4799.

(Continued)

*Primary Examiner*—Christopher H Yaen

(57) ABSTRACT

Anti-angiogenic polypeptides $A_{61}$ or p22 are disclosed. Also disclosed are methods of making the polypeptides and methods of treating subjects having angiogenic diseases or conditions.

3 Claims, 32 Drawing Sheets

OTHER PUBLICATIONS

Kassam et al., "The p11 subunit of the annexin II tetramer plays a key role in the stimulation of t-PA-dependent plasminogen activation." Biochemistry, 1998, vol. 37, No. 48, pp. 16958-16966.

Kwon et al., "Identification of annexin II heterotetramer as a plasmin reductase." J Biol Chem., 2002, vol. 277, No. 13, pp. 10903-10911.

Lay et al., "Phosphoglycerate kinase acts in tumour angiogenesis as a disulphide reductase." Nature, 2000, vol. 408, No. 6814, pp. 869-873.

MacLeod et al., "Phospholipid-associated annexin A2-S100A10 heterotetramer and its subunits: characterization of the interaction with tissue plasminogen activator, plasminogen, and plasmin." J Biol Chem., 2003, vol. 278, No. 28, pp. 25577-25584.

Stathakis et al., "Generation of angiostatin by reduction and proteolysis of plasmin. Catalysis by a plasmin reductase secreted by cultured cells." J Biol Chem., 1997, vol. 272, No. 33, pp. 20641-20645.

Stathakis et al., "Angiostatin formation involves disulfide bond reduction and proteolysis in kringle 5 of plasmin." J Biol Chem., 1999, vol. 274, No. 13, pp. 8910-8916.

Teratani et al., "Induced transcriptional expression of calcium-binding protein S100A1 and S100A10 genes in human renal cell carcinoma." Cancer Lett., 2002, vol. 175, No. 1, pp. 71-77.

Yao et al., "Dexamethasone alters arachidonate release from human epithelial cells by induction of p11 protein synthesis and inhibition of phospholipase A2 activity." J Biol Chem., 1999, vol. 274, No. 24, pp. 17202-17208.

Zhang et al., "RNA interference-mediated silencing of the S100A10 gene attenuates plasmin generation and invasiveness of Colo 222 colorectal cancer cells." J Biol Chem., 2004, vol. 279, No. 3, pp. 2053-2062.

International Search Report for PCT/US01/44515, dated Apr. 13, 2007, 4 pages.

* cited by examiner

```
  1  MEHKEVVLLL  LLFLKSGQGE  PLDDYVNTQG  ASLFSVTKKQ  LGAGSIEECA  AKCEEDEEFT   60
 61  CRAFQYHSKE  QQCVIMAENR  KSSIIIRMRD  VVLFEKKVYL  SECKTGNGKN  YRGTMSKTKN  120
121  GITCQKWSST  SPHRPRFSPA  THPSEGLEEN  YCRNPDNDPQ  GPWCYTTDPE  KRYDYCDILE  180
181  CEEECMHCSG  ENYDGKISKT  MSGLECQAWD  SQSPHAHGYI  PSKFPNKNLK  KNYCRNPDRE  240
241  LRPWCFTTDP  NKRWELCDIP  RCTTPPPSSG  PTYQCLKGTG  ENYRGNVAVT  VSGHTCQHWS  300
301  AQTPHTHNRT  PENFPCKNLD  ENYCRNPDGK  RAPWCHTTNS  QVRWEYCKIP  SCDSSPVSTE  360
361  QLAPTAPPEL  TPVVQDCYHG  DGQSYRGTSS  TTTTGKKCQS  WSSMTPHRHQ  KTPENYPNAG  420
421  LTMNYCRNPD  ADKGPWCFTT  DPSVRWEYCN  LKKCSGTEAS  VVAPPPVVLL  PDVETPSEED  480
481  CMFGNGKGYR  GKRATTVTGT  PCQDWAAQEP  HRHSIFTPET  NPRAGLEKNY  CRNPDGDVGG  540
541  PWCYTTNPRK  LYDYCDVPQC  AAPSFDCGKP  QVEPKKCPGR  VVGGCVAHPH  SWPWQVSLRT  600
601  RFGMHFCGGT  LISPEWVLTA  AHCLEKSPRP  SSYKVILGAH  QEVNLEPHVQ  EIEVSRLFLE  660
661  PTRKDIALLK  LSSPAVITDK  VIPACLPSPN  YVVADRTECF  ITGWGETQGT  FGAGLLKEAQ  720
721  LPVIENKVCN  RYEFLNGRVQ  STELCAGHLA  GGTDSCQGDS  GGPLVCFEKD  KYILQGVTSW  780
781  GLGCARPNKP  GVYVRVSRFV  TWIEGVMRNN
```

FIGURE 1

```
aacaacatcc tgggattggg acccactttc tgggcactgc tggccagtcc caaaatggaa   60
cataaggaag tggttcttct acttctttta tttctgaaat caggtcaagg agagcctctg  120
gatgactatg tgaataccca gggggcttca ctgttcagtg tcactaagaa gcagctggga  180
gcaggaagta tagaagaatg tgcagcaaaa tgtgaggagg acgaagaatt cacctgcagg  240
gcattccaat atcacagtaa agagcaacaa tgtgtgataa tggctgaaaa caggaagtcc  300
tccataatca ttaggatgag agatgtagtt ttatttgaaa agaaagtgta tctctcagag  360
tgcaagactg ggaatggaaa gaactacaga gggacgatgt ccaaaacaaa aaatggcatc  420
acctgtcaaa aatggagttc cacttctccc cacagaccta gattctcacc tgctacacac  480
ccctcagagg gactggagga gaactactgc aggaatccag acaacgatcc gcagggcccc  540
tggtgctata ctactgatcc agaaaagaga tatgactact gcgacattct tgagtgtgaa  600
gaggaatgta tgcattgcag tggagaaaac tatgacggca aaatttccaa gaccatgtct  660
ggactggaat gccaggcctg ggactctcag agcccacacg ctcatggata cattccttcc  720
aaatttccaa acaagaacct gaagaagaat tactgtcgta accccgatag ggagctgcgg  780
ccttggtgtt tcaccaccga ccccaacaag cgctgggaac tttgcgacat ccccgctgc   840
acaacacctc caccatcttc tggtcccacc taccagtgtc tgaagggaac aggtgaaaac  900
tatcgcggga atgtggctgt taccgtttcc gggcacacct gtcagcactg gagtgcacag  960
accoctcaca cacataacag gacaccagaa aacttcccct gcaaaaattt ggatgaaaac 1020
tactgccgca atcctgacgg aaaaagggcc ccatggtgcc atacaaccaa cagccaagtg 1080
cggtgggagt actgtaagat accgtcctgt gactcctccc cagtatccac ggaacaattg 1140
gctcccacag caccacctga gctaacccct gtggtccagg actgctacca tggtgatgga 1200
cagagctacc gaggcacatc ctccaccacc accacaggaa agaagtgtca gtcttggtca 1260
tctatgacac cacaccggca ccagaagacc ccagaaaact acccaaatgc tggcctgaca 1320
atgaactact gcaggaatcc agatgccgat aaaggcccct ggtgttttac cacagacccc 1380
agcgtcaggt gggagtactg caacctgaaa aaatgctcag gaacagaagc gagtgttgta 1440
gcacctccgc ctgttgtcct gcttccagat gtagagactc cttccgaaga agactgtatg 1500
tttgggaatg ggaaaggata ccgaggcaag agggcgacca ctgttactgg gacgccatgc 1560
caggactggg ctgccagga gccccataga cacagcattt tcactccaga gacaaatcca 1620
cgggcgggtc tggaaaaaaa ttactgccgt aaccctgatg gtgatgtagg tggtccctgg 1680
tgctacacga caaatccaag aaaactttac gactactgtg atgtccctca gtgtgcggcc 1740
ccttcatttg attgtgggaa gcctcaagtg gagccgaaga aatgtcctgg aagggttgtg 1800
gggggtgtg tggcccaccc acattcctgg ccctggcaag tcagtcttag aacaaggttt 1860
ggaatgcact tctgtggagg caccttgata tccccagagt gggtgttgac tgctgcccac 1920
tgcttggaga agtccccaag gccttcatcc tacaaggtca tcctgggtgc acaccaagaa 1980
gtgaatctcg aaccgcatgt tcaggaaata gaagtgtcta ggctgttctt ggagcccaca 2040
cgaaaagata ttgccttgct aaagctaagc agtcctgccg tcatcactga caaagtaatc 2100
ccagcttgtc tgccatcccc aaattatgtg gtcgctgacc ggaccgaatg tttcatcact 2160
ggctggggag aaacccaagg tactttgga gctggccttc tcaaggaagc ccagctccct 2220
gtgattgaga ataaagtgtg caatcgctat gagtttctga atgaagagt ccaatccacc 2280
gaactctgtg ctgggcattt ggccggaggc actgacagtt gccagggtga cagtggaggt 2340
cctctggttt gcttcgagaa ggacaaatac attttacaag gagtcacttc ttggggtctt 2400
ggctgtgcac gccccaataa gcctggtgtc tatgttcgtg tttcaaggtt tgttacttgg 2460
attgagggag tgatgagaaa taattaattg gacgggagac agagtgacgc actgactcac 2520
ctagaggctg gacgtgggt agggatttag catgctggaa ataactggca gtaatcaaac 2580
gaagacactg tccccagcta ccagctacgc caaacctcgg cattttttgt gttatttttct 2640
gactgctgga ttctgtagta aggtgacata gctatgacat ttgttaaaaa taaactctgt 2700
acttaacttt gatttgagta aattttggtt tt                                2732
```

FIGURE 2

SEQUENCE LISTING

```
<160> NUMBER OF SEQ ID NOS: 8

<210> SEQ ID NO 1
<211> LENGTH: 391
<212> TYPE: PRT
<213> ORGANISM: Homo sapiens

<400> SEQUENCE: 1

Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
                100                 105                 110

Trp Asp Ser Gln Ser Pro His Ala His Gly Tyr Ile Pro Ser Lys Phe
            115                 120                 125

Pro Asn Lys Asn Leu Lys Lys Asn Tyr Cys Arg Asn Pro Asp Arg Glu
        130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Pro Ser Ser Gly Pro Thr
                165                 170                 175
```

```
Tyr Gln Cys Leu Lys Gly Thr Gly Glu Asn Tyr Arg Gly Asn Val Ala
                180                 185                 190

Val Thr Val Ser Gly His Thr Cys Gln His Trp Ser Ala Gln Thr Pro
                195                 200                 205

His Thr His Asn Arg Thr Pro Glu Asn Phe Pro Cys Lys Asn Leu Asp
            210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
                260                 265                 270

Glu Leu Thr Pro Val Val Gln Asp Cys Tyr His Gly Asp Gly Gln Ser
            275                 280                 285

Tyr Arg Gly Thr Ser Ser Thr Thr Thr Gly Lys Lys Cys Gln Ser
            290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
                340                 345                 350

Cys Asn Leu Lys Lys Cys Ser Gly Thr Glu Ala Ser Val Val Ala Pro
                355                 360                 365

Pro Pro Val Val Leu Leu Pro Asp Val Glu Thr Pro Ser Glu Glu Asp
            370                 375                 380

Cys Met Phe Gly Asn Gly Lys
385                 390

<210> SEQ ID NO 2
<211> LENGTH: 394
<212> TYPE: PRT
<213> ORGANISM: Homo sapiens

<400> SEQUENCE: 2

Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
                20                  25                  30

Ser Thr Ser Pro His Arg Pro Arg Phe Ser Pro Ala Thr His Pro Ser
            35                  40                  45

Glu Gly Leu Glu Glu Asn Tyr Cys Arg Asn Pro Asp Asn Asp Pro Gln
        50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Glu Cys Met His Cys Ser Gly Glu Asn
                85                  90                  95

Tyr Asp Gly Lys Ile Ser Lys Thr Met Ser Gly Leu Glu Cys Gln Ala
                100                 105                 110

Trp Asp Ser Gln Ser Pro His Ala His Gly Tyr Ile Pro Ser Lys Phe
            115                 120                 125

Pro Asn Lys Asn Leu Lys Lys Asn Tyr Cys Arg Asn Pro Asp Arg Glu
        130                 135                 140

Leu Arg Pro Trp Cys Phe Thr Thr Asp Pro Asn Lys Arg Trp Glu Leu
```

-continued

```
                145                 150                 155                 160
Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro Val Val Leu Leu Pro Asp Val Glu Thr Pro Ser Glu Glu Asp
    370                 375                 380

Cys Met Phe Gly Asn Gly Lys Gly Tyr Arg
385                 390

<210> SEQ ID NO 3
<211> LENGTH: 103
<212> TYPE: PRT
<213> ORGANISM: Homo sapiens

<400> SEQUENCE: 3

Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys
            100

<210> SEQ ID NO 4
<211> LENGTH: 810
```

```
<212> TYPE: PRT
<213> ORGANISM: Homo sapiens

<400> SEQUENCE: 4

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
    370                 375                 380

Tyr Arg Gly Thr Ser Ser Thr Thr Thr Gly Lys Lys Cys Gln Ser
385                 390                 395                 400
```

```
Trp Ser Ser Met Thr Pro His Arg His Gln Lys Thr Pro Glu Asn Tyr
                405                 410                 415
Pro Asn Ala Gly Leu Thr Met Asn Tyr Cys Arg Asn Pro Asp Ala Asp
            420                 425                 430
Lys Gly Pro Trp Cys Phe Thr Thr Asp Pro Ser Val Arg Trp Glu Tyr
        435                 440                 445
Cys Asn Leu Lys Lys Cys Ser Gly Thr Glu Ala Ser Val Val Ala Pro
    450                 455                 460
Pro Pro Val Val Leu Leu Pro Asp Val Glu Thr Pro Ser Glu Glu Asp
465                 470                 475                 480
Cys Met Phe Gly Asn Gly Lys Gly Tyr Arg Gly Lys Arg Ala Thr Thr
                485                 490                 495
Val Thr Gly Thr Pro Cys Gln Asp Trp Ala Ala Gln Glu Pro His Arg
            500                 505                 510
His Ser Ile Phe Thr Pro Glu Thr Asn Pro Arg Ala Gly Leu Glu Lys
        515                 520                 525
Asn Tyr Cys Arg Asn Pro Asp Gly Asp Val Gly Gly Pro Trp Cys Tyr
    530                 535                 540
Thr Thr Asn Pro Arg Lys Leu Tyr Asp Tyr Cys Asp Val Pro Gln Cys
545                 550                 555                 560
Ala Ala Pro Ser Phe Asp Cys Gly Lys Pro Gln Val Glu Pro Lys Lys
                565                 570                 575
Cys Pro Gly Arg Val Val Gly Gly Cys Val Ala His Pro His Ser Trp
            580                 585                 590
Pro Trp Gln Val Ser Leu Arg Thr Arg Phe Gly Met His Phe Cys Gly
        595                 600                 605
Gly Thr Leu Ile Ser Pro Glu Trp Val Leu Thr Ala Ala His Cys Leu
    610                 615                 620
Glu Lys Ser Pro Arg Pro Ser Ser Tyr Lys Val Ile Leu Gly Ala His
625                 630                 635                 640
Gln Glu Val Asn Leu Glu Pro His Val Gln Glu Ile Glu Val Ser Arg
                645                 650                 655
Leu Phe Leu Glu Pro Thr Arg Lys Asp Ile Ala Leu Leu Lys Leu Ser
            660                 665                 670
Ser Pro Ala Val Ile Thr Asp Lys Val Ile Pro Ala Cys Leu Pro Ser
        675                 680                 685
Pro Asn Tyr Val Val Ala Asp Arg Thr Glu Cys Phe Ile Thr Gly Trp
    690                 695                 700
Gly Glu Thr Gln Gly Thr Phe Gly Ala Gly Leu Leu Lys Glu Ala Gln
705                 710                 715                 720
Leu Pro Val Ile Glu Asn Lys Val Cys Asn Arg Tyr Glu Phe Leu Asn
                725                 730                 735
Gly Arg Val Gln Ser Thr Glu Leu Cys Ala Gly His Leu Ala Gly Gly
            740                 745                 750
Thr Asp Ser Cys Gln Gly Asp Ser Gly Gly Pro Leu Val Cys Phe Glu
        755                 760                 765
Lys Asp Lys Tyr Ile Leu Gln Gly Val Thr Ser Trp Gly Leu Gly Cys
    770                 775                 780
Ala Arg Pro Asn Lys Pro Gly Val Tyr Val Arg Val Ser Arg Phe Val
785                 790                 795                 800
Thr Trp Ile Glu Gly Val Met Arg Asn Asn
            805                 810
```

<210> SEQ ID NO 5
<211> LENGTH: 309
<212> TYPE: DNA
<213> ORGANISM: Homo sapiens

<400> SEQUENCE: 5

| | | | | | |
|---|---|---|---|---|---|
| aaagtgtatc | tctcagagtg | caagactggg | aatggaaaga | actacagagg | gacgatgtcc | 60 |
| aaaacaaaaa | atggcatcac | ctgtcaaaaa | tggagttcca | cttctcccca | cagacctaga | 120 |
| ttctcacctg | ctacacaccc | ctcagaggga | ctggaggaga | actactgcag | gaatccagac | 180 |
| aacgatccgc | aggggccctg | gtgctatact | actgatccag | aaaagagata | tgactactgc | 240 |
| gacattcttg | agtgtgaaga | ggaatgtatg | cattgcagtg | gagaaaacta | tgacggcaaa | 300 |
| atttccaag | | | | | | 309 |

<210> SEQ ID NO 6
<211> LENGTH: 1173
<212> TYPE: DNA
<213> ORGANISM: Homo sapiens

<400> SEQUENCE: 6

| | | | | | |
|---|---|---|---|---|---|
| aaagtgtatc | tctcagagtg | caagactggg | aatggaaaga | actacagagg | gacgatgtcc | 60 |
| aaaacaaaaa | atggcatcac | ctgtcaaaaa | tggagttcca | cttctcccca | cagacctaga | 120 |
| ttctcacctg | ctacacaccc | ctcagaggga | ctggaggaga | actactgcag | gaatccagac | 180 |
| aacgatccgc | aggggccctg | gtgctatact | actgatccag | aaaagagata | tgactactgc | 240 |
| gacattcttg | agtgtgaaga | ggaatgtatg | cattgcagtg | gagaaaacta | tgacggcaaa | 300 |
| atttccaaga | ccatgtctgg | actggaatgc | caggcctggg | actctcagag | cccacacgct | 360 |
| catggataca | ttccttccaa | atttccaaac | aagaacctga | agaagaatta | ctgtcgtaac | 420 |
| cccgataggg | agctgcggcc | ttggtgtttc | accaccgacc | ccaacaagcg | ctgggaactt | 480 |
| tgcgacatcc | cccgctgcac | aacacctcca | ccatcttctg | gtcccaccta | ccagtgtctg | 540 |
| aagggaacag | gtgaaaacta | tcgcgggaat | gtggctgtta | ccgtttccgg | gcacacctgt | 600 |
| cagcactgga | gtgcacagac | ccctcacaca | cataacagga | caccagaaaa | cttcccctgc | 660 |
| aaaaatttgg | atgaaaacta | ctgccgcaat | cctgacggaa | aaagggcccc | atggtgccat | 720 |
| acaaccaaca | gccaagtgcg | gtgggagtac | tgtaagatac | cgtcctgtga | ctcctcccca | 780 |
| gtatccacgg | aacaattggc | tcccacagca | ccacctgagc | taacccctgt | ggtccaggac | 840 |
| tgctaccatg | gtgatggaca | gagctaccga | ggcacatcct | ccaccaccac | cacaggaaag | 900 |
| aagtgtcagt | cttggtcatc | tatgacacca | caccggcacc | agaagacccc | agaaaactac | 960 |
| ccaaatgctg | gcctgacaat | gaactactgc | aggaatccag | atgccgataa | aggcccctgg | 1020 |
| tgttttacca | cagacccccag | cgtcaggtgg | gagtactgca | acctgaaaaa | atgctcagga | 1080 |
| acagaagcga | gtgttgtagc | acctccgcct | gttgtcctgc | ttccagatgt | agagactcct | 1140 |
| tccgaagaag | actgtatgtt | tgggaatggg | aaa | | | 1173 |

<210> SEQ ID NO 7
<211> LENGTH: 1182
<212> TYPE: DNA
<213> ORGANISM: Homo sapiens

<400> SEQUENCE: 7

| | | | | | |
|---|---|---|---|---|---|
| aaagtgtatc | tctcagagtg | caagactggg | aatggaaaga | actacagagg | gacgatgtcc | 60 |
| aaaacaaaaa | atggcatcac | ctgtcaaaaa | tggagttcca | cttctcccca | cagacctaga | 120 |

-continued

| | |
|---|---|
| ttctcacctg ctacacaccc ctcagaggga ctggaggaga actactgcag gaatccagac | 180 |
| aacgatccgc aggggccctg gtgctatact actgatccag aaaagagata tgactactgc | 240 |
| gacattcttg agtgtgaaga ggaatgtatg cattgcagtg gagaaaacta tgacggcaaa | 300 |
| atttccaaga ccatgtctgg actggaatgc aggcctggg actctcagag cccacacgct | 360 |
| catggataca ttccttccaa atttccaaac aagaacctga agaagaatta ctgtcgtaac | 420 |
| cccgataggg agctgcggcc ttggtgtttc accaccgacc caacaagcg ctgggaactt | 480 |
| tgcgacatcc cccgctgcac aacacctcca ccatcttctg gtcccaccta ccagtgtctg | 540 |
| aagggaacag gtgaaaacta cgcgggaat gtggctgtta ccgtttccgg cacacctgt | 600 |
| cagcactgga gtgcacagac ccctcacaca cataacagga caccagaaaa cttcccctgc | 660 |
| aaaaatttgg atgaaaacta ctgccgcaat cctgacggaa aagggcccc atggtgccat | 720 |
| acaaccaaca gccaagtgcg gtgggagtac tgtaagatac cgtcctgtga ctcctcccca | 780 |
| gtatccacgg aacaattggc tcccacagca ccacctgagc taaccccgt ggtccaggac | 840 |
| tgctaccatg gtgatggaca gagctaccga ggcacatcct ccaccaccac cacaggaaag | 900 |
| aagtgtcagt cttggtcatc tatgacacca caccggcacc agaagacccc agaaaactac | 960 |
| ccaaatgctg gcctgacaat gaactactgc aggaatccag atgccgataa aggcccctgg | 1020 |
| tgttttacca cagaccccag cgtcaggtgg gagtactgca acctgaaaaa atgctcagga | 1080 |
| acagaagcga gtgttgtagc acctccgcct gttgtcctgc ttccagatgt agagactcct | 1140 |
| tccgaagaag actgtatgtt tgggaatggg aaaggatacc ga | 1182 |

<210> SEQ ID NO 8
<211> LENGTH: 714
<212> TYPE: PRT
<213> ORGANISM: Homo sapiens

<400> SEQUENCE: 8

Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala

-continued

```
                180                 185                 190
Val Thr Val Ser Gly His Thr Cys Gln His Trp Ala Gln Thr Pro
            195                 200                 205

His Thr His Asn Arg Thr Pro Glu Asn Phe Pro Cys Lys Asn Leu Asp
210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
            275                 280                 285

Tyr Arg Gly Thr Ser Ser Thr Thr Thr Thr Gly Lys Lys Cys Gln Ser
            290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
            355                 360                 365

Pro Pro Val Val Leu Leu Pro Asp Val Glu Thr Pro Ser Glu Glu Asp
            370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
            405                 410                 415

His Ser Ile Phe Thr Pro Glu Thr Asn Pro Arg Ala Gly Leu Glu Lys
            420                 425                 430

Asn Tyr Cys Arg Asn Pro Asp Gly Asp Val Gly Gly Pro Trp Cys Tyr
            435                 440                 445

Thr Thr Asn Pro Arg Lys Leu Tyr Asp Tyr Cys Asp Val Pro Gln Cys
450                 455                 460

Ala Ala Pro Ser Phe Asp Cys Gly Lys Pro Gln Val Glu Pro Lys Lys
465                 470                 475                 480

Cys Pro Gly Arg Val Val Gly Gly Cys Val Ala His Pro His Ser Trp
            485                 490                 495

Pro Trp Gln Val Ser Leu Arg Thr Arg Phe Gly Met His Phe Cys Gly
            500                 505                 510

Gly Thr Leu Ile Ser Pro Glu Trp Val Leu Thr Ala Ala His Cys Leu
            515                 520                 525

Glu Lys Ser Pro Arg Pro Ser Ser Tyr Lys Val Ile Leu Gly Ala His
            530                 535                 540

Gln Glu Val Asn Leu Glu Pro His Val Gln Glu Ile Glu Val Ser Arg
545                 550                 555                 560

Leu Phe Leu Glu Pro Thr Arg Lys Asp Ile Ala Leu Leu Lys Leu Ser
                565                 570                 575

Ser Pro Ala Val Ile Thr Asp Lys Val Ile Pro Ala Cys Leu Pro Ser
            580                 585                 590

Pro Asn Tyr Val Val Ala Asp Arg Thr Glu Cys Phe Ile Thr Gly Trp
            595                 600                 605
```

-continued

```
Gly Glu Thr Gln Gly Thr Phe Gly Ala Gly Leu Leu Lys Glu Ala Gln
        610                 615                 620

Leu Pro Val Ile Glu Asn Lys Val Cys Asn Arg Tyr Glu Phe Leu Asn
625                 630                 635                 640

Gly Arg Val Gln Ser Thr Glu Leu Cys Ala Gly His Leu Ala Gly Gly
                645                 650                 655

Thr Asp Ser Cys Gln Gly Asp Ser Gly Gly Pro Leu Val Cys Phe Glu
            660                 665                 670

Lys Asp Lys Tyr Ile Leu Gln Gly Val Thr Ser Trp Gly Leu Gly Cys
        675                 680                 685

Ala Arg Pro Asn Lys Pro Gly Val Tyr Val Arg Val Ser Arg Phe Val
        690                 695                 700

Thr Trp Ile Glu Gly Val Met Arg Asn Asn
705                 710
```

ANTI-ANGIOGENIC POLYPEPTIDES

CROSS REFERENCE TO RELATED APPLICATIONS

This application is a divisional of U.S. application Ser. No. 10/415,012, filed Apr. 22, 2003, which claims the priority of PCT Application PCT/US2001/44515, filed Nov. 28, 2001, which claims the priority of U.S. provisional application No. 60/253,725, filed Nov. 29, 2000, each of which is hereby incorporated by reference in their entirety.

BACKGROUND OF THE INVENTION

1. Field of the Invention

This invention relates generally to angeogenesis and, more particularly, to anti-angeogenic polypeptides which are related to plasminogen and to methods of making and using such polypeptides.

2. Description of the Related Art

Angiogenesis, i.e. the formation of new blood vessels, involves a complex coordination of endothelial cell proliferation, migration, basement membrane degradation and neovessel organization (Ji et al., *FASEB J.* 12:1731-1738, 1998). During normal processes such as organogenesis in the embryo and wound healing in the adult, angiogenesis provides the necessary vascular support for the newly developing tissue. In pathologic conditions, however, the growth of new blood vessels can lead to advancement of disease processes including the development and progression of cancerous tumors, diabetic retinopathy, tissue and organ malformation, and cardiovascular disorders (Folkman, *Nat. Med.* 1:27-31, 1995). With respect to cancerous tumor, increasing evidence suggests that tumor growth and lethality are dependent upon angiogenesis and that angiogenesis inhibition suppresses tumor development (Folkman, *Forum (Genova)* 9:59-62, 1999; Folkman, *Adv. Cancer. Res.* 43:175-203, 1985).

A number of angiogenesis inhibitors, i.e. anti-angiogenic substances have been identified including angiostatin, thrombospondin, and glioma-derived angiogenesis inhibitory factor (Folkman, 1995 supra). Of these, angiostatin, a 38 kDa fragment of plasminogen, has been shown to have potent anti-angiogenic activity which inhibits tumor growth (O'Reilly et al., *Nat. Med.* 2:689-692, 1996; O'Reilly et al., *Cell* 79:315-328, 1994). This is in contrast to the full length plasminogen which has no anti-angiogenic activity (Id.).

Angiostatin contains the first four of plasminogen's five triple disulfide-linked loops known as kringle regions. The four kringle regions of angiostatin and the fifth kringle region found in plasminogen, but not angiostatin, have been characterized as to anti-angiogenic activity by studying the activities of various fragments of plasminogen. Kringle 5 fragments of plasminogen obtained by proteolysis of plasminogen and by recombinant techniques have been reported to exhibit potent endothelial-cell anti-proliferative activity (Cao et al., *J. Biol. Chem.* 272:22924-22928, 1997). Similarly, a recombinant kringle 1 fragment and a recombinant kringle 3 fragment have been shown to have potent anti-proliferative activity whereas a kringle 2 fragment shows much less inhibitory activity and a kringle 4 fragment exhibits markedly low inhibitory activity (Cao et al., *J. Biol. Chem.* 271:29461-29467, 1996; U.S. Pat. No. 6,024,688 to Folkman et al.). In contrast, a fragment containing kringles 2 and 3 showed only low activity, whereas a larger angiostatin fragment containing kringle regions 1-3 showed more potent anti-proliferative activity than angiostatin itself which contains kringle regions 1-5 (Id.).

Thus, it would appear that the anti-angiogenic activity of plasminogen fragments containing more than one kringle region cannot be accurately predicted based upon the activities of the individual kringle regions and, hence, the earlier studies provide no clear guidance as to whether additional fragments of plasminogen containing more than one kringle region will show anti-angiogenic activity. In addition, angiostatin itself was isolated under reducing conditions such that this substance is believe to a non-naturally occurring fragment as are the proteolytic and recombinant fragments reported in the earlier studies cited above. Such non-naturally occurring polypeptides could potentially elicit immunologic responses in a subject or other undesirable side effects which might be avoided with a naturally occurring fragment. Furthermore, the three dimensional structure of a naturally occurring fragment of plasminogen which functions as an endogenous angiogenic agent may not be accurately predicted from the three dimensional structure of the reported proteolytic or recombinant fragments in earlier reports. It would, thus, be desirable to identify and isolate new, naturally occurring polypeptide fragments of plasminogen which possess potent and efficacious anti-angiogenic activity and which have little or no potential for producing immunologic and other side effects.

BRIEF SUMMARY OF THE INVENTION

Accordingly, the inventors herein have succeeded in discovering new, naturally occurring fragments of plasminogen. One such fragment, referenced herein as $A_{61}$, has a molecular weight of approximately 61 kDa as determined by SDS-polyacrylamide gel electrophoresis conducted under reducing conditions (Kassam, G. et al., (2001) *Journal of Biological Chemistry* 276: 8924-8933). Human $A_{61}$ has 391 amino acids the sequence of which is set forth in SEQ ID NO:1. A second naturally occurring fragment which is a minor variant isoform of $A_{61}$ is formed by cells from plasminogen in small amounts with $A_{61}$. This isoform contains 394 amino acids and has the sequence as set forth in SEQ ID NO:2. This variant isoform is included within the term $A_{61}$ as used herein. A third naturally occurring fragment, referenced herein as p22, has also been identified (Kwon, M. et al., (2001) *Biochemistry* 40: 13246-13253). P22 has a molecular weight of approximately 22 kDa. Human p22 has 103 amino acids and its sequence is as set forth in SEQ ID NO:3. The full length plasminogen human sequence from which the fragments are derived is shown in FIG. 1 and in SEQ ID NO:4. $A_{61}$, its minor variant and p22 all exhibit anti-angiogenic activity inhibiting endothelial cell proliferation in vitro and in vivo, and show anti-cancer activity in vivo.

The present invention is intended to include all $A_{61}$ and p22 molecules from a variety of vertebrate species, more preferably from mammalian species and most preferably from humans. Sequences from non-human species can be readily identified from the known plasmin and plasminogen sequences of a wide variety of species. Allelic variants of $A_{61}$ and p22 are also included within the present invention.

$A_{61}$ and p22 differ from angiostatins in several respects. First, both $A_{61}$ and p22 are naturally occurring molecules found in the blood plasma of both healthy individuals and in cancer patients. Second, they are both cleavage products of plasmin autodigestion, and, therefore, amino terminals and carboxy terminals are determined by the presence of plasmin cleavage sites within the plasminogen molecule. Unlike angiostatins, human p22 extends from Lys-78 to Lys-180 of plasminogen, thereby comprising 103 contiguous amino acids of plasminogen, and human $A_{61}$ extends from Lys-78 to Lys-468, and also includes a minor species extending from Lys-78 to Arg-471, thereby comprising 391 and 394 contiguous amino acids, respectively. Thus, p22 contains the kringle 1 region plus a portion of the kringle 2 sequence of plasminogen and $A_{61}$ contains kringle regions 1-4 and a portion of kringle 5 sequence of plasminogen.

Also unlike angiostatins, these fragments can be prepared from plasmin or plasminogen in vitro in the absence of a free sulfhydryl donor or a plasmin reductase. And because of the ready availability of human plasminogen and the autoproteolytic nature of plasmin conversion to p22 and $A_{61}$, the fragments are easily prepared in milligram quantities, either in a cell-free system or by contacting the plasminogen to cells. The p22 and $A_{61}$ polypeptides are isolated from cells cultured in the presence of plasminogen using standard techniques well known in the art, such as affinity chromatography using immobilized lysine or a lysine analogue capable of binding plasmin, hydrophobic interaction chromatography, gel filtration chromatography, and ion-exchange chromatography. Affinity chromatography with other immobilized ligands, such as (but not limited to) antibodies to plasminogen kringle domains can also be used. P22 exhibiting anti-angiogenic activity is found in both flow-through and eluted fractions when immobilized lysine is used for the isolating, and is also found in flow-through fractions when hydrophobic interaction chromatography is used for the isolating, wherein octyl-Sepharose is used as the hydrophobic solid-phase matrix.

These fragments also differ by their spectral characteristics from angiostatins and other plasminogen fragments described as having anti-angiogenic activity. In particular, the differences in autofluorescence and circular dichroism spectra indicate that the kringle domain of p22 is conformationally distinct from that of recombinant kringle 1. The circular dichroism spectrum of p22 exhibits a positive band at 227.5 and a negative band at 202.7 compared to a positive band at 227.5 and a negative band at 197.4 for the kringle 1 fragment. This indicates that the three dimensional structure of p22 differs from that of the kringle 1 fragment of plasminogen.

These fragments also differ from angiostatins in terms of their biological activity. When inhibition of bovine capillary endothelial cell proliferation is used as an assay system, $A_{61}$ requires about 35 nM for 50% inhibition of cell proliferation, whereas p22 requires about 14 nM for 50% inhibition of cell proliferation. In addition, both p22 and $A_{61}$ inhibit metastatic tumor growth in vivo using a Lewis lung carcinoma cell assay in mice as a model system. In contrast to angiostatins, both p22 and $A_{61}$ are effective in inhibiting growth of lung metastatic loci at a dose of about 2.5 mg/kg/day. $A_{61}$ and p22 can, thus, be used in the treatment of cancerous tumors in humans and other mammals.

Thus, in one embodiment, the present invention is directed to isolated and purified fragments of plasminogen which are $A_{61}$ and p22 polypeptides. The fragments can be identified by virtue of their sequence alignment with human plasminogen as set forth in SEQ ID NO:4, wherein the amino terminal amino acid is Lys-78 and the carboxy terminal amino acid is Lys-180 (p22), Lys-468 ($A_{61}$), or Arg-471 ($A_{61}$ minor variant) of human plasminogen. The fragments are naturally occurring and fragments from non-human species have at least 60%, preferably, at least 75%, more preferably, at least 80%, still more preferably at least 90% and most preferably at least 95% sequence identity with plasminogen as set forth in SEQ ID NO:4.

In another embodiment, isolated $A_{61}$ and p22 polypeptides are provided which consist of 102, 391 or 394 amino acids of the amino terminal of plasmin. The plasmin can be a vertebrate plasmin, more preferably, a mammalian plasmin and, most preferably, a human plasmin. A human plasminogen has a sequence as shown in FIG. 1 and in SEQ ID NO:4. The polypeptides of this embodiment have at least 60%, preferably, at least 75%, more preferably, at least 80%, still more preferably at least 90% and most preferably at least 95% sequence identity with plasminogen as set forth in SEQ ID NO:4.

In yet another embodiment, isolated $A_{61}$ and p22 polypeptides are provided having have sequences as set forth in SEQ ID NO:1, SEQ ID NO:2, or SEQ ID NO:3, or conservatively substituted variants thereof. By conservatively substituted variant it is meant that the polypeptide has one or more conservative amino acid substitutions compared to the sequences of SEQ ID NOS:1-3. Conservative amino acid substitutions refer to the interchangeability of amino acids having similar chemical properties as a result of having similar side chains.

The present invention provides, in another embodiment, isolated $A_{61}$ and p22 polypeptides which have at least 60%, preferably, at least 75%, more preferably, at least 80%, still more preferably at least 90% and most preferably at least 95% sequence identity with $A_{61}$ or p22 sequences. The isolated polypeptides can consist of 391 contiguous amino acids having have at least 60%, preferably, at least 75%, more preferably, at least 80%, still more preferably at least 90% and most preferably at least 95% sequence identity with SEQ ID NO: 1; or the isolated polypeptides can consist of 394 contiguous amino acids having at least 60%, preferably, at least 75%, more preferably, at least 80%, still more preferably at least 90% and most preferably at least 95% sequence identity with SEQ ID NO: 2; or the isolated polypeptides can consist of 103 contiguous amino acids having at least 60%, preferably, at least 75%, more preferably, at least 80%, still more preferably at least 90% and most preferably at least 95% sequence identity with SEQ ID NO: 3.

In another embodiment, the invention also provides conjugates of an $A_{61}$ or p22 polypeptide and a cytotoxic agent in which the $A_{61}$ or p22 polypeptide provides not only an anti-angiogenic effect, but also serves to target a regions eliciting angiogenic growth such as a growing tumor. The conjugate can, in some instances, be a fusion proteins and nucleic acid molecules encoding such fusion proteins are also included as are vectors and cells transformed with such nucleic acid molecules.

In another embodiment, the invention provides an $A_{61}$ or p22 nucleic acid molecule comprising a polynucleotide sequence which encodes an isolated $A_{61}$ or p22 polypeptide. The sequence encodes an $A_{61}$ polypeptide consisting of 391 contiguous amino acids and the polynucleotide sequence contains a sequence of not more than 1173 consecutive nucleotides of a sequence encoding plasminogen. Alternatively, the sequence encodes an $A_{61}$ polypeptide consisting of 394 contiguous amino acids and the polynucleotide sequence contains a sequence of not more than 1182 consecutive nucleotides of a sequence encoding plasminogen. As still another alternative, the sequence encodes a p22 polypeptide consisting of 103 contiguous amino acids and the polynucleotide sequence contains a sequence of not more than 309 consecutive nucleotides of a sequence encoding plasminogen. The invention also provides vectors comprising the nucleic acid, and eukaryotic and prokaryotic cells comprising the vector. The cells can be mammalian cells. The mammalian cells can be, for example, human, murine, or bovine cells. The prokaryotic cells can be bacterial cells. The bacterial cells can be, for example *E. coli* cells. In addition, the vector can be, for example, a plasmid or a virus.

In another embodiment, the invention provides an $A_{61}$ or p22 nucleic acid or complement thereto consisting of 309, 1173, or 1182 nucleotides, wherein the nucleic acid has at least 90% identity with SEQ ID NO:5, SEQ ID NO:6, or SEQ ID NO:7, respectively. In an alternative embodiment, the nucleic acid of 309, 1173 or 1182 nucleotides hybridizes under high stringency conditions to SEQ ID NO:5, SEQ ID NO:6, or SEQ ID NO:7, respectively.

The invention also provides methods for preparing $A_{61}$ and/or p22 polypeptide fragments of plasminogen. $A_{61}$ and p22 can be produced by a cell-mediated method or in a cell-free method. The cell-mediated method comprises contacting a plasminogen with a vertebrate cell which upon incubation, produces the $A_{61}$ and/or p22 fragments of plasminogen by autoproteolysis. The $A_{61}$ or p22 fragments are then isolated from the mixture. Cells are preferably mammalian cells, preferably human cells such as HT1080 or HeLa cells. Another preferred cells for use in the method is a bovine capillary endothelial cell. The plasminogen can be a glu-plasminogen or a lys-plasminogen. The isolation can be by any suitable approach including affinity chromatography using immobilized lysine or an immobilized lysine analogue capable of binding plasmin to contact the plasminogen fragment. Further purification can be through other chromatography techniques, such as hydrophobic interaction chromatography and gel filtration chromatography.

In the cell-free method, first $A_{61}$ is produced by incubation of a mixture of plasminogen with plasminogen activator. $A_{61}$ is then isolated from the mixture. p22 is then produced from the $A_{61}$ upon incubation with plasmin and a reducing agent such as dithiothreitol. The p22 is isolated from the incubation mixture. Alternatively, p22 can be produced by incubating $A_{61}$ with annexin II subunit of annexin II tetramer.

The present invention also provides methods for anti-angiogenic treatment of a mammal in need thereof. The methods comprise administering an angiogenesis-inhibiting amount of a $A_{61}$ and/or p22 to the mammal. The method is applicable to any disease or condition involving unwanted angiogenesis, in particular the growth of tumors in cancer. The mammal is, preferably, a human and the $A_{61}$ and/or p22 are, preferably, human polypeptides. The $A_{61}$ and/or p22 can also be administered in combination with other agents to treat the particular disease such as, for example, other anti-cancer agents for treating cancer.

In yet another embodiment, the invention provides for a method of inhibiting the proliferation of vascular endothelial cells. The method comprises administering to the cells $A_{61}$ or p22 or a combination thereof in an amount suitable for inhibiting endothelial cell proliferation.

Among the several advantages achieved by the present invention, therefore, may be noted the provision of new anti-angiogenic agents which are useful in treating diseases involving neovascularization which is deleterious to the individual such as occurs with cancerous tumors; the provision of anti-angiogenic agents which are naturally occurring and as a result present less risk of immunologic response to an individual receiving the agent; the provision of anti-angiogenic agents which are efficacious and which present less potential for undesirable side effects by virtue of their being substances which occur naturally in the individual receiving the agent; the provision of methods for preparing the new anti-angiogenic polypeptides which are simple to perform and which achieve a high yield of the polypeptides; and the provision of new and effective methods for treating diseases involving angiogenesis based upon administration of the new compounds.

BRIEF DESCRIPTION OF THE DRAWINGS

FIG. 1 illustrates the amino acid sequence of human plasminogen precursor in which amino acids Met-1 to Gly-19 (M-1 to G-19) are the signal peptide; amino acids from Glu-20 through Asp-810 (E-20 to N-810) are glu-plasminogen; amino acids from Lys-97 through Asp-810 (K-97 to N-810) are lys-plasminogen; amino acids from Lys-97 through Lys-487 (K-97 to K487) and amino acids from Lys-97 through Arg-490 (K-97 to R-490) are the two isoforms of $A_{61}$; and amino acids from Lys-97 through Lys-199 (K-97 to K-199) are p22.

FIG. 2 illustrates the nucleic acid sequence of human plasminogen precursor in which nucleic acids 55-111 encode the signal peptide; nucleic acids 112-2484 encode the glu-plasminogen; nucleic acids 343-2484 encode the portion of glu-plasminogen forming lys-plasminogen; nucleic acids 343-1515 and nucleic acids 343-1524 encode the portion of glu-plasminogen or lys-plasminogen forming the two $A_{61}$ isoforms; and nucleic acids 343-651 encode the portion of glu-plasminogen or lys-plasminogen forming p22.

DETAILED DESCRIPTION OF THE INVENTION

Figure 3A:
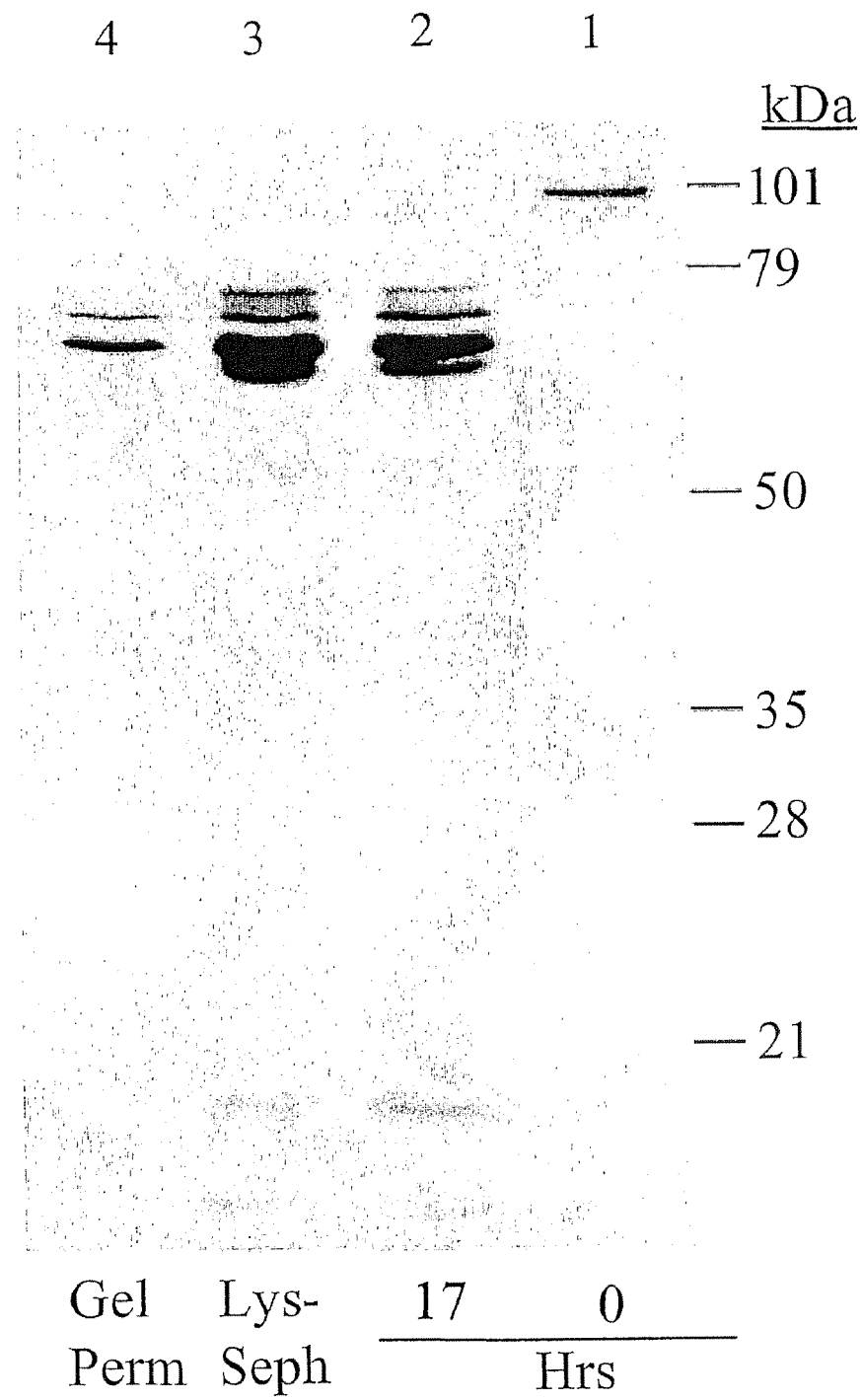
FIG. 3 illustrates the generation and isolation of $A_{61}$ produced in a cell-free system as analyzed in reduced SDS-PAGE with Coomassie Blue staining (A), in non-reduced SDS-PAGE with Coomassie Blue staining (B), and by Western blotting using a monoclonal antibody against human plasminogen kringles 1-3 as the primary antibody (C).

In accordance with the present invention, new, naturally occurring fragments of plasminogen have been discovered. The new polypeptides are referenced herein as $A_{61}$ and p22. These polypeptides exhibit anti-angiogenic activity and as such they are useful in compositions for the treatment of diseases and conditions involving an unwanted and deleterious neovascularization.

Plasminogen is a single-chain glycoprotein present in plasma at a concentration of about 2 µM (Wohl et al., Thromb. Res. 27:523-535, 1982; Kang et al., Trends Cardiovasc. Med. 90:92-102, 1999). The human plasminogen polypeptide of which contains 791 amino acid (FIG. 1, amino acids 19-810). Native glu-plasminogen is readily converted to lys-plasminogen by plasmin hydrolysis of the Lys-77-Lys-78 bond (FIG. 1, amino acids 97-810). Plasminogen serves as a precursor to plasmin which is a protease formed by cleavage of plasminogen between Arg-561 and Val-562 by tissue plasminogen activator or urokinase-type plasminogen activator. Disulfide bridges form covalent bonds that link the two polypeptide chains of plasmin together. The larger polypeptide chain or plasmin A chain, which is also cleaved between Lys-77 and Lys-78 of plasminogen to form a chain of Lys-78 through Arg-561, contains five kringle domains while the smaller or B chain is formed from Val-562 through Asp-791 of plasminogen. Both plasminogen and plasmin bind to fibrin through amino-terminal kringle regions each of which is a triple loop region formed as a result of disulfide bonds. As used herein, the term "plasminogen" is intended to include human glu-plasminogen and lys-plasminogen as well as allelic variants of the human sequences. Also included are plasminogen orthologs from non-human mammalian species as well as from non-mammalian vertebrate species, a large number of which are known in the art.

The $A_{61}$ and p22 polypeptides and polynucleotides of the present invention correspond to portions of the polypeptide sequences and polynucleotide sequences, respectively, of plasminogen. The term "corresponds to" is used herein to mean that a that a polypeptide sequence is identical to a reference polypeptide sequence or a polynucleotide sequence is homologous (i.e., is identical, not strictly evolutionarily related) to all or a portion of a reference polynucleotide sequence. In contradistinction, the term "complementary to" is used herein to mean that the complementary sequence is not identical to the reference sequence, but comprised of a sequence of purine and pyrimidine bases precisely matched to the pyrimidine and purine bases, respectively of the reference sequence. For illustration, the nucleotide sequence "TATAC" corresponds to a reference sequence "TATAC" and is complementary to a reference sequence "GTATA".

$A_{61}$ has a major and a minor polypeptide isoform, the major isoform having a sequence of 391 amino acids (SEQ ID NO: 1) from Lys-78 to Lys-468 of plasminogen and the minor isoform having a sequence of 394 amino acids (SEQ ID NO:2) from Lys-78 to Arg-471 of plasminogen. Although the human $A_{61}$ isoforms are identified as portions of human plasminogen, it is intended that the term $A_{61}$ include orthologous sequences from non-human mammalian species as well as from non-mammalian vertebrate species. The sequences of such orthologous $A_{61}$ molecules can be readily determined by alignment of orthologous plasminogen sequences with human plasminogen and then identifying the portion of the molecule that represents $A_{61}$ polypeptides. Alternatively, putative orthologous $A_{61}$ polypeptides can be aligned with human $A_{61}$. It is believed that non-human mammalian orthologous $A_{61}$ polypeptides will have at least 75% sequence identity, i.e. at least 75% identical amino acids, as compared to human $A_{61}$ and that non-mammalian vertebrate orthologous $A_{61}$ polypeptides will have at least 60% sequence identity as compared to human $A_{61}$ polypeptides.

The p22 polypeptide has a sequence of 103 amino acids (SEQ ID NO:3) from Lys-78 to Lys-180 of plasminogen. Although the human p22 is identified as a portion of human plasminogen, it is intended that the term p22 include orthologous sequences from non-human mammalian species as well as from non-mammalian vertebrate species. The sequences of such orthologous p22 molecules can be readily determined by alignment of orthologous plasminogen sequences with human plasminogen. Alternatively, putative orthologous p22 molecules can be aligned with human p22. It is believed that non-human mammalian orthologous p22 polypeptides will have at least 75% sequence identity, i.e. at least 75% identical amino acids, as compared to human p22 and that non-mammalian vertebrate orthologous p22 polypeptides will have at least 60% sequence identity as compared to human p22.

Methods of sequence alignment for identifying homologous sequences which can be either paralogs or orthologs are well known in the art. For example, two or more sequences can be aligned using the Clustal method (Higgins et al, Cabios 8:189-191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in painvise alignment=5; diagonals saved in pairwise alignment=5. The residue weight table used for the alignment program is PAM250 (Dayhoff et al., in Atlas of Protein Sequence and Structure, Dayhoff, Ed., NBRF, Washington, Vol. 5, suppl. 3, p. 345, 1978).

Human $A_{61}$ polypeptides are further characterized in that they have a molecular weight of approximately 61 kDa as determined by SDS-polyacrylamide gel electrophoresis conducted under reducing conditions. Circular dichroism, which examines the secondary structure of molecules revealed that $A_{61}$ polypeptides exhibited a strong negative band at 202 nm and a weak positive band at about 227 nm. Analysis of secondary structure content suggested the presence of kringle-containing structures and capable of binding to free or C-terminal lysine residues. $A_{61}$ polypeptides are biologically active in inhibiting endothelial cell proliferation showing a concentration required for 50% inhibition ($IC_{50}$) to be 35±10 nM in in vitro cultured bovine capillary endothelial cells. Moreover, $A_{61}$ polypeptides at a dose of 2.5 mg/kg, i.p. inhibited metastatic tumor growth in mice challenged with Lewis Lung carcinoma cells.

Human p22 is further characterized in that it has a molecular weight of approximately 22 kDa as determined by SDS-polyacrylamide gel electrophoresis conducted under reducing conditions. Circular dichroism revealed that p22 exhibited a strong negative band at 202.7 and a positive band at 227.5 nm. In contrast, a recombinant kringle polypeptide exhibited a strong negative band at 197.4 nm and positive band at 227.5 suggesting that p22 has a different secondary structure from that of the recombinant kringle 1 polypeptide. Evaluation of the biological activity of p22 revealed that it inhibits endothelial cell proliferation in cultured bovine capillary endothelial cells at an $IC_{50}$ of 14.3±2.3 nM. Moreover, p22 at a dose of 2.5 mg/kg, i.p. inhibited metastatic tumor growth in mice challenged with Lewis Lung carcinoma cells.

The $A_{61}$ and p22 polypeptides of the present invention are naturally occurring polypeptides as is shown by identification of $A_{61}$ and p22 in the serum of normal subjects as well as serum of cancer patients. The term "naturally occurring" as used herein is intended to mean that the substance referenced exists in nature and can be found in the body of a vertebrate. The substance may exist continuously or only intermittently in the body or only during particular physiologic or pathologic conditions in the body. The particular sample of a substance with is "naturally occurring" may not itself be made in the body of a vertebrate, but may be made by other means such as by chemical synthesis, recombinant methods or the like, so long as the substance is identical to the that made in the body of a vertebrate. By way of comparison, a man-made substance which has no corresponding identical substance made in the body of a vertebrate is not considered herein to be "naturally occurring".

Also included within the scope of the present invention are polypeptides which are variants of $A_{61}$ and p22 polypeptides having sequences with conservative amino acid substitutions compared to the $A_{61}$ and p22 polypeptides. Conservative amino acid substitutions refer to the interchangeability of amino acids having similar chemical characteristics and/or having similar side chains. For example, a group of amino acids which are neutral and hydrophobic include alanine, valine, leucine, isoleucine, proline, tryptophan, phenylalanine and methionine; a group of amino acids which are neutral and polar include glycine, serine, threonine, tyrosine, cysteine, asparagine and glutamine; a group of amino acids which are basic include lysine, arginine and histidine; a group of amino acids which are acidic include aspartic acid and glutamic acid; a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; and a group of amino acids having sulfur-containing side chains is cysteine and methionine. Preferred conservative amino acids substitution groups are: valine-leucine-isoleucine, phenylalanine-tyrosine, lysine-arginine, alanine-valine, asparagine-glutamine, glutamic acid-aspartic acid, leucine-methionine, and glutamine-histidine.

The $A_{61}$ polypeptide of the present invention also includes glycosylated $A_{61}$. Glycoproteins are formed by attaching a carbohydrate side chain to an amino acid, most commonly, N-linked oligosaccharides in which the sugar is linked to the amino group of asparagine. Less common are O-linked oligosaccharides in which the sugar is linked to the hydroxyl group of serine or threonine. Glycosylation at any one or combination of these sites would increase the molecular weight of the molecule.

The $A_{61}$ and p22 polypeptides of the present invention isolated and purified polypeptides compared to their occurrence at very low levels and in a mixture of other substances in the body. An "isolated" substance or a "substantially pure" substance as used herein, particularly with reference to polypeptides or polynucleotides, is intended to mean that the substance is present, preferably, in an amount of at least about 50% on a molar basis of all macromolecular species present. More preferably, an isolated or substantially pure substance will comprise more than about 80% to about 90% of all macromolecular species present in the composition. Most preferably, the substance is purified to essential homogeneity wherein contaminant species cannot be detected in the composition by conventional detection methods and the composition consists essentially of a single macromolecular species. Solvent species, small molecules (<500 Daltons), and elemental ion species are not considered macromolecular species.

Methods for preparing the $A_{61}$ and p22 polypeptides are also within the scope of the present invention. $A_{61}$ and p22 can be produced by cell-mediated methods or by cell-free methods.

$A_{61}$ can be prepared in vitro by plasmin autodigestion. Earlier work generated plasminogen fragments of the plasmin A-chain in a cell-free system of plasminogen uPA and the sulfhydryl donor, N-acetyl-L-cysteine (see for example, Gately et al, *Proc. Natl. Acad. Sci. U.S.A.* 94:10868-10872, 1999; Fitzpatrick et al, *Biochemistry* 39:1021-1028, 2000). In contrast, the $A_{61}$ fragments of the present invention are generated as A-chain fragments by incubating plasminogen with uPA without any sulfhydryl donor. The reaction products can then be purified by L-lysine-Sepharose affinity and gel permeation chromatography. We have shown that the $A_{61}$ so produced is made up of two fragments which show an apparent mass of 61 and 64 kDa, respectively, on a Coomassie-stained, denaturing, reduced SDS-PAGE and an apparent mass of 50 kDa on Coomassie-stained denaturing, non-reduced SDS-PAGE. Typical recovery by this method is 51 mg $A_{61}$ from 100 mg plasminogen.

Cell-mediated systems can also be used to generate $A_{61}$. The cells are, preferably, mammalian cells, which can be derived from normal tissue or from cancerous tissue. Suitable mammalian cells are incubated overnight in media containing glu-plasminogen or lys-plasminogen, and cell-produced plasminogen fragments are produced. $A_{61}$ plasminogen fragments can be identified using reduced or non-reduced SDS-PAGE and Western blotting. We have found that HT1080 fibrosarcoma cells, bovine capillary endothelial cells and, to a lesser extent, HeLa cells and HUVEC cells were able to generate $A_{61}$. The $A_{61}$ plasminogen fragments so produced can be purified from the conditioned media by affinity chromatography.

The p22 plasminogen fragment can also be prepared in vitro. The method involves incubation of $A_{61}$ with plasmin and a reducing agent, such as dithiothreitol. Plasminogen fragments including p22 are thereby produced upon degradation of $A_{61}$. Subsequent purification of the reaction mixture using an L-lysine-Sepharose column results in the isolation of milligram quantities of p22.

Cell-mediated systems can also be used to generate p22. Preferably the cells are mammalian cells. Incubation of glu-plasminogen or lys-plasminogen with HT1080 human fibrosarcoma cells resulted in the generation of $A_{61}$ and p22 as well. The p22 fragment can be identified as a 22 kDa fragment in reduced SDS-PAGE and isolated using an L-lysine-Sepharose column.

$A_{61}$ polynucleotides and p22 polynucleotides are also within the scope of the present invention. Such polynucleotides encode $A_{61}$ polypeptides and p22 polypeptides, respectively. The human nucleic acid sequence of encoding human plasminogen precursor is shown in FIG. 2. The sequences encoding the two human $A_{61}$ isoforms are nucleic acids 343-1515 (SEQ ID NO:5) and nucleic acids 343-1524 (SEQ ID NO:6). The sequence encoding human p22 is nucleic acids 343-651 (SEQ ID NO:7). As would be readily appreciated by the skilled artisan, other nucleic acid sequences will encode the $A_{61}$ and p22 polypeptides as a result of code redundancy and these are also within the scope of the present invention.

The polynucleotides encoding $A_{61}$ polypeptides and the polynucleotides encoding p22 polypeptides also include sequences which encode human allelic variants of the polypeptides. In addition, the scope of the present invention includes polynucleotides encoding non-human mammalian polypeptides and non-mammalian vertebrate polypeptides.

Such polynucleotides in addition to the sequences shown in SEQ ID NOS:5-7 can be identified by virtue of their having at least a 90% identity with any one of SEQ ID NOS:5-7. By 90% sequence identity, it is meant that a sequence is of the same length and has at least 90% of the same bases as the reference sequence. Such sequences which are at least 90% identical to one of SEQ ID NOS:5-7 nevertheless, encode an $A_{61}$ or p22 polypeptide showing anti-angiogenic activity, preferably, endothelial cell anti-proliferative activity. $A_{61}$ polynucleotides encode the $A_{61}$ polypeptide of 391 and the $A_{61}$ polypeptide of 394, thus having 1173 consecutive nucleotides or 1182 consecutive nucleotides, respectively. The p22 polynucleotides encode p22 polypeptides of 103 contiguous amino acids thus having 309 consecutive nucleotides. Thus, in one embodiment, an $A_{61}$ polynucleotide can have 1173 consecutive nucleotides or 1182 consecutive nucleotides and also have at least 90% of the same bases as shown in SEQ ID NO:5 or SEQ ID NO:6, respectively. Similarly, in one embodiment, a p22 polynucleotide can have 309 consecutive nucleotides and at least 90% sequence identity with SEQ ID NO:7.

Nucleic acid sequences which specifically hybridize under stringent conditions with SEQ ID NOS:5, 6, or 7 are also within the scope of the present invention. Such polynucleotides, preferably, encode $A_{61}$ or p22 polypeptides and show anti-angiogenic activity. Stringent conditions or high stringency conditions allow one to distinguish a sequences which are not $A_{61}$ or p22 polynucleotides from sequences which are $A_{61}$ or p22 polynucleotides. Suitable stringent conditions can be selected by the skilled artisan on the basis of factors known to control the stringency of hybridization during hybridization and during the washing procedure, including temperature, ionic strength, length of time and concentration of formamide (See Sambrook et al., Molecular Cloning, 2nd Ed., 1989).

The present invention includes vectors comprising the $A_{61}$ or p22 polynucleotides as well as eukaryotic and prokaryotic cells comprising the vector. The cells can be mammalian cells. The mammalian cells can be, for example, human, murine, or bovine cells. The prokaryotic cells can be bacterial cells. The bacterial cells can be, for example E. coli cells. In addition, the vector can be, for example, a plasmid or a virus.

The present invention also includes the detection of $A_{61}$ polypeptides or p22 polypeptides in body fluids and tissues for the purpose of detection of diseases such as cancer or the angiogenic status of the diseases. As used herein, the term "detection" is intended to the determining of the presence of a disease in a patient, the distinguishing of the disease from other diseases, the estimation of prognosis in terms of probable outcome of the disease and prospect for recovery, the monitoring of the disease status or the recurrence of the disease, the determining of a preferred therapeutic regimen for the patient and the targeting of therapy. Such detection can involve any method known in the art for detecting proteins can be used including, but are not limited to immunodiffusion, immunoelectrophoresis, immunochemical methods, binder-ligand assays, immunohistochemical techniques, agglutination and complement assays. (for example see Basic and Clinical Immunology, Sites and Terr, eds., Appleton & Lange, Norwalk, Conn. pp. 217-262, 1991 which is incorporated by reference). Preferred are binder-ligand immunoassay methods including reacting antibodies with an epitope or epitopes of the $A_{61}$ polypeptides or p22 polypeptides and competitively displacing a labeled a $A_{61}$ or a p22 polypeptide or a derivative thereof.

As used herein, a derivative of an $A_{61}$ or a p22 polypeptide is intended to include a polypeptide in which certain amino acids have been deleted or replaced or changed to modified or unusual amino acids wherein the $A_{61}$ or a p22 derivative is biologically equivalent to $A_{61}$ or a p22 and wherein the polypeptide derivative cross-reacts with antibodies raised against the $A_{61}$ or a p22. By cross-reaction it is meant that an antibody reacts with an antigen other than the one that induced its formation.

Kits for measuring the levels of $A_{61}$ or a p22 in patient samples are also within the scope of the present invention. Such assay kits can be based any known protein assay method such as immunodiffusion, immunoelectrophoresis, immunochemical methods, binder-ligand assays, immunohistochemical techniques, agglutination and complement assays. Included in such kits are suitable reagents for conducting the assays.

Antibodies to $A_{61}$ and p22 are also within the scope of the present invention. Such antibodies can be polyclonal or monoclonal antibodies. Polyclonal antibodies can be prepared by immunizing rabbits or other animals by injecting antigen followed by subsequent boosts at appropriate intervals. The animals are bled and sera assayed against purified $A_{61}$ or p22 polypeptide. When using avian species, e.g. chicken, turkey and the like, the antibody can be isolated from the yolk of the egg. Monoclonal antibodies can prepared after the method of Milstein and Kohler by fusing splenocytes from immunized mice with continuously replicating tumor cells such as myeloma or lymphoma cells. (Milstein and Kohler Nature 256:495-497, 1975; Gulfre and Milstein, Methods in Enzymology: Immunochemical Techniques 73:1-46, Langone and Banatis eds., Academic Press, 1981 which are incorporated by reference). The hybridoma cells so formed are then cloned by limiting dilution methods and supernates assayed for antibody production by ELISA, RIA or bioassay.

Specific antibodies, either polyclonal or monoclonal, to the $A_{61}$ or p22 can be produced by any suitable method known in the art as discussed above. For example, murine or human monoclonal antibodies can be produced by hybridoma technology or, alternatively, the $A_{61}$ or p22 polypeptide, or an immunologically active fragment thereof, or an anti-idiotypic antibody, or fragment thereof can be administered to an animal to elicit the production of antibodies capable of recognizing and binding to $A_{61}$ or p22 polypeptides. Such antibodies can be from any class of antibodies including, but not limited to IgG, IgA, IgM, IgD, and IgE or in the case of avian species, IgY and from any subclass of antibodies.

The present invention also includes methods of treating or preventing angiogenic diseases and conditions. Such angiogenic diseases and conditions include, for example, solid tumors; blood born tumors such as leukemias; tumor metastasis; benign tumors, such as hemangiomas, acoustic neuromas, neurofibromas, trachomas, and pyogenic granulomas; rheumatoid arthritis; psoriasis; ocular angiogenic diseases, such as, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; wound granulation; intestinal adhesions; Crohn's disease; atherosclerosis; scleroderma; and hypertrophic scars, i.e., keloids.

The method of treatment involves administration to a patient an angiogenesis-inhibiting amount of a $A_{61}$ and/or p22 to the mammal. The method is applicable to any disease or condition involving unwanted angiogenesis, in particular the growth of tumors in cancer. The mammal is preferably a human and the $A_{61}$ and/or p22 are preferably human polypeptides. The $A_{61}$ and/or p22 can also be administered in combination with other agents to treat the particular disease such as, for example, other anti-cancer agents for treating cancer.

Cytotoxic agents can also be linked to $A_{61}$ or to p22 to provide a composition which can be used to target cancer cells. Such cytotoxic agents include ricin, deoxyribonuclease, diphtheria toxin, pseudomonal exotoxin, ribonuclease and the like.

Gene therapy approaches are also within the scope of the present invention. Such can include administration of the polynucleotides of the present invention or compositions of the polynucleotides in a vector system such as a noninfectious viral vector to deliver the polynucleotide fragment to the target cells of the patient. Chemical approaches can also be used in the administration of the polynucleotides, including incorporation into liposomes as well as conjugating with lipofectins or cytofectins.

Also included in the present invention are ex vivo approaches in which the polynucleotides of the present invention are administered to cells obtained from the patient, followed by administration or implantation of the cells into the patient $A_{61}$ or p22 can also be administered to vascular endothelial cells to prevent proliferation. The cells can be in vitro or in vivo. The method comprises administering to the cells $A_{61}$ or p22 or a combination thereof in an amount suitable for inhibiting endothelial cell proliferation.

The present invention also includes therapeutic or pharmaceutical compositions of $A_{61}$ or p22 polypeptides or polynucleotides. The compositions comprise an effective amount for treating patients with angiogenic diseases or conditions in pharmaceutically acceptable formulations. These formulations can be administered by standard routes of administration such as, for example, by topical, transdermal, intraperitoneal, intracranial, intracerebroventricular, intracerebral, intravaginal, intrauterine, oral, rectal, intravenous, intraspinal, subcutaneous or intramuscular routes. The $A_{61}$ or p22 molecules can also be linked or conjugated with agents that provide desirable pharmaceutical or pharmacodynamic properties. For example $A_{61}$ or p22 can be conjugated polyethylene glycol to provide more desirable pharmacokinetic parameters. Delivery methods known in the art such as osmotic minipumps may also be used to provide a targeted delivery at the site of a tumor. Parenteral administration can be either rapid as by injection or over a period of time as by slow infusion or administration of slow release formulation.

The compositions of the present invention are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. The compositions of the present invention can also be incorporated into a solid or semi-solid biologically compatible matrix such as a polymer which can be implanted into tissues requiring treatment. Such compositions can be implanted to allow for targeting at a particular tumor site or to provide slow release, for example, at the site of a tumor or implanted so that the angiostatin is slowly released systemically.

The carrier can include pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion into the cerebrospinal fluid by continuous or periodic infusion.

Dose administration can be repeated depending upon the pharmacokinetic parameters of the dosage formulation and the route of administration used.

It is also contemplated that certain formulations containing $A_{61}$ or p22 can be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and promote absorption such as, for example, surface active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates the generation and identification of $A_{61}$ plasmin(ogen) fragments produced by plasmin autodigestion using a cell-free system.

Previous reports (Gately et al. (1997) *Proc. Natl. Acad. Sci. U.S.A.* 94: 10868-10872; U.S. Pat. No. 5,801,012 to Soff et al.) showed that a kringle 1-4-containing plasminogen cleavage product of 50 kDa (non-reduced SDS-PAGE) was generated in a cell-free system consisting of plasminogen, u-plasminogen activator, and the sulfhydryl donor N-acetyl-L-cysteine. It was also reported that the formation of the kringle 1-4 plasminogen A-chain fragment was absolutely dependent on the presence of a sulfhydryl donor such as N-acetyl-L-cysteine.

In a reinvestigation of the dependency on the presence of a sulfhydryl donor to generate a plasminogen fragment comprising kringles 1-4 by plasmin autodigestion, the present inventors unexpectedly observed that plasmin(ogen) autodigestion in the absence of a sulfhydryl donor generated of novel molecular species. These species, comprising a major band of 61 kDa and a minor band of 64 kDa were collectively named "$A_{61}$" to avoid confusion with the plasminogen fragment angiostatin.

To generate $A_{61}$, [Glu]plasminogen (40 µM) was incubated overnight at 37° C. (in the absence of a sulfhydryl donor) in a buffer containing 50 mM Tris-HCl (pH 9.0), 20 mM L-lysine, 100 mM NaCl, 1 mM EDTA, and 0.17 µM two-chain u-plasminogen activator (urokinase), thereby forming a mixture including the $A_{61}$. Following the incubation, the mixture was diluted 4-fold with a buffer comprising 20 mM Hepes (pH 7.4) and 140 mM NaCl, adjusted to 1 mM diisopropylfluorophosphate (DIFP), and applied to an L-lysine-Sepharose affinity chromatography column (Pharmacia) previously equilibrated with equilibration buffer comprising 20 mM Hepes (pH 7.4) and 140 nM NaCl. After a 5-column volume wash with equilibration buffer, the column was subjected to a linear gradient of 0-125 mM ε-amino-n-caproic acid, and a single protein peak (as observed by monitoring sample absorbance of 280 nm ultraviolet light) was eluted, pooled, and concentrated by ultrafiltration. Application of this protein peak to a Sephacryl S-100 column (Pharmacia) previously equilibrated with equilibration buffer resulted in the elution of a single protein peak that was collected in fractions. The fractions were pooled, then divided into aliquots which were stored frozen at −80° C. until further use. Samples from the protein peak were analyzed by sodium dodecyl sulfate-polyacrylamide gel electrophoresis (SDS-PAGE; Laemmli, U. K. (1970) *Nature* 227: 680-685).

For Western blotting, proteins were transferred from gels to 0.45-µm pore size nitrocellulose membranes using a Bio-Rad transblot apparatus at 4° C. for 1 h for mini-gels or overnight for larger gels. The membranes were then blocked in TPBS (wherein TPBS is phosphate-buffered saline containing 137 mM NaCl, 8 mM $Na_2HPO_4$, 1.4 mM $KH_2PO_4$, 2.7 mM KCl (pH 8.0), and 0.1% Tween 20 detergent) containing 5% skim milk at room temperature for 1 h and then incubated with primary antibody in TPBS containing 1% skim milk at 4° C. overnight. The following dilutions of primary antibody were used: 1:5000 dilution of 1 mg/ml monoclonal anti-human plasminogen kringle 1-3 antibody; 1:500 dilution of 0.1 mg/ml monoclonal anti-human angiostatin antibody (GF-47); 1:500 dilution of polyclonal anti-mouse angiostatin antibody. Blots were then washed with TPBS at least 6 times (10 minutes each) at room temperature and then incubated in 1:1000 dilution of anti-mouse or anti-rabbit horseradish peroxidase-conjugated secondary antibody in TPBS containing 1% skim milk at 37° C. for 1 hour. Membranes were then washed with TPBS at least six times (10 minutes each), developed with the Supersignal reagent (Pierce), and visualized by chemiluminescence.

Figure 3B:
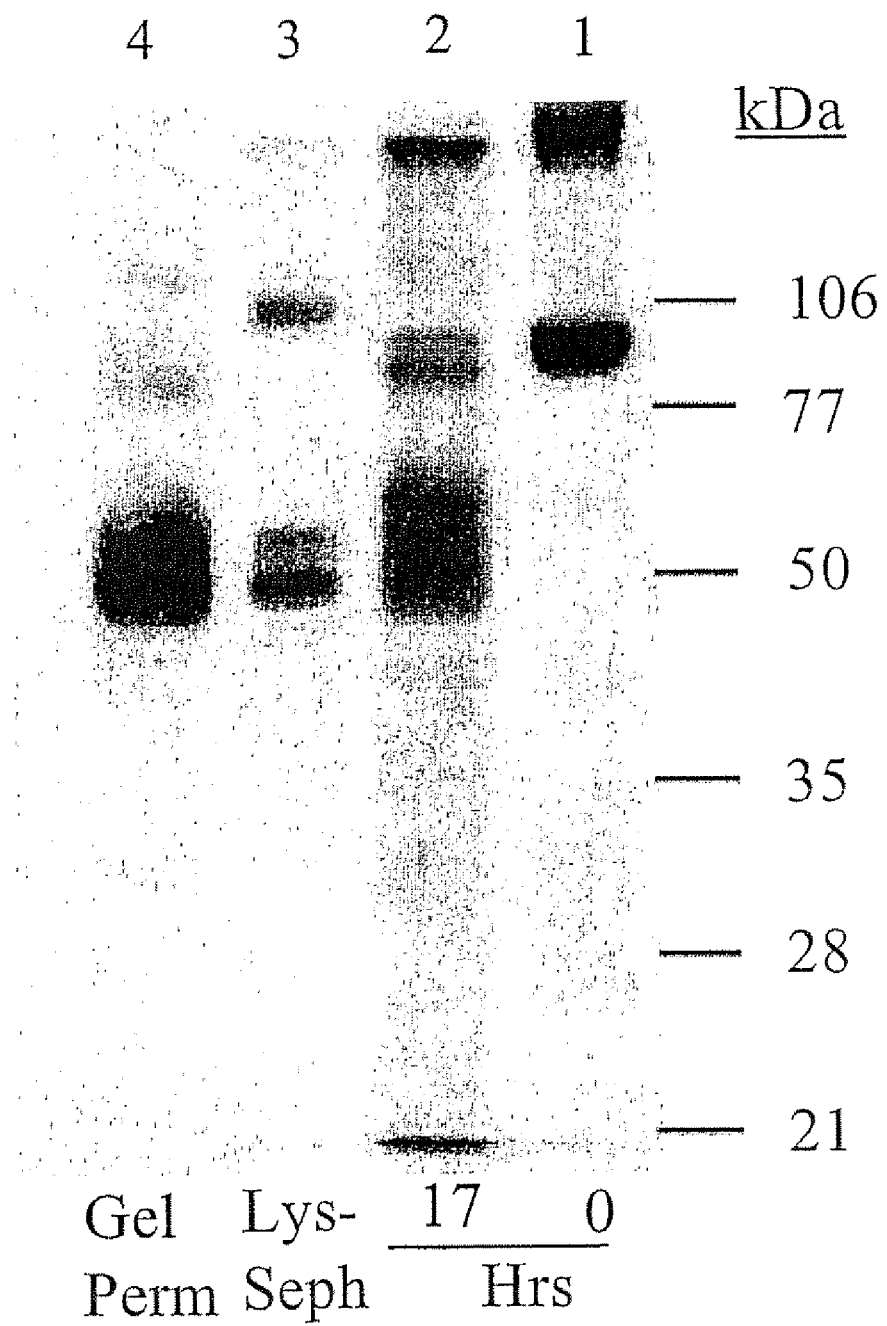
Figure 3C:
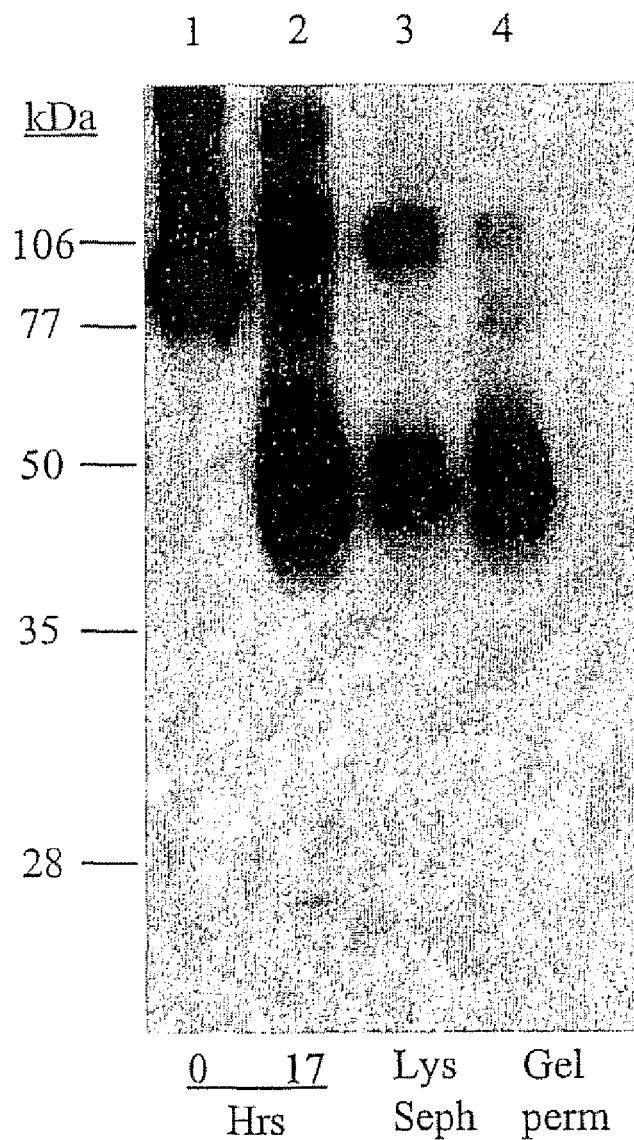

FIG. 3 illustrates the generation and isolation of $A_{61}$ produced in a cell-free system. To produce, [Glu]plasminogen (40 µM) was incubated in buffer comprising 50 mM Tris-HCl (pH 9.0), 20 mM L-lysine, 100 mM NaCl, 1 mM EDTA, and 0.17 µM two-chain u-plasminogen activator (lane 1). The reaction mixture was incubated at 37° C. overnight (lane 2). The mixture was diluted 4-fold with equilibration buffer adjusted to 1 mM diisopropylfluorophosphate, and applied to a lysine-Sepharose column previously equilibrated equilibration buffer. After a 5-column volume wash with equilibration buffer, the column was subjected to a linear gradient of 0-125 mM F-amino-n-caproic acid. Fractions comprising the 61- and 64 kDa plasminogen fragments were collected and pooled (lane 3), concentrated by ultrafiltration, and applied to a Sephacryl gel permeation (Gel Perm) chromatography column previously equilibrated with equilibration buffer. The protein peak was then pooled (lane 4). Aliquots of pooled fractions were analyzed by reduced (A) and non-reduced SDS-PAGE (B) and stained with Coomassie Blue. Alternatively, aliquots were analyzed by non-reduced SDS-PAGE, transferred to a nitrocellulose membrane, and analyzed by Western blotting (below) using a monoclonal antibody against human plasminogen kringles 1-3 as the primary antibody (FIG. 3C).

Comparison of stained bands with molecular size standards on a gel run under reducing conditions established that the protein peak comprised an isolated doublet comprising major and minor proteins of $M_r$ 61,000 and 64,000, respectively Therefore, these A-chain fragments were collectively named $A_{61}$. The concentration of $A_{61}$ was determined using an $\epsilon_{1\%, 280\ nm}$ 13.6 and a molecular mass of 61 kDa. Recovery was about 51 mg of $A_{61}$ from 100 mg of [Glu]plasminogen. $A_{61}$ was also formed with a comparable yield when [Lys]plasminogen was substituted for [Glu]plasminogen.

To investigate the mechanism of $A_{61}$ production, the time course of generation of $A_{61}$ from plasminogen and u-plasminogen activator was examined using SDS-PAGE under reducing and non-reducing conditions. For these experiments, [Glu]plasminogen (8.7 µM) was incubated at 37° C. in a buffer containing 50 mM Tris (pH 9.0), 100 mM NaCl, 1 mM EDTA, and 20 mM L-lysine. Samples were removed at time intervals as indicated in FIG. 4, and the reaction stopped by dilution and heating of the samples in SDS-PAGE sample buffer (with or without reducing agent), then subjected to SDS-PAGE under reducing or non-reducing conditions.

Figure 4A:
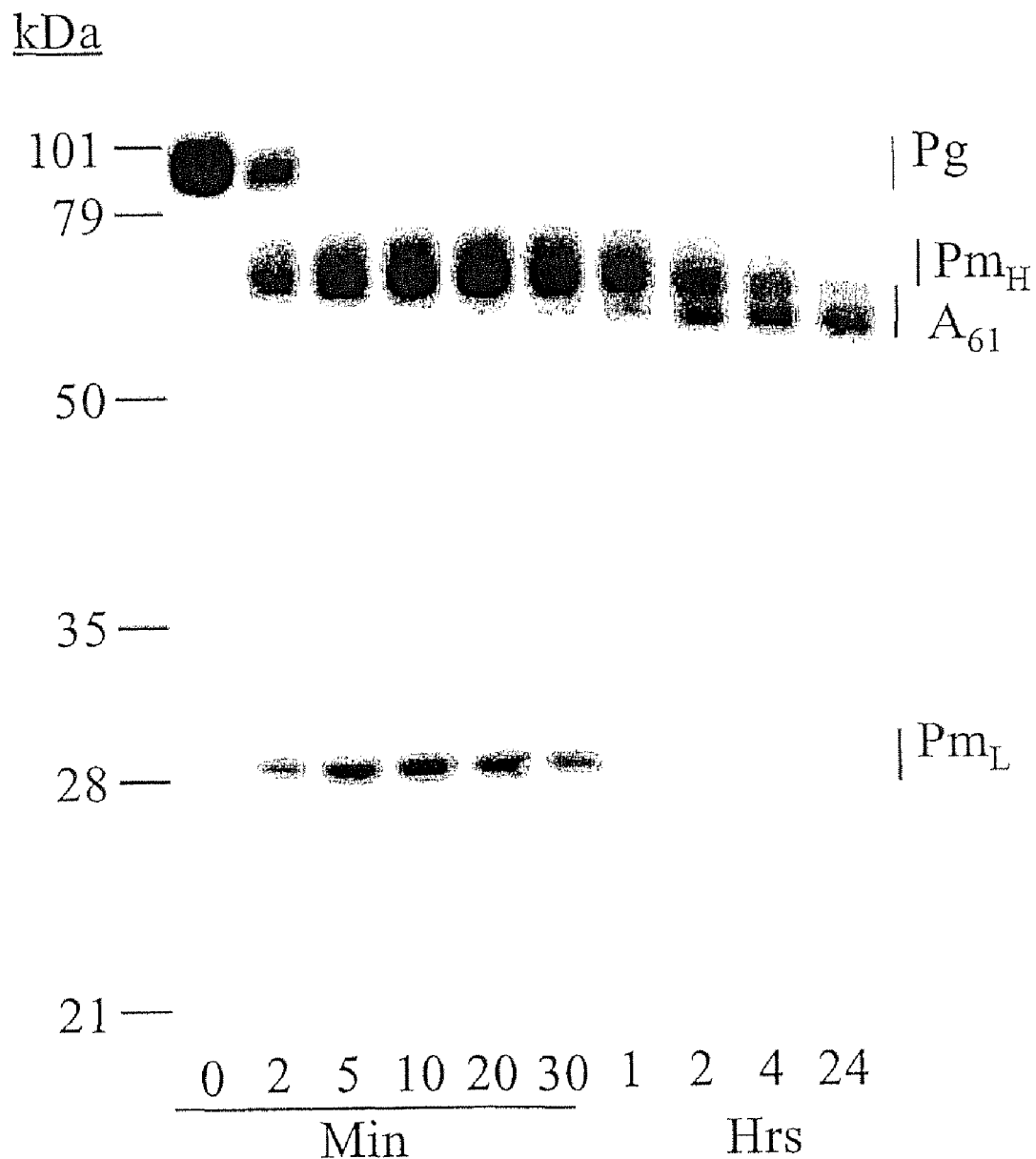
FIG. 4 illustrates the time course of plasminogen cleavage to form $A_{61}$ as analyzed in reduced SDS-PAGE with Coomassie Blue staining (A) and in non-reduced SDS-PAGE with Coomassie Blue staining (B).
Figure 4B:
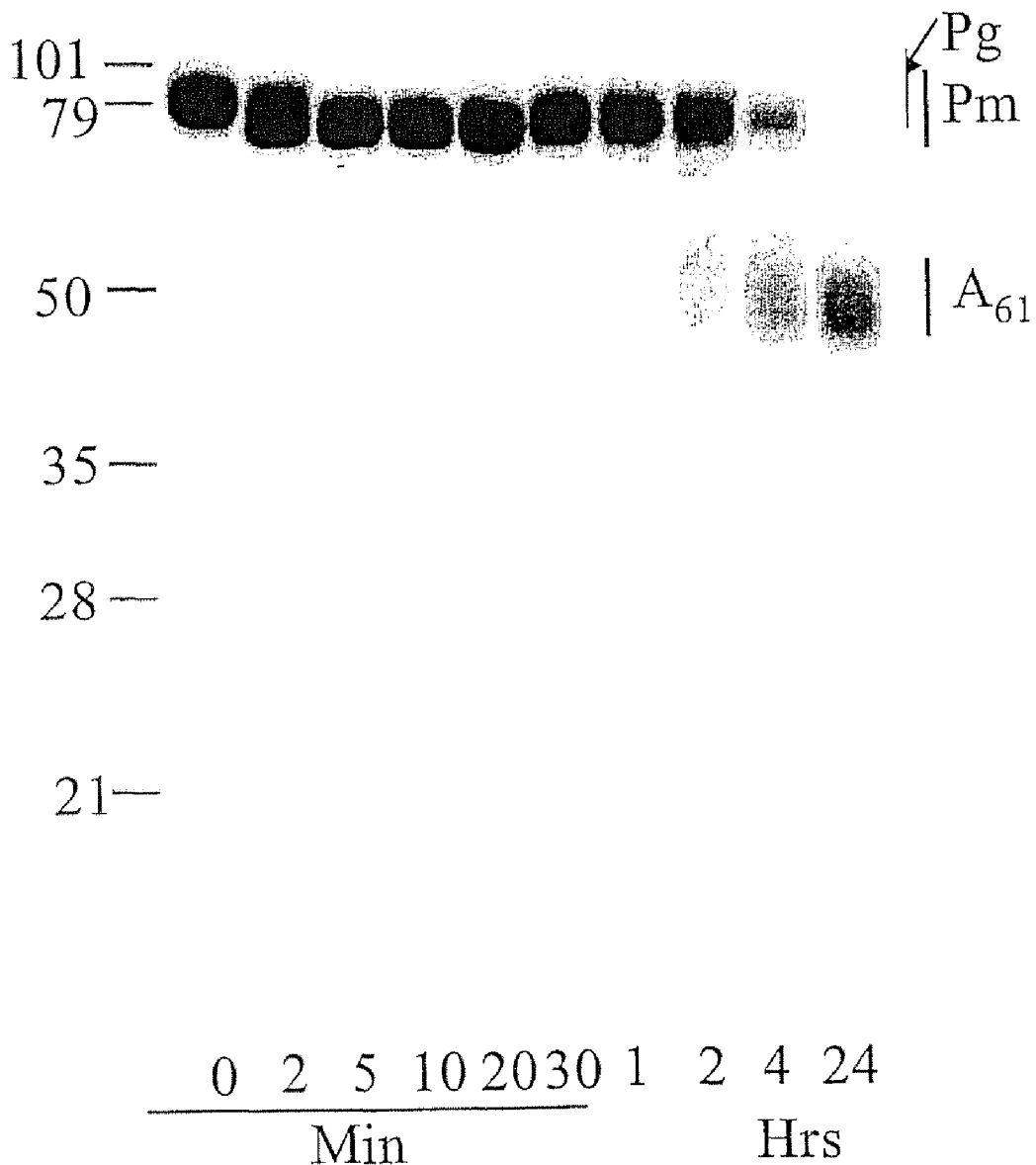

FIG. 4 shows a time course analysis of plasminogen cleavage to $A_{61}$. [Glu]plasminogen (8.7 µM), incubated as described above. The reaction was initiated by addition of 39 nM u-plasminogen activator. Aliquots of the reaction were removed at the indicated times, subjected to reduced (FIG. 4A) and non-reduced-SDS-PAGE (FIG. 4B), and stained with Coomassie Blue. $Pm_H$ indicates plasmin heavy chain; $Pm_L$ indicates plasmin light chain.

The data shown in FIG. 4 indicate that [Glu]plasminogen (8.7 μM) is completely converted to plasmin by about 5 minutes after initiation of the reaction by addition of u-plasminogen activator (39 nM). However, at this point in the reaction, $A_{61}$ is not observed. After the reaction progresses for about 1 h, degradation of the plasmin heavy and light chains becomes apparent. Analysis of reaction products by SDS-PAGE shows that by about 2-4 hours after initiation of the reaction, $A_{61}$ is apparent, exhibiting $M_r$'s of about 61,000 and 64,000 on gels run under reducing conditions and an $M_r$ of about 50,000 in gels run under non-reducing conditions.

Separate experiments demonstrated that a recombinant human plasminogen (S741C) that is catalytically inactive when converted to plasmin was not converted to $A_{61}$ (Horrevoets, A. J. G. et al. (1997) *Journal of Biological Chemistry* 272: 2176-2182). While not wishing to be bound by theory, these results indicate that plasminogen is cleaved by u-plasminogen activator to form plasmin which then undergoes autodigestion resulting in the formation of $A_{61}$. Because $A_{61}$ can be generated by plasmin autoproteolysis, plasmin obtained by methods other than u-plasminogen activator cleavage of plasminogen, for example converting plasminogen to plasmin using other plasminogen activators such as t-plasminogen activator or streptokinase, or generating plasmin using recombinant DNA methods, can substitute to generate plasmin that can undergo autoproteolysis to form $A_{61}$.

The concept that plasmin is capable of autodigestion in the absence of sulfhydryl donors is not novel. Other laboratories have shown that plasmin autodigestion involves a bimolecular reaction in which both heavy and light chains are proteolyzed (Walther, P. J., et al., (1974) J. Biol. Chem. 249, 1173-1181; Grimard, M. (1976) Biochimie (Paris) 58, 1409-1412; Gaffney, P. J., et al., (1977) Haemostasis 6, 72-88; Reddy, K. N., and Wagner, C. J. (1980) Biochem. Biophys. Res. Commun. 92, 1016-1022; Jespersen, J., et al., (1986) Thromb. Res. 41, 395-404; Wu, H. L., et al., (1987) Proc. Natl. Acad. Sci. U.S.A. 84, 8793-8795; Shi, G. Y., and Wu, H. L. (1988) Thromb. Res. 51, 355-364). Two autodigestive processes involving human plasmin have been reported by Wu and co-workers (Shi, G. Y., and Wu, H. L. (1988) Thromb. Res. 51, 355-364). In a slightly acidic solution the light chain was found to be cleaved faster than the heavy chain of plasmin. The cleavage of the light chain correlated with loss of plasmin activity. Both the heavy chain and the light chain were cleaved at pH levels between 6.5 and 11.0. On the other hand, alkaline pH favored the cleavage of the heavy chain. A cleaved heavy chain of molecular weight 50,000 (reduced SDS-PAGE) or 58,000 was observed (Shi, G. Y., and Wu, H. L. (1988) Thromb. Res. 51, 355-364). The C terminus of the $M_r$ 58,000 fragment was shown to be $Arg^{530}$. Based on these data it has been theorized that because of their proximity in the plasminogen structure, the disulfide bonds between $Cys^{512}$ and $Cys^{536}$ and between $Cys^{462}$ and $Cys^{541}$ could be split by hydroxyl ions. Without wishing to be bound by theory, the cleavage of the disulfide bonds between $Cys^{462}$ and $Cys^{541}$ could explain how plasmin autodigestion results in the formation of $A_{61}$ in the absence of sulfhydryl donors or a plasmin reductase.

EXAMPLE 2

This example illustrates the generation and identification of $A_{61}$ plasmin(ogen) fragments produced by contacting plasminogen with cells in vitro.

The ability of many cells to bind plasminogen and convert the plasminogen to plasmin at the cell surface has been well established. Whereas plasminogen can be converted to plasmin at the cell surface by the action of plasminogen activators such as u-plasminogen activator, it has been recently shown that other plasminogen fragments are also produced at the cell surface (Gately, S., et al. (1996) *Cancer Res.* 56: 4887-4890; O'Mahony, C. A., et al. (1998) *J. Surg. Res.* 77: 55-58; Westphal, J. R., et al. (2000) *Int. J. Cancer* 86: 760-767). To compare the plasminogen fragments produced on the cell surface with $A_{61}$, human HT1080 fibrosarcoma cells were incubated with [Glu]plasminogen, and the cell-produced plasminogen fragments were analyzed by reduced or non-reduced SDS-PAGE and Western blotting.

To generate $A_{61}$ with the aid of cells, human HT1080 or bovine capillary endothelial (BCE) cells were grown in Dulbecco's Modified Eagle Medium (DMEM; JRH Biosciences or GIBCO-BRL) supplemented with 10% heat-inactivated fetal calf serum, 2 mM L-glutamine, 10 units/ml penicillin G and 10 μM streptomycin sulfate in T75 tissue culture flasks at 37° C. Approximately $1 \times 10^5$ cells in 1 ml were added to each well of 24-well tissue culture plates and incubated at 37° C. for approximately 24 hr, wherein the cells formed monolayers. The cells monolayers were washed three times with phosphate buffered saline (PBS; 137 m NaCl, 8 mM $Na_2HPO_4$, 1.4 mM $KH_2PO_4$, 2.7 mM KCl, pH 8.0), and 0.5 to 8 μM [Glu]-plasminogen in DMEM was then added to each well, thereby forming a mixture including the $A_{61}$. Culture medium (about 100 ml) was collected after overnight incubation and centrifuged at about 2000×g at 4° C. for about 30 min to remove cell debris. Supernatants from the centrifuged samples were then applied to an L-lysine-Sepharose affinity chromatography column previously equilibrated with equilibration buffer. After a 5-column volume wash with equilibration buffer, the column was subjected to a linear gradient of 0-125 mM ε-amino-n-caproic acid. Fraction samples were subjected to SDS-PAGE conducted with or without reducing agent, and analyzed by Western blotting (below) using a monoclonal antibody against human plasminogen kringles 1-3 as the primary antibody. The peak fractions containing $A_{61}$ were pooled and concentrated. The proteins were desalted using a Sephadex PD-10 column (Amersham Pharmacia Biotech) into endotoxin-free PBS (Life Technologies, Inc.), filtered, and frozen in small aliquots at 80° C. SDS-PAGE and Western blot analysis indicates that some (but not all) mammalian cell types are capable of generating $A_{61}$ from plasmin(ogen).

FIG. 13 shows a comparison of $A_{61}$ with cell-generated plasminogen fragments. For these experiments, HT1080 cells were incubated with DMEM containing the indicated concentrations of [Glu]plasminogen. After an overnight incubation, the media were analyzed by 15% reduced (FIG. 13A) and non-reduced (FIG. 13B) SDS-PAGE followed by Western blotting with monoclonal anti-human plasminogen kringle 1-3 antibody: [Glu]plasminogen standard (lane 1); [Glu] plasminogen (8 μM) after overnight incubation in the absence of cells (lane 2). The HT1080 cells were incubated with the following concentrations of [Glu]plasminogen; 0.5 μM (lane 3); 1 μM (lane 4); 2 μM (lane 5); 4 μM (lane 6); 8 μM [Glu]plasminogen (lane 7); $A_{61}$ standard (lane 8).

Figure 13A:
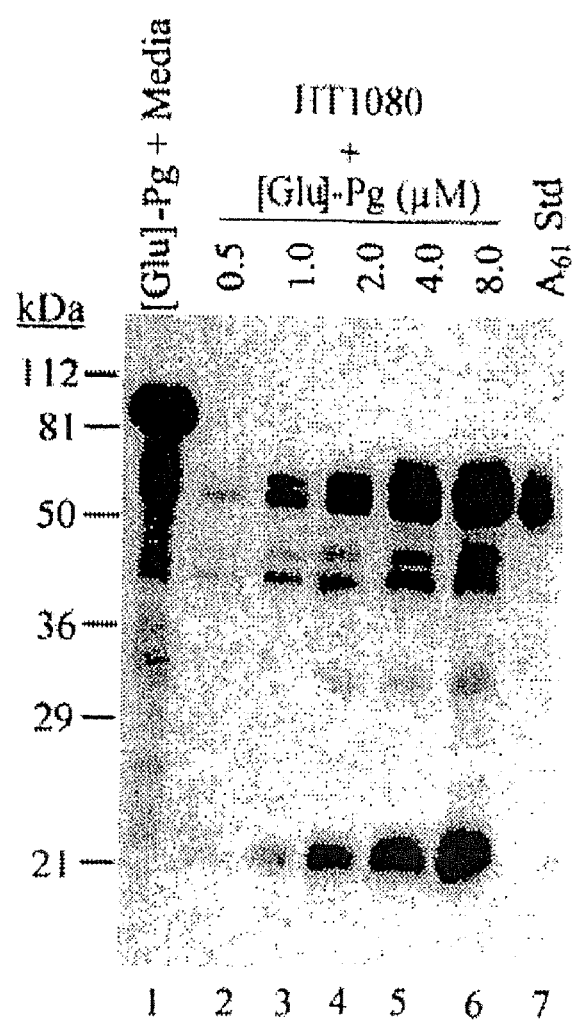
FIG. 13 illustrates the identification of a novel plasminogen fragment (p22) produced by HT-1080 cells.
Figure 13B:
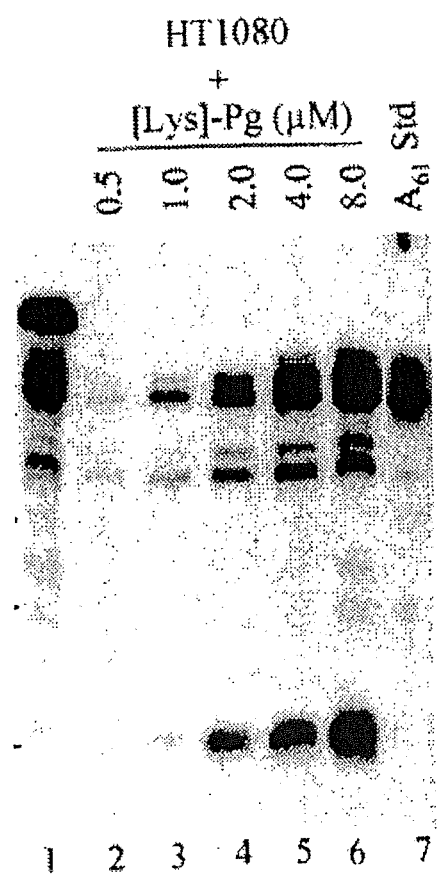
Figure 13C:
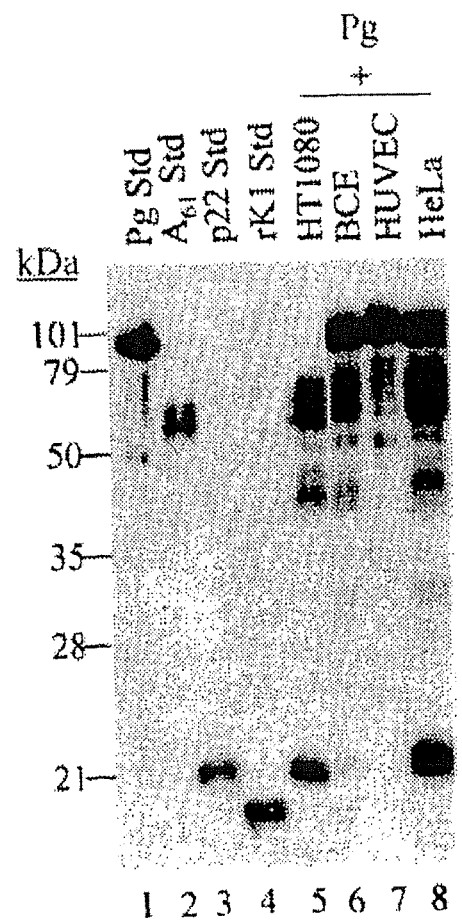

As shown in FIG. 13C, Human [Glu]plasminogen (8 μM) in DMEM was incubated overnight with a variety of cell lines. After an overnight incubation the media were subjected to 12.5% reduced SDS-PAGE followed by Western blotting with the monoclonal anti-human plasminogen kringle 1-3 antibody. The plasminogen standard (lane 1) and $A_{61}$ standard (lane 2) are also shown. Plasmin(ogen) and digestion products resulting from plasmin(ogen)/cell contact are shown by Western blot for the following cell lines: HT1080 cells (lane 3), HeLa cells (lane 4), BCE cells (lane 5), or HUVECs (lane 6).

The results demonstrate that both HT 1080 and BCE cells convert plasmin(ogen) to a molecule indistinguishable by Western blot analysis from $A_{61}$ generated using the cell-free system. First, it was found that cultured cells produced a plasminogen fragment of similar $M_r$ to that of $A_{61}$ which indicates that the predominant cell-produced A-chain fragment was composed of at least four intact kringles. Second, the observation that BCE cells produced an $A_{61}$-like protein indicates that the formation of A-chain fragments is not restricted to cancer cells. Furthermore, N-terminal sequencing of the $A_{61}$-like plasminogen fragment produced by the HT1080 or BCE cells established that the N terminus of the cell-produced $A_{61}$ is identical to $A_{61}$ produced using the cell-free system.

Figure 13D:
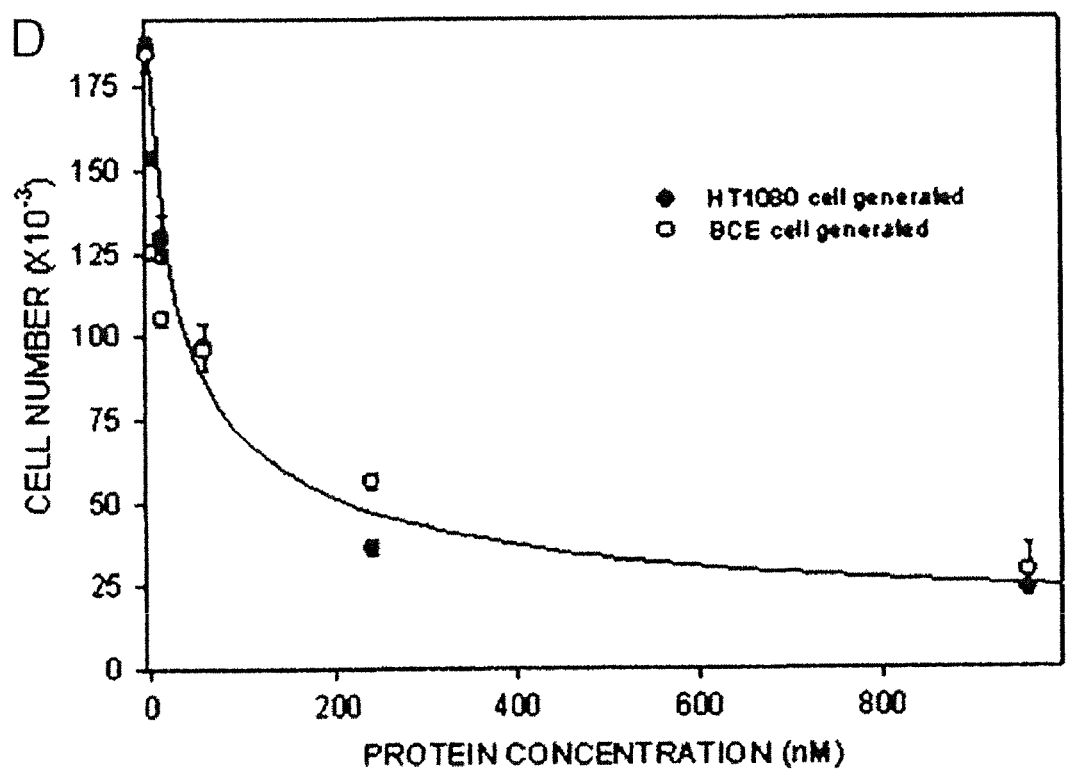

To demonstrate the inhibitory effect of $A_{61}$ generated by cell/plasminogen contact on endothelial cell proliferation in vitro, a growth inhibition assay was as described in Example 5 below. For these experiments, Human [Glu]plasminogen (2.7 μM) was incubated with HT1080 or BCE cells overnight (FIG. 13D). The $A_{61}$ was purified from the culture media of the HT1080 (closed circles) and BCE cells (open circles) by affinity chromatography with L-lysine-Sepharose. Various concentrations of the cell-generated $A_{61}$ were added to BCE cells, and the extent of inhibition of BCE cell growth was determined as indicated in Example 5. The observation that the $A_{61}$-like protein produced by HT1080 or BCE cells possessed potent anti-angiogenic activity further supports our notion that normal unstimulated cells can produce anti-angiogenic plasminogen fragments.

Because the molecular and biological properties of the plasmin(ogen) fragments produced by using the cell-free method or by contacting plasminogen with BCE or HT1080 cells appear identical, it is believed that these methods can all be used to generate $A_{61}$.

EXAMPLE 3

This example demonstrates the presence of $A_{61}$ in sera of healthy and diseased mammals, including mice.

It was originally proposed that the angiostatin fragment plasminogen of $M_r$ 38,000-43,000 on SDS-PAGE under reducing conditions was present in the urine and serum of mice bearing Lewis lung carcinoma tumors, but not in the serum of normal mice or tumor-resected mice (O'Reilly, M. S., et al., (1994) Cell 79: 315-328). Accordingly, serum was examined for the presence of an $A_{61}$-like fragment. In these experiments, 200 μl of mouse or human serum was incubated at room temperature for 30 min with 50 μl of a 1:1 suspension of L-lysine-Sepharose matrix (previously equilibrated with equilibration buffer). The matrix was subsequently washed with 5 volumes of the same buffer. The bound proteins were eluted by boiling the resin with SDS-PAGE sample buffer, and 20 μl of each sample was subjected to non-reduced SDS-PAGE and Western blotting.

Figure 5A:
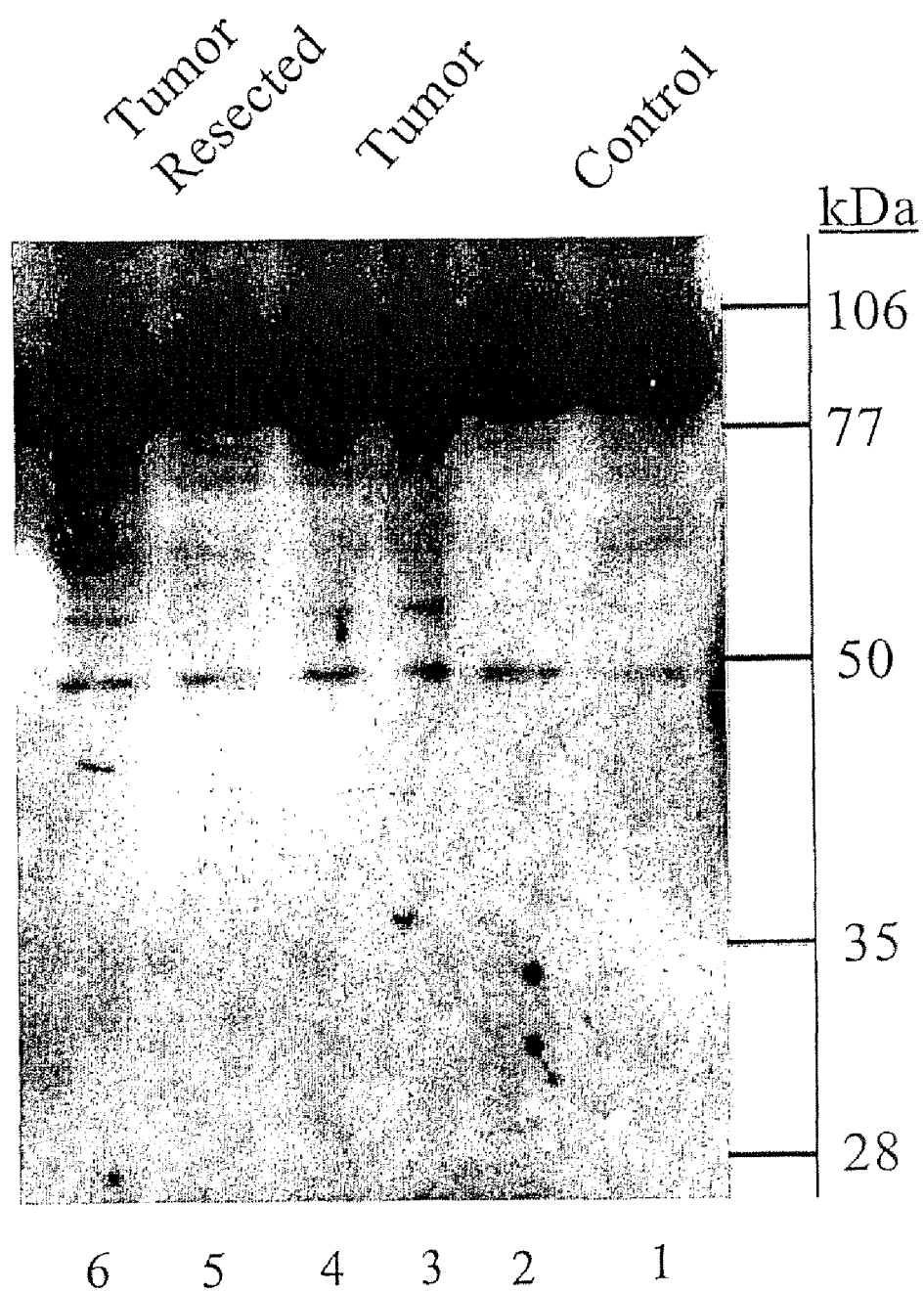
FIG. 5 illustrates Western blots comparing $A_{61}$ and plasminogen fragments present in mouse sera using rabbit anti-mouse angiostatin antibody (A) or monoclonal anti-human plasminogen kringle 1-3 antibody (B).
Figure 5B:
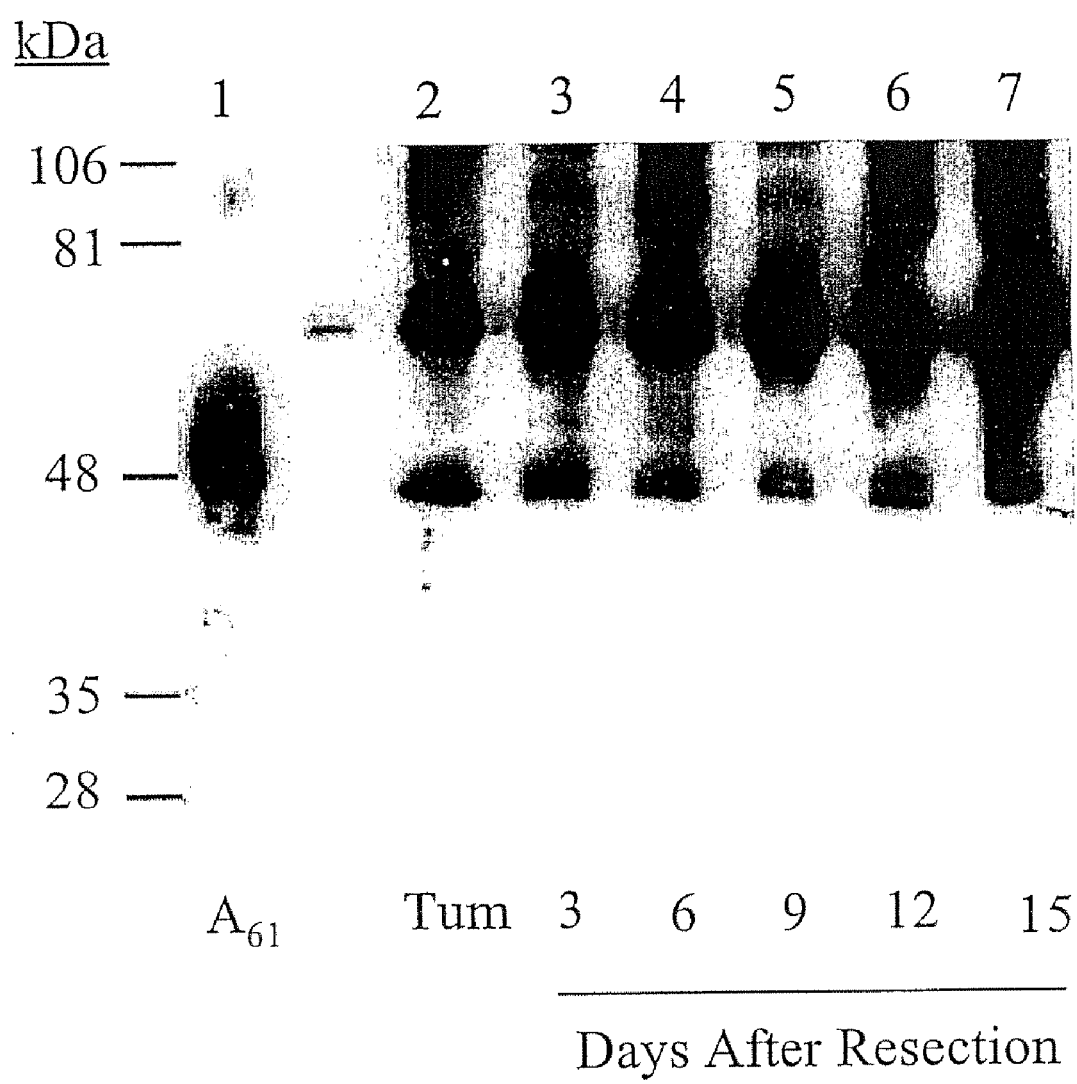

FIG. 5 presents a comparison of $A_{61}$ with plasminogen fragments present in mouse sera. Sera collected from mice were incubated with 50 μl of L-lysine-Sepharose (equilibrated in 20 mM Hepes, (pH 7.4), 140 mM NaCl) for 30 min at room temperature. The matrix was washed with 5 volumes of equilibration buffer, boiled with SDS-PAGE sample buffer, and subjected to non-reduced SDS-PAGE. Western blotting was performed with rabbit anti-mouse angiostatin antibody (FIG. 5A) or monoclonal anti-human plasminogen kringle 1-3 antibody (FIG. 5B). The lanes in FIG. 5A are as follows: control mouse serum, (1 and 2); mouse serum from two individual mice with 14-day old Lewis Lung Carcinoma tumor (see Example 5 below), (3 and 4); mouse serum from two individual mice 14 days after tumor resection, (5 and 6). The lanes in FIG. 5B are as follows: $A_{61}$ standard (1); mouse with 14-day old tumor (2); 3 days after tumor resection (3); 6 days after tumor resection (4); 9 days after tumor resection (5); 12 days after tumor resection (6); 15 days after tumor resection (7).

The results in A were consistent with test groups consisting of 21 normal mice, 9 tumor-bearing mice, and 29 tumor-resected mice.

Figure 6:
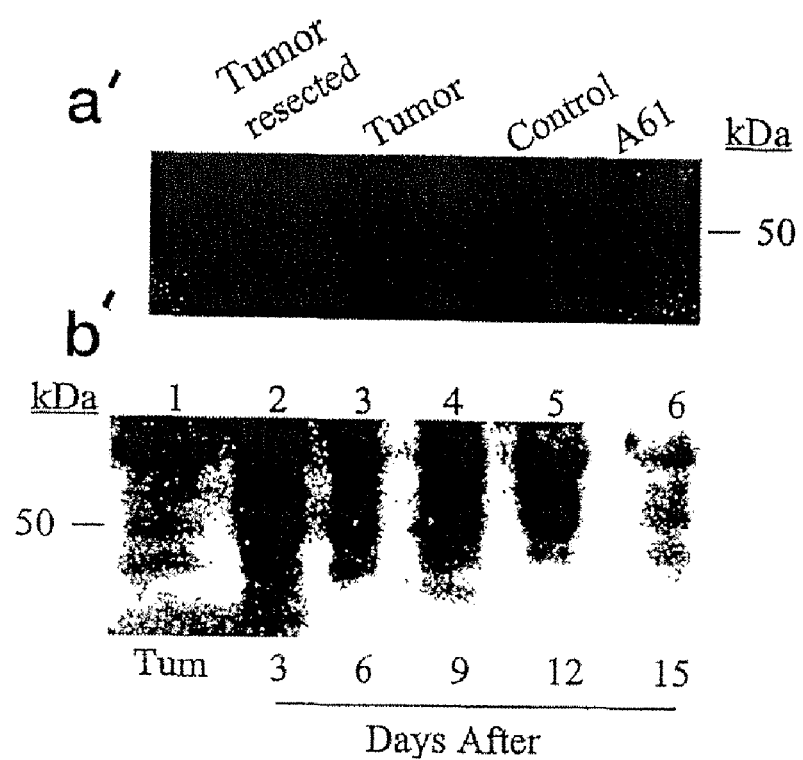
FIG. 6 demonstrates that detectable levels of an $A_{61}$-like plasminogen fragment are present in serum from normal, tumor-bearing, and tumor-resected mice

As shown in FIG. 6, the Western blots presented in FIG. 5A and FIG. 5B demonstrate that the serum from normal, tumor-bearing, and tumor-resected mice all had detectable levels of an $A_{61}$-like plasminogen fragment. In these experiments, the blots were probed with human monoclonal anti-human plasminogen kringle 1-3 antibody (FIG. 6, a') or rabbit anti-mouse angiostatin antibody (FIG. 6, b'). The mouse plasminogen fragment labeled by these antibodies ran with an $M_r$ of about 50,000 on SDS-PAGE under non-reducing conditions and was also detectable with a anti-human kringle 1-3 monoclonal antibody (FIG. 5C, a'). Unlike angiostatin, the $A_{61}$-like protein was present in both normal sera and sera from tumor-bearing animals, and no appreciable change in the concentration of the $A_{61}$-like plasminogen fragment was observed from 3 to 15 days after tumor resection (FIG. 5B, and FIG. 6, b').

Figure 7A:
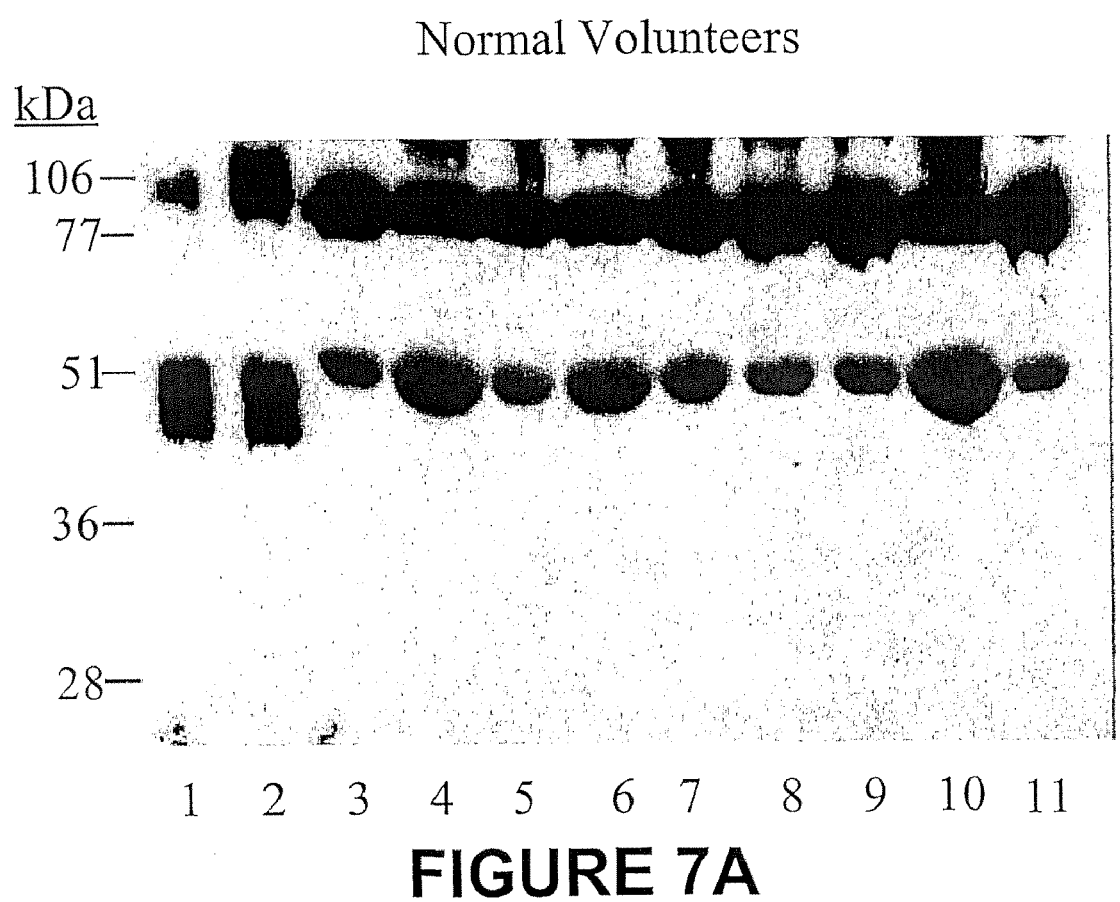
FIG. 7 illustrates a comparison of $A_{61}$ with plasminogen fragments present in sera from normal volunteers (A) or cancer patients (B).
Figure 7B:
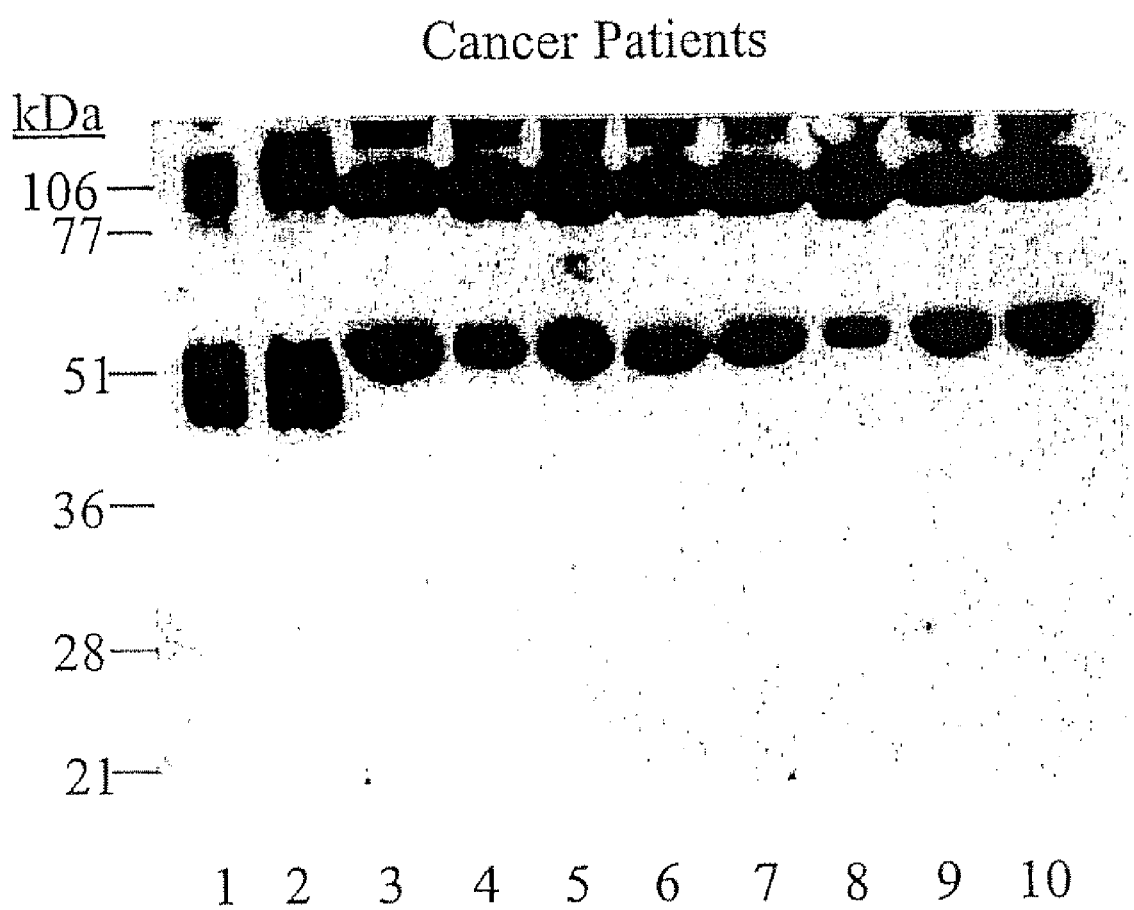

The presence of an $A_{61}$-like protein in the sera of healthy and tumor-bearing mice led to an investigation of the presence of an $A_{61}$-like protein in human subjects. FIG. 7 presents a comparison of $A_{61}$ with plasminogen fragments present in human sera. Frozen human sera from normal volunteers (A) or cancer patients (B) were thawed and then incubated with 50 μl of lysine-Sepharose (equilibrated in 20 mM Hepes (pH 7.4), 140 mM NaCl) for 30 min at room temperature. The matrix was washed with 5 volumes of equilibration buffer, boiled with SDS-PAGE sample buffer, and subjected to non-reduced SDS-PAGE. Western blotting was performed with monoclonal anti-human angiostatin antibody. A, angiostatin (Calbiochem) standard (250 ng) (lane 1); $A_{61}$ standard (250 ng) (lane 2); serum from healthy laboratory volunteers (lanes 3-11). B, angiostatin (Calbiochem) standard (250 ng) (lane 1); $A_{61}$ standard (250 ng) (lane 2); testicular cancer (lane 3); head and neck cancer (lanes 4 and 5); testicular cancer (lanes 6-8); head and neck cancer (lanes 9 and 10).

As shown in FIG. 7, unlike angiostatin, the $A_{61}$-like plasminogen fragment was present in the serum of every individual examined. Because of its presence in the sera of healthy and diseased mice and humans, it is concluded that unlike angiostatin, an $A_{61}$-like plasminogen fragment is a normal component of mammalian serum, and that this fragment can be isolated using the techniques described herein. Without wishing to be bound by theory, it appears that the $A_{61}$-like molecule is produced in the serum simply as a result of plasmin autodigestion. Although the biological activity of serum-derived $A_{61}$-like molecule has not been tested, this serum component can be further isolated using standard techniques of chromatography, such as ligand affinity, gel filtration, ion exchange, reverse-phase, and hydrophobic interaction chromatography.

EXAMPLE 4

This example discloses biochemical and biophysical properties of $A_{61}$.

Because large quantities of $A_{61}$ were easily generated, N-terminal sequence and C-terminal sequence of $A_{61}$ could be determined. Terminal sequences were determined by commercial facilities using standard techniques. N-terminal sequence was determined by Edman degradation, and C-terminal sequences were determined using a Hewlett-Packard HP G1000A C-terminal protein sequencer and an Applied Biosystems 477C Procise C C-terminal sequencer. Consistent results were obtained from the sequencers. The Hewlett-Packard HP G1000A C-terminal protein sequencer utilized chemistry version 2.0 using diphenylphosphorylisothiocyanate as the activating agent (Bailey, J. M. et al. (1992) *Protein Sci.* 1: 1622-1633) and a modified cleavage system using lithium ethiolate as the cleavage agent (U.S. Pat. No. 5,986,071 to Graham et al.). An Applied Biosystems 477C Procise C C-terminal sequencer used standard chemistry as described (Boyd, V. L. (1992) *Analytical Biochemistry* 206: 344-352).

The N-terminal sequence of the $A_{61}$ was determined to be $Lys^{78}$-$Glu^{83}$. Major and minor C-terminal sequences were identified as $Lys^{468}$-$Gly^{465}$ and $Arg^{47}$-$Gly^{467}$, respectively (Table I). Thus, by comparing N- and C-terminal sequences to the known sequence of plasminogen, it was established that the autoproteolytic cleavage sites of plasmin were $Lys^{77}$-$Lys^{78}$, $Lys^{468}$-$Gly^{469}$, and $Arg^{471}$-$Gly^{472}$. Therefore, the major species of $A_{61}$ has the primary amino acid sequence of $Lys^{78}$-$Lys^{468}$, whereas the minor species is $Lys^{78}$-$Arg^{471}$. The average molecular mass predicted from this amino acid sequence is 44.1 kDa.

TABLE I[a]

Amino- and Carboxyl-Terminal Sequence of Human $A_{61}$

| | | | | | | | |
|---|---|---|---|---|---|---|---|
| Plasminogen | $G_{465}$ | $N_{466}$ | $G_{467}$ | $K_{468}$ | $G_{469}$ | $Y_{470}$ | $R_{471}$ |
| $A_{61}$ C-Sequence A | | | G | K | G | Y | R |
| $A_{61}$ C-Sequence B | G | N | G | K | | | |
| Plasminogen | $K_{78}$ | $V_{79}$ | $Y_{80}$ | $L_{81}$ | $S_{82}$ | $E_{83}$ | |
| $A_{61}$ N-Sequence | K | V | Y | L | X | E | |

[a]Human $A_{61}$ was generated from human plasminogen and uPA in the cell-free system as described in the text. The molar ratio of $A_{61}$ C-sequence A and B was 2:5.

N- and C-terminal sequencing has allowed the precise elucidation of the primary structure of $A_{61}$ as comprising the amino acid sequence $Lys^{78}$-$Lys^{468}$. Other A-chain fragments have been reported, but the absence of C-terminal sequencing has made the exact identification of these fragments difficult. Plasminogen is cleaved by a variety of proteinases including metalloelastase, matrix metalloproteinases, and serine proteinases to generate kringle 1-3, kringle 1-4, and kringle 1-4.5 fragments (Table II). Typically these A-chain fragments terminate at amino acid residues in the linker regions between the K3 and K4 (C-terminal Val338/354 residues for kringle 1-3), the linker regions between kringle 4 and kringle 5 (C-terminal Ala440 or Pro446/447 for kringle 1-4), or within residues of kringle 5 (C-terminal Arg530 for kringle 1-4.5). Therefore, $A_{61}$ is a novel A-chain fragment that belongs to the kringle 1-4.5 class of A-chain fragments except that it contains only 7 residues of kringle 5.

TABLE II

Comparison of various A-chain fragments

| Structure | MW (kDa) | Kringles | $IC_{50}$ (nM) | Method of Plasminogen Cleavage | Reference |
|---|---|---|---|---|---|
| Y80 - A440 | 51-54 | K1-4 | 70 | Elastase | (Takada et al., 1988) |
| Y80 -V338/354 | 41-44 | K1-3 | 135 | Elastase | (Takada et al., 1988) |
| N60-P447 | 55 | K1-4 | | MMP-3 | (Lijnen et al., 1998) |
| K78-P447 | 58 | K1-4 | | MMP-7 | (Patterson and Sang, 1997) |
| K78-P446 | 58 | K1-4 | | MMP-9 | (Patterson and Sang, 1997) |
| K78-K468 | 61 | K1-4 + 7rK5 | 35 | Autodigestion | (Kassam et al., 2001) |
| K78-R530 (?) | 66, 60, 57 | K1-4 + 69rK5 | | Plasmin reductase and serine protease | (Stathakis et al., 1999) |
| K78- ? | 50* | K1-4 (?) | 300 | Reduction and Autodigestion | (Gately et al., 1997) |
| K77- ? | 42, 48, 50* | K1-4 (?) | | Autodigestion | (Falcone et al., 1998) |
| K78-R530 | 55 | K1-4 + 69rK5 | 0.050 | Autodigestion at pH 11 | (Cao et al., 1999) |
| L74-L451 | 49, 51* | K1-4 | 17 | Recombinant | (Sim et al., 1997) |
| L74-P349 | 36* | K1-3 | | Recombinant | (MacDonald et al., 1999) |
| unknown | 38 | K1-(?) | | MME | (Dong et al., 1997) |

Abbreviations in Table 2 are as follows: K, kringle; r, amino acid residues; MME, macrophage metalloelastase. Numbering in the Table is based on the sequence of human plasminogen (791 residues) excluding the 19 amino acid signal peptide that ends at Met-19 and beginning at Glu-1 (Forsgren et al., 1987). The molecular weights were determined by reduced SDS-PAGE or non-reduced SDS-PAGE (*). The angiostatin activity of the A-chain fragments, the $IC_{50}$, was determined as the concentration of A-chain fragment required to half-maximally inhibit the proliferation of bovine capillary endothelial cells. To allow a direct comparison of the angiostatin activity, results were pooled from several reports (Cao et al., 1996). The symbol (?) indicates proposed structures that were not confirmed by C-terminal sequencing.

To investigate the possibility of post-translational modifications of $A_{61}$ (in addition to the proteolytic cleavages), the molecular mass of $A_{61}$ was measured by mass spectrometry by the technique of matrix-assisted laser desorption ionization (MALDI) mass spectroscopy. Mass spectra were obtained using a Voyager DE-STR (PE Biosystems) MALDI-time-of-flight mass spectrometer. For this analysis, samples of $A_{61}$ were individually loaded onto pre-equilibrated Zip- Tips (Millipore Corp.) in four 4-μl increments, for de-salting and pre-concentration. The samples were each eluted from their Tip with 2 μl of recrystallized Sinapinic (3,5-dimethoxy-4-hydroxycinnamic acid) matrix solution, 1 μl at a time, onto a 100-well stainless steel sample slide. After introduction of the slide into the mass spectrometer, a linear MALDI method was employed to obtain sample spectra. The method employed a 20-kV accelerating voltage, a nitrogen laser (337 nm, UV wavelength), and a 350-ns extraction delay time. Each data set was noise-filtered, smoothed twice, entroided, and de-isotoped to remove the isotope contributions from the centroided-isoform spectrum. Mass spectrometry of $A_{61}$ revealed a broad cluster of features of about 1-kDa width. The dominant species in the cluster smoothed into a molecular mass of 46,616 daltons when the cluster was centroided and de-isotoped. This measured molecular mass is significantly greater than the average molecular mass of approximately 44.1 kDa predicted from the amino acid sequence. The comparison of the 46.6-kDa fragment of $A_{61}$ derived from mass spectrometric analysis with the 44.5-kDa fragment derived from the amino acid sequence of the protein suggests that like the parent molecule, plasminogen, $A_{61}$ is glycosylated (Hayes, M. L., and Castellino, F. J. (1979) *J. Biol. Chem.* 254: 8772-8776; Hayes, M. L., and Castellino, F. J. (1979) *J. Biol. Chem.* 254: 8777-8780). Plasminogen contains N-linked carbohydrate residues on kringle 3 and two O-linked carbohydrate on Ser249 and Thr346 of the kringle 2-kringle 3 linker and kringle 3-kringle 4 linker, respectively. The role of these glycosylations is unclear, but studies of A-chain fragment glycoforms have suggested that the extent of glycosylation may affect the biological activity or half-life of the protein in circulation (Pirie-Shepherd, S. R. (1999) J. Lab. Clin. Med. 134, 553-560).

A comparison of the amino acid sequence of $A_{61}$ with other A-chain fragments is presented in Table UI. The data presented therein establish that $A_{61}$ is a novel A-chain fragment. The sequence of the molecule indicates that, unlike angiostatin and other plasminogen fragments purported to inhibit endothelial cell proliferation, $A_{61}$ consists of the first four kringles of plasminogen plus the kringle 4-kringle 5 linker region and seven residues of kringle 5.

Figure 8:
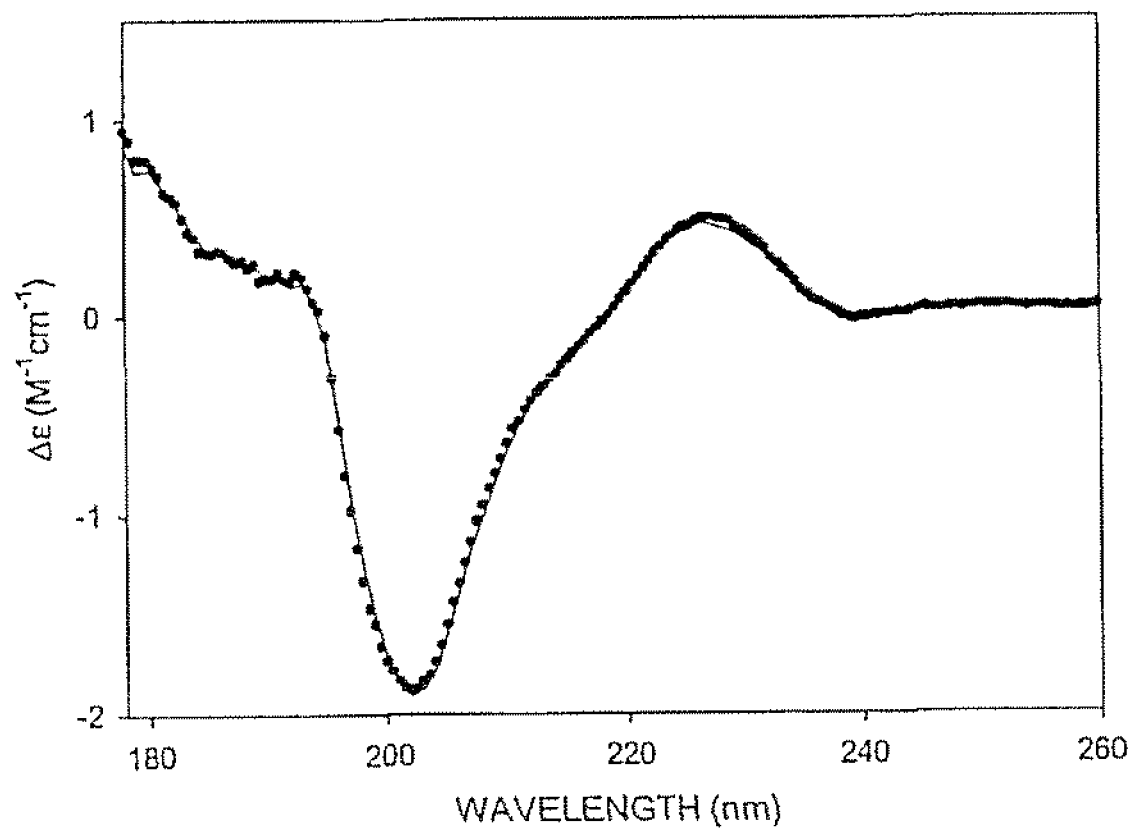
FIG. 8 illustrates the circular dichroism spectrum of $A_{61}$.

The availability of large amounts of $A_{61}$ enabled an investigation of the secondary structure of $A_{61}$. For this purpose, a circular dichroism spectrum was obtained from samples of the molecule (FIG. 8). Circular dichroism (CD) measurements were performed with a Jasco J-810 spectropolarimeter. The spectropolarimeter was calibrated with an aqueous solution of recrystallized ammonium d-10-camphorsulfonate. $A_{61}$ (0.4-0.6 mg/ml) was incubated in 10 mM Tris-HCl (pH 7.5) and 150 mM NaCl in the presence or absence of ligand for 20 min at room temperature. Samples (0.1 ml) were scanned in a quartz cuvette (0.5-mm path length) from 178 to 260 nm at a rate of 20 nm/min, using a bandwidth of 1 nm and a response time of 4 sec. CD spectra of proteins were obtained by averaging three wavelength scans and were corrected by subtracting buffer scans or, where appropriate, scans of ligand in buffer. Results are expressed as $\Delta\epsilon_{(M-1-cm-1)}$. The $A_{61}$ secondary structure content was assessed with the program CDsstr version 1.8 (Johnson, W. C. (1999) *Proteins* 35: 307-312).

The far-UV circular dichroism spectrum of $A_{61}$ exhibited a strong negative band at 202 nm and a weak positive band at about 227 nm. This spectrum is similar to that reported for other kringle containing A-chain fragments such as kringle 4 (Cleary, S., et al. (1989) *Biochemistry* 28: 1884-1891; Castellino, F. J., et al. (1986) *Arch. Biochem. Biophys.* 247: 312-320; Misselwitz, R., et al (1994) *Int. J. Biol. Macromol.* 16: 187-194.). Analysis of the secondary structure content from CD spectra yields about 21%-strand, 14%-turn, 18% 31-helix, 8% 310-helix, and 40% unordered. Similar to other kringle-containing structures, $A_{61}$ does not contain any α-helix structure. These results establish that the $A_{61}$ generated in the cell-free system in the absence of a sulfhydryl donor did not result in the denaturation of the molecule.

FIG. 8 shows the CD spectrum of $A_{61}$. Wavelength scans were conducted at 20° C. in 10 mM Tris (pH 7.5), 150 mM NaCl. The protein concentration of $A_{61}$ was 8.5 μM. The line through the points represents the best fit for the data reconstructed from the average of the calculated combinations of secondary structure content.

The absence of •-helical structure in $A_{61}$ was indicated from analysis of the far-TV CD spectrum using CDsstr, a recently released computer program (Johnson, W. C. (1999) *Proteins* 35: 307-312). Overall, the secondary structure of $A_{61}$ is comparable to other kringle-containing proteins. Recently, it was demonstrated that kringle-containing proteins contain significant $3_1$-helix. This structure was not reported in earlier x-ray structures because of the difficulty in visualization. However, the far-UV CD spectrum is uniquely sensitive to $3_1$-helix. The presence of $3_1$-helix in $A_{61}$ is consistent with the $3_1$-helix structures recently reported for other kringle-containing structures such as plasminogen (Marti, D. N., et al., (1999) *Biochemistry* 38: 15741-15755). Since the intrinsic fluorescence emission spectrum of $A_{61}$ increased in the presence of lysine or lysine analogues, we have concluded that the kringles of $A_{61}$ are functionally active.

Intrinsic fluorescence spectroscopy was used to investigate the function of the kringles of $A_{61}$. Excitation and emission spectra were collected with a Perkin-Elmer Life Sciences LS 50B fluorescence spectrometer equipped with a constant temperature cell holder. The excitation and emission slit widths were set to 5 and 10 nm, respectively. The spectra were collected at 25° C. with $A_{61}$ (3.7 μM) in a buffer consisting of 20 mM Hepes (pH 7.4) and 140 mM NaCl and in the presence or absence of ligand. The data were corrected for the slight dilution consequent to ligand additions.

Figure 9:
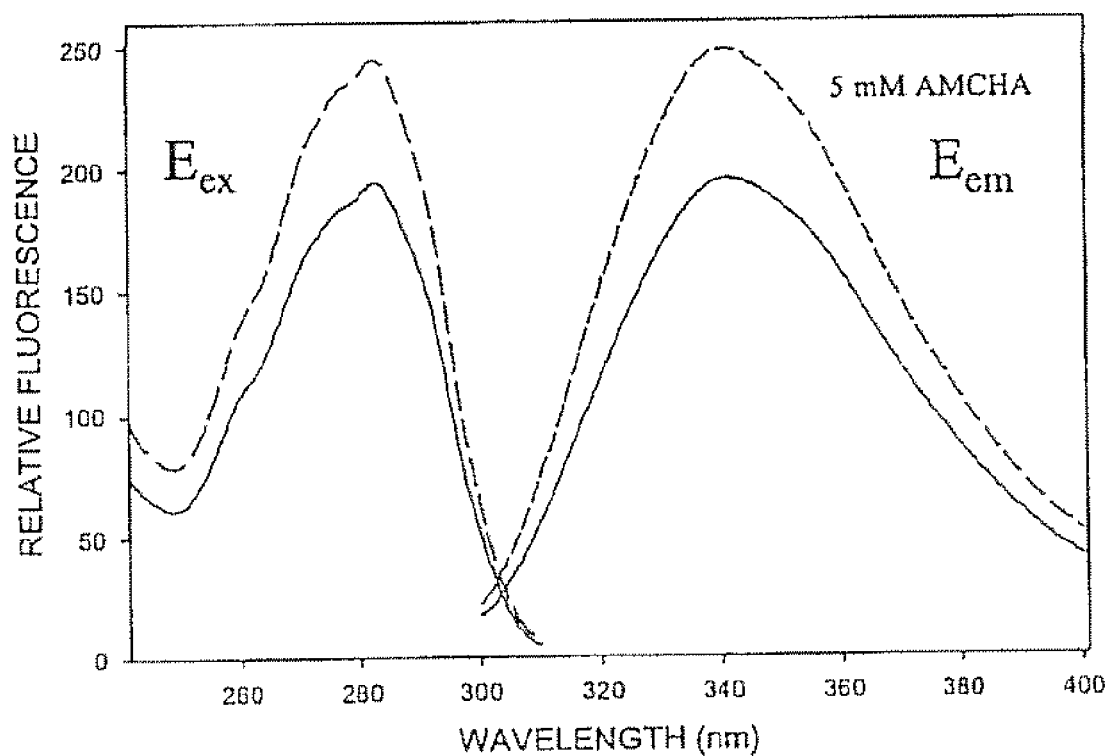
FIG. 9 illustrates the intrinsic fluorescence spectra of $A_{61}$ in the absence and presence of Trans-4-aminomethylcyclohexanecarboxylic acid (AMCHA).

FIG. 9 shows the intrinsic fluorescence spectra of $A_{61}$ in the absence and presence of Trans-4-aminomethylcyclohexanecarboxylic acid (AMCHA). The excitation $E_x$ and emission $(E_m)$ spectra of ligand-free (solid line) and AMCHA-saturated $A_{61}$ (dotted line) are presented. The spectra were measured at 20° C. in 20 mM Hepes (pH 7.4) and 140 mM NaCl. The concentration of the $A_{61}$ was 3.7 μM.

The binding of lysine-type zwitterions such as F-amino-n-caproic acid to the kringles of plasminogen is known to result in an increase of about 7% in the intrinsic protein fluorescence (Violand, B. N., et al. (1978) *J. Biol. Chem.* 253: 5395-5401). $A_{61}$ was therefore examined for shifts in intrinsic fluorescence spectra resulting from contact with potential ligands. FIG. 8 presents the excitation and emission intrinsic fluorescence spectra for $A_{61}$. The excitation and emission maxima were 283 and 342 nm, respectively. The binding of lysine and other lysine analogues such as F-amino-n-caproic acid and N-acetyl-L-lysine (which mimics the structure of a C-terminal lysine) caused a significant increase in the intrinsic fluorescence emission spectra. AMCHA caused the largest increase (27%) in fluorescence intensity of the emission spectra. However, N-acetyl-L-lysine methyl ester, a lysine analogue that mimics the structure of an internal lysine residue, did not cause a significant change in the fluorescence emission spectra. These data are summarized in Table III. Because the intrinsic fluorescence emission spectrum of $A_{61}$ increased in the presence of lysine or lysine analogues, the kringles of $A_{61}$ are functionally active and can bind to free lysine residues or C-terminal lysine residues but not to internal lysine residues.

EXAMPLE 5

This example illustrates the biological properties of $A_{61}$.

To examine the effects of $A_{61}$ on endothelial cell growth, bovine capillary endothelial (BCE) were contacted with $A_{61}$. For these experiments, cells were grown in DMEM (JRH Biosciences) supplemented with 10% calf serum, 2 mM L-glutamine, 10 units/ml penicillin G, 10 µM streptomycin sulfate, and 3 ng/ml basic fibroblast growth factor (bFGF; Calbiochem). Cells between passages 3 and 5 were then plated into 24-well tissue culture plates (3,000 cells/well) and incubated at 37° C. for 24 h. The medium was then replaced with fresh DMEM containing 5% calf serum in the presence or absence of $A_{61}$ (generated by the cell-free method) which had been applied to a Detoxi-Gel column (Pierce) to remove endotoxin immediately prior to use. (Endotoxin levels were determined to be less than 45 pg endotoxin per ml (0.4 Endotoxin Units/ml) by the Pyrotell Limulus amoebocyte lysate assay (Associates of Cape Cod, Inc., Falmouth, Mass.)). After a 30-min incubation of the cells in the presence of $A_{61}$, bFGF was added to a final concentration of 1 ng/ml, and cells were further incubated for 72 h. The cells were trypsinized, resuspended in Isoton II (Beckman), and counted with a Coulter counter.

$A_{61}$ inhibited BCE cell growth in a dose-dependent manner when the effects of $A_{61}$ on endothelial cell proliferation were assayed by this method (FIG. 9). The concentration of $A_{61}$ generated from plasminogen required for 50% inhibition was about 35±10 nM (mean±S.D., n=4) for $A_{61}$ prepared in the absence of an exogenous sulfhydryl donor. Maximum inhibition of proliferation of the BCE cells was observed at an $A_{61}$ concentration of about 200 nM. The potency of $A_{61}$ prepared in the presence of the sulfhydryl donor N-acetyl cysteine was identical. However, the $IC_{50}$ of 35 nM is significantly lower than the $IC_{50}$ of 300 nM reported by Soff and co-workers (Gately, S., et al., (1997) Proc. Natl. Acad. Sci. U.S.A. 94, 10868-10872), and thereby represents a significant improvement. Concentrations of $A_{61}$ as high as 2 µM did not inhibit the proliferation of several nonendothelial cell lines such as HT1080 fibrosarcoma cells, HeLa cells, and 293 cells.

Figure 10:
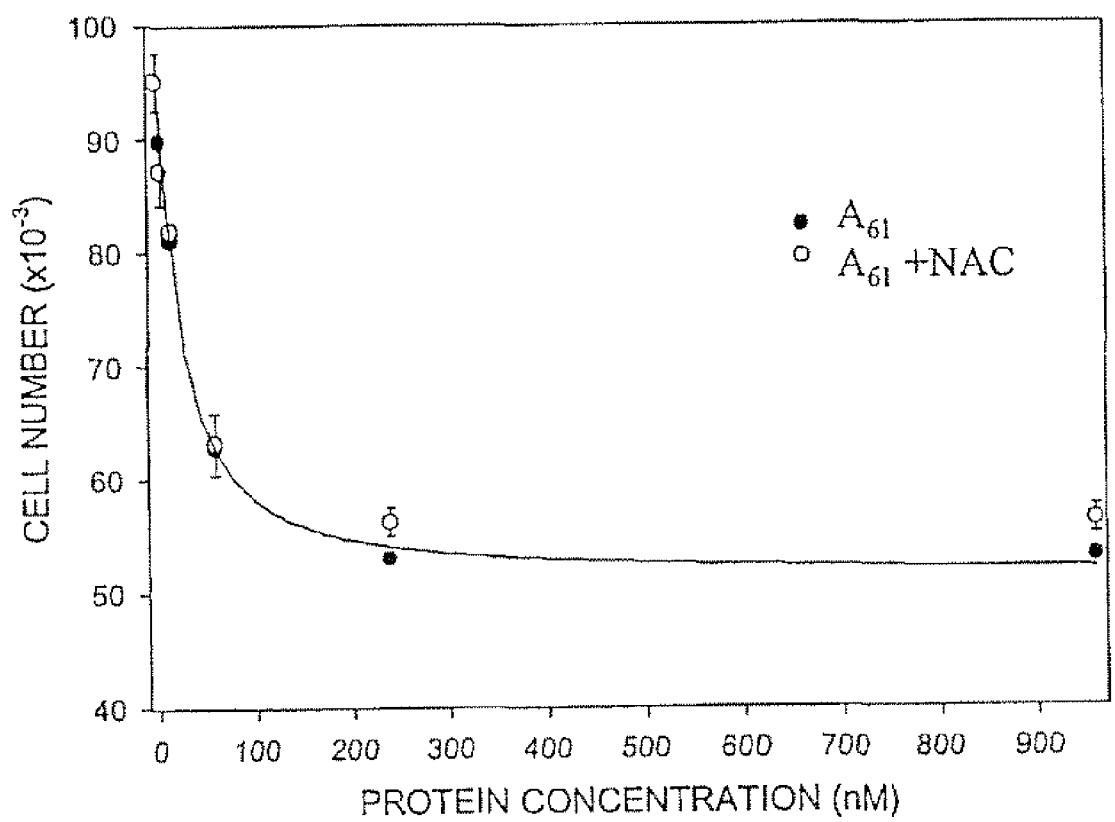
FIG. 10 illustrates the inhibition of bovine capillary endothelial cell proliferation by $A_{61}$.

FIG. 10 shows the biological activity of $A_{61}$. A, inhibition of bovine capillary endothelial cell proliferation. BCE cells were incubated with 1 ng/ml bFGF and various concentrations of $A_{61}$ which was prepared in the presence (open circles) or absence (closed circles) of the sulfhydryl donor N-acetyl cysteine. After 72 hours of incubation, the cells were trypsinized, resuspended in Isoton II solution, and counted with a Coulter counter. B, inhibition of metastatic tumor growth in vivo. Mice were injected intraperitoneally with phosphate-buffered saline (PBS) or $A_{61}$ (in PBS) (2.5 mg/kg/day) immediately after removal of the primary tumor. The lungs were removed at specific intervals, and the lung weights were compared.

Anti-tumor activity of $A_{61}$ in vivo was investigated using a Lewis Lung Carcinoma assay (U.S. Pat. No. 5,776,704 to O'Reilly et al). Lewis lung carcinoma cells were grown, harvested at log phase, and resuspended in PBS. Approximately $10^6$ cells were injected subcutaneously in the middle dorsum of 6-8-week-old C57BL/6 male mice. When tumors reached 1500 mm³ in size (about 14 days after implantation), the mice were randomly separated into two groups. The first group underwent surgical removal of the tumor, and the second group was subjected to a sham surgical procedure in which tumors were manipulated but were left intact. Animals from the tumor-resected group were randomly placed into test and control groups. The test group of mice received daily intraperitoneal injections of $A_{61}$ in PBS (dose=2.5 mg/kg/day), whereas the control group received PBS alone. Every 3rd day after tumor resection, mice were sacrificed, and the lungs were weighed.

Figure 11:
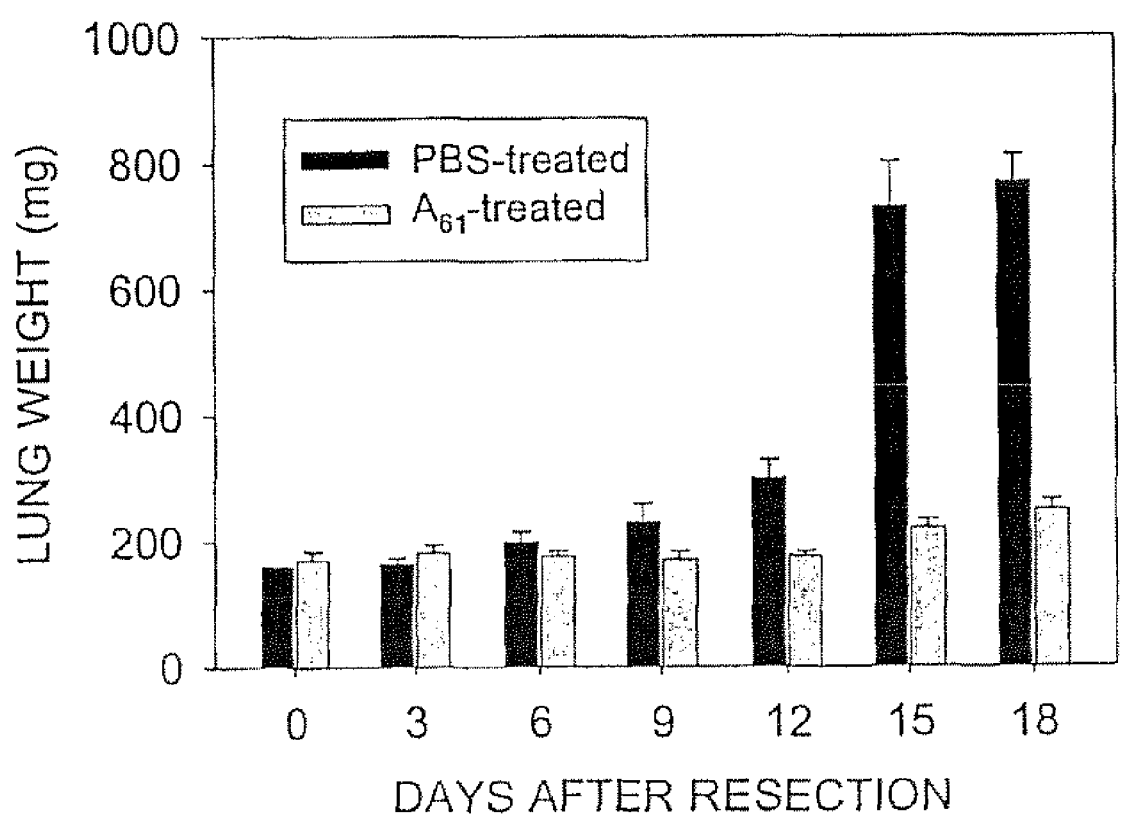
FIG. 11 illustrates the inhibition of metastatic tumor growth by $A_{61}$ in mice injected subcutaneously with Lewis lung carcinoma cells as measured by Lung weight over time.

The lung weight of the PBS-treated, tumor-resected mice increased over time (FIG. 11). Eighteen days after the tumor resection, lung weight, which correlated with total tumor burden, reached 770±42 mg (n=4). In contrast, the average lung weight of the mice that received daily doses of $A_{61}$ increased only to 250±14 mg (n=4). The average weights of lungs of normal and 18-day tumor-bearing mice were 191±25 (n=4) and 199±20 mg (n=4), respectively. The increase in the weight of the lungs in the tumor-resected mice corresponded with an increase in the number of observable metastatic foci. These results establish that $A_{61}$ is a potent anti-tumor agent. While not wishing to be limited by theory, it is believed that the anti-tumor activity is due to the anti-endothelial cell proliferation activity of $A_{61}$, which manifests as anti-angiogenic activity in vivo. The dosage of 2.5 mg/kg/day which provided for anti-tumor activity is significantly lower than the 15 mg/kg/day used by Soff and co-workers (Gately, S., et al., (1997) Proc. Natl. Acad. Sci. U.S. A. 94, 10868-10872). The increased potency of $A_{61}$ as an anti-tumor agent thereby represents a significant improvement over other anti-angiogenic plasminogen derivatives.

EXAMPLE 6

This example illustrates the generation of p22 from $A_{61}$ using cell-free method.

An emerging concept in biology is that certain inactive precursor proteins are cleaved in vivo to produce biologically active fragments. For example, the serine protease kallikrein proteolyses kininogen resulting in the release of bradykinin, a potent vasodilator (Schmaier, 2000 *Curr. Opin. Hematol.* 7:261-265.). Similarly, the proteolysis of collagen XVIII results in the generation of endostatin, a potent anti-angiogenic protein (O'Reilly et al., 1997 *EXS* 79:273-294). This concept of bioregulatory proteolysis is dramatically illustrated for plasminogen where the proteolytic cleavage of the molecule can produce either the broad spectrum protease, plasmin or upon further cleavage, anti-angiogenic plasminogen fragments. Although many different plasminogen fragments have been produced in vitro by the proteolytic digestion of plasmin(ogen) or by recombinant technology, it has been unclear what anti-angiogenic plasminogen fragments are produced under physiological conditions. Known anti-angiogenic plasminogen fragments all comprise at least one kringle domain.

Kringle domains are small protein domains that consist of about eighty amino acids and have a characteristic three disulfide-bonded structure. These domains appear to be independently folded units that have been defined structurally to have a cysteine residue at their N- and C-terminus. The kringle domains appear singly in urokinase (Gunzler et al., 1982 *Hoppe Seylers. Z. Physiol. Chem.* 363:1155-1165.) and factor XII (McMullen and Fujikawa, 1985 *J. Biol. Chem.* 260:5328-5341), twice in tissue-type plasminogen activator and prothrombin (Pennica et al., 1983), four times in hepatocyte growth factor (Tashiro et al., 1990 *Proc. Natl. Acad. Sci. U.S.A.* 87:3200-3204), five times in plasminogen and about forty times in apolipoprotein(a) (McLean et al., 1987 *Nature* 330: 132-137; Castellino and McCance, 1997 *Ciba Found. Symp.* 212:46-60.; Castellino and Beals, 1987 *J. Mol. Evol.*

26:358-369). One of the key structures within a kringle is its lysine-binding site. In general, the lysine-binding site of a kringle interacts with the C-terminal lysine residue of the target protein. For example, the kringle domains of plasminogen are presumed to interact with fibrin by binding to an exposed lysine side chain. Furthermore, the kringle domains of plasminogen bind to the cell surface via their binding to the C-terminal lysines of receptor proteins such as annexin II tetramer or to their major plasma inhibitor, $\alpha_2$-antiplasmin (Kassam et al., 1998 *Biochemistry* 37:16958-16966; Longstaff and Gaffney, 1991 *Biochemistry* 30:979-986; Christensen et al., 1996 *FEBS Lett.* 387:58-62). There is also evidence that the kringles are capable of mediation of intramolecular interactions by interacting with intra-chain lysine residues (Ryan and Keegan, 1985 *Biochim. Biophys. Acta* 830:187-194; Menhart et al., 1995 *Biochemistry* 34:1482-1488.; McCance and Castellino, 1995 *Biochemistry* 34:9581-9586; Takada et al., 1993 *Thromb. Res.* 50:285-294).

The plasminogen kringles have been extensively studied. These structures have 48-50% identity but are not functionally equivalent. For example, the binding affinities of the kringles for N-acetyl-L-lysine, which models the structure of a C-terminal lysine is in order of decreasing affinity is kringle 1>kringle 4>kringle 2. Kringle 5 only weakly binds this lysine analogue while kringle 3 is incapable of binding (Marti et al., 1997). Interestingly, kringle 1, kringle 2, kringle 4 and kringle 5 have similar affinity for lysine analogues that mimic an intra-chain lysine (Marti et al., 1997 *Biochemistry* 38:15741-15755.). The plasminogen kringles may have distinct binding partners. Kringle 2 exclusively binds to intra-chain lysines of the group A streptococcal surface protein, PAM (Marti et al., 1997 *Biochemistry* 38:15741-15755). Likewise, kringle 4 exclusively interacts with the C-terminal lysine residue of alpha2-antiplasmin (Christensen et al., 1996 *FEBS Lett.* 387:58-62).

The present inventors have found cancer and normal cells can convert plasminogen into a novel 22 kDa fragment having anti-tumor activity, p22. p22 is the smallest plasminogen fragment shown to be generated under physiological conditions. Since p22 contains only a single kringle domain, an important benefit of this invention is its simple structure of short amino acid sequence and lack of glycosylation, both of which facilitate further Investigation and production. To date, p22 is the smallest plasminogen fragment that has been shown to be generated under physiological conditions. Since p22 contains only a single kringle domain, future structure-function analysis of the anti-proliferative activity of this protein will be simpler that similar studies of the multiple kringle-containing plasminogen fragments such as $A_{61}$. The kringle regions of plasminogen have been expressed as recombinant proteins it has been possible to compare their biological activities with that of p22. The individual plasminogen kringle domains have distinct anti-proliferative activities as measured by the endothelial cell proliferation assay. K5, K1 and K3 exhibit potent inhibitory activity, K2 displays weaker activity while K4 is an ineffective inhibitor (Cao et al 1996., *J. Biol. Chem.* 271: 29461-29467; Cao et al., 1997 *J. Biol. Chem.* 272: 22924-22928.). These kringles also have discrete inhibitory functions on endothelial cell migration with K5 and K4 showing potent activity and K2 and K3 showing lesser inhibitory activity and K1 showing negligible activity (Ji et al., 1998 *Biochem Biophys Res Commun* 247: 414-419; Ji et al., 1998 *FASEB J.* 12:1731-1738.). Interestingly, while the structural integrity of the kringles appears to be necessary for their inhibitory activities the lysine binding site of the kringle does not appear to be involved in their inhibitory activity (Ji et al., 1998 *Biochem Biophys Res Commun* 247:414-419; Cao et al., 1996 *J. Biol. Chem.* 271: 29461-29467).

To generate p22 in a cell-free system, $A_{61}$ (7•M) generated using the cell-free system was incubated with 0.1•M of plasmin and buffer containing 20 mM Hepes (pH 7.4), 140 mM NaCl and 100 μM of dithiothreitol for 2 h at 37° C. The reaction was stopped by adding 1 mM Pefabloc (Roche) and the mixture loaded onto a L-lysine-Sepharose column previously equilibrated with equilibration buffer comprising 20 mM Hepes pH7.4 and 140 mM NaCl. The flow-through fraction collected from the lysine-Sepharose column was loaded onto an octyl-Sepharose resin previously equilibrated with 20 mM Hepes (pH7.4) and 4M NaCl. The flow-through fraction collected from the octyl-Sepharose chromatography yielded milligram quantities (as determined using ultraviolet absorbance as described in Example 1) of an isolated protein having an $M_r$ of 22,000 as determined by SDS-PAGE conducted under reducing conditions as described in Example 1. The isolated protein, named p22, was dialyzed against 20 mM Hepes (pH 7.4) and 20 mM NaCl. The dialyzed p22 protein was aliquoted and stored at −70° C. until subsequent use.

Figure 12:
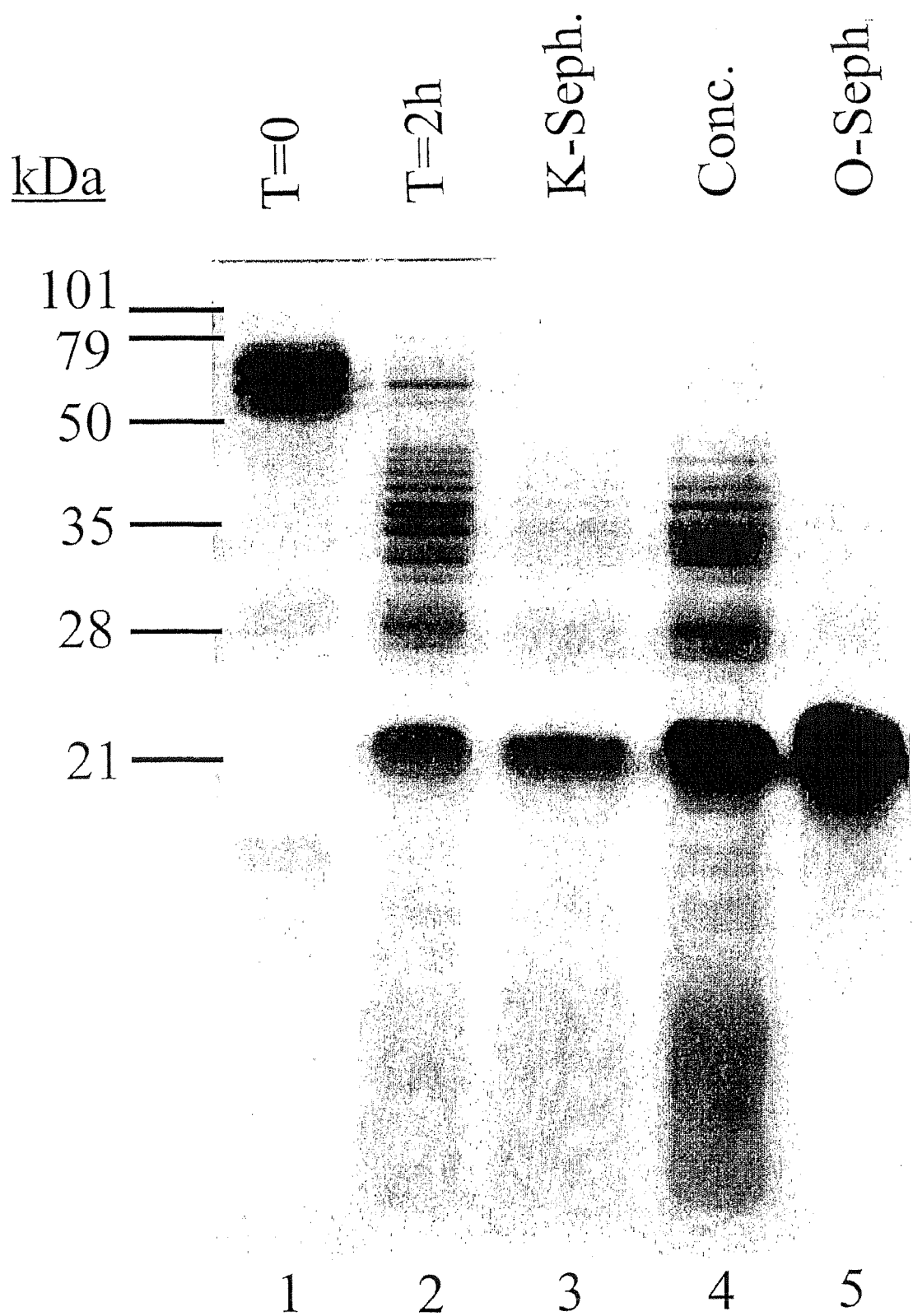
FIG. 12 illustrates the generation of p22 in a cell-free system.

FIG. 12 shows the generation of p22 in a cell-free system. $A_{61}$ (lane 1) was incubated with plasmin (0.1 μM) and dithiothreitol (100 μM) at 37° C. for 2 hours (lane 2). p22 was purified by L-lysine-Sepharose column chromatography (lane 3), concentrated (lane 4), and further purified by octyl-Sepharose column chromatography (lane 5). Samples were subjected to SDS-PAGE, and protein bands were visualized after staining with Coomassie blue.

EXAMPLE 7

This example illustrates the generation of p22 by contacting $A_{61}$ with cells in vitro.

To generate p22 with the aid of cells, human HT1080 cells were maintained in DMEM (GIBCO-BRL) supplemented with 10% heat-inactivated fetal bovine serum, 10 units/ml penicillin G, and 10 μM streptomycin sulfate. Approximately $1 \times 10^5$ cells in 1 ml were added to each well of 24-well tissue culture plates and incubated at 37° C. for about 24 hours, whereby cell monolayers were formed. The cell monolayers were then washed three times with DMEM, and 0.5-8 μM [Glu]-plasminogen in DMEM was added to each well. After about 18 hours of incubation, the medium was removed and diluted with SDS-PAGE sample buffer with β-mercaptoethanol present as reducing agent, and subjected to SDS-PAGE and Western blot analysis as described in Example 1.

When a monoclonal antibody against human plasminogen kringles 1-3 was used as the primary antibody on the Western blot, a protein having an $M_r$ of about 22,000 was detected. Furthermore, upon varying the concentration of plasminogen added to the cells, the amount of p22 varied in a dose-dependent manner. The generation of p22 was observed at plasminogen concentrations as low as 1 μM, i.e., at approximately the physiological concentration of circulating plasminogen. Similar results were obtained when [Lys]-plasminogen was substituted for [Glu]-plasminogen. Other cells, such as BCE cells and HeLa cells also converted plasminogen to p22. However, human umbilical vein endothelial cells (HUVECs) did not generate detectable p22 under the same experimental conditions. Furthermore, based on its mobility in SDS-PAGE under reducing conditions, p22 is slightly larger than recombinant kringle 1 (rK1) of human plasminogen, yet smaller than the $M_r$ of 38,000 or 25,000 determined for recombinant kringle 1-3 or recombinant kringle 2-3, respectively (Rejante, M. R. and Llinas, M. (1994) *European Journal of Biochem-* istry 221: 939-49; An, S. S. et al., (1998) *Protein Sci.* 7: 1947-1959). It is therefore concluded that p22 is a novel plasminogen fragment comprising a single kringle domain.

FIG. 13 shows the identification of a novel plasminogen fragment (p22) produced by HT-1080 cells. (A) HT1080 cells were incubated with DMEM containing the indicated concentrations of [Glu]plasminogen. After an overnight incubation, the medium was analyzed by 15% reduced SDS-PAGE followed by Western blotting with a monoclonal antibody against human plasminogen kringle 1-3 antibody. [Glu]plasminogen (8 µM) after overnight incubation in the absence of cells (lane 1), and A61 standard (lane 7). The HT1080 cells were incubated with the following concentrations of [Glu] plasminogen: 0.5 µM (lane 2); 1 µM (lane 3); 2 µM (lane 4); 4 µM (lane 5); 8 µM (lane 6). (B) HT1080 cells were incubated with DMEM containing the indicated concentrations of [Lys]plasminogen as indicated in (A). (C) HT1080 cells (lane 5), BCE cells (lane 6), or HUVECs (lane 7) were incubated with DMEM containing 8 µM [Glu]plasminogen, and after an overnight incubation the medium was subjected to SDS-PAGE under reducing conditions in a 12.5% gel, followed by Western blotting using a monoclonal antibody against human plasminogen kringle 1-3. [Lys]plasminogen was used in the case of HeLa cells (lane 8). The following standards are also shown: plasminogen (lane 1); A61 (lane 2); p22 (lane 3); recombinant kringle 1 (lane 4).

EXAMPLE 8

This example discloses biochemical and biophysical properties of p22.

In order to identify the region of plasmin(ogen) that was cleaved to produce p22, HT1080 cell-generated p22 was subjected to N-terminal sequence analysis using Edman degradation. The N-terminus of p22 corresponded to $Lys^{78}$ of plasminogen. However, since p22 is larger than the kringle 1 of plasmin(ogen) (FIG. 12), it was concluded that p22 consists of kringle 1 of plasmin(ogen) and additional residues that form the link between the first and second kringles of plasmin(ogen).

p22 generated using the cell-free system was subjected to N-terminal sequence analysis by the methods presented for $A_{61}$ above. This analysis revealed that its N-terminal amino acid of p22, like $A_{61}$, is also $Lys^{78}$ as shown in Table IV. Human P22 was generated from human anti-angiogenic plasminogen fragment, $A_{61}$ and uPA in the cell-free system as described above.

TABLE IV

Amino- and Carboxyl-Terminal Sequence of Human p22

| Plasminogen | $G_{176}$ | $K_{177}$ | $I_{178}$ | $S_{179}$ | $K_{180}$ | $T_{181}$ |
|---|---|---|---|---|---|---|
| P22 C-Sequence | | K | I | S | K | |
| Plasminogen | $K_{78}$ | $V_{79}$ | $Y_{80}$ | $L_{81}$ | $S_{82}$ | |
| P22 N-Sequence | K | V | Y | L | S | |

Furthermore, p22 produced by incubation of plasminogen with HT1080 cells is indistinguishable by SDS-PAGE from p22 produced using the cell-free system (FIG. 12). C-terminal sequence analysis, performed as described for $A_{61}$ above, revealed that the C-terminus of p22 generated by plasminogen/cell contact or by using the cell-free system is $Lys^{180}$. Thus, p22 is a novel plasminogen fragment extending between $Lys^{75}$ and $Lys^{50}$, and is therefore composed of six N-terminal residues, plasminogen kringle 1, three residues of the kringle 1-kringle 2 linker region, and 15 residues of kringle 2.

Figure 14:
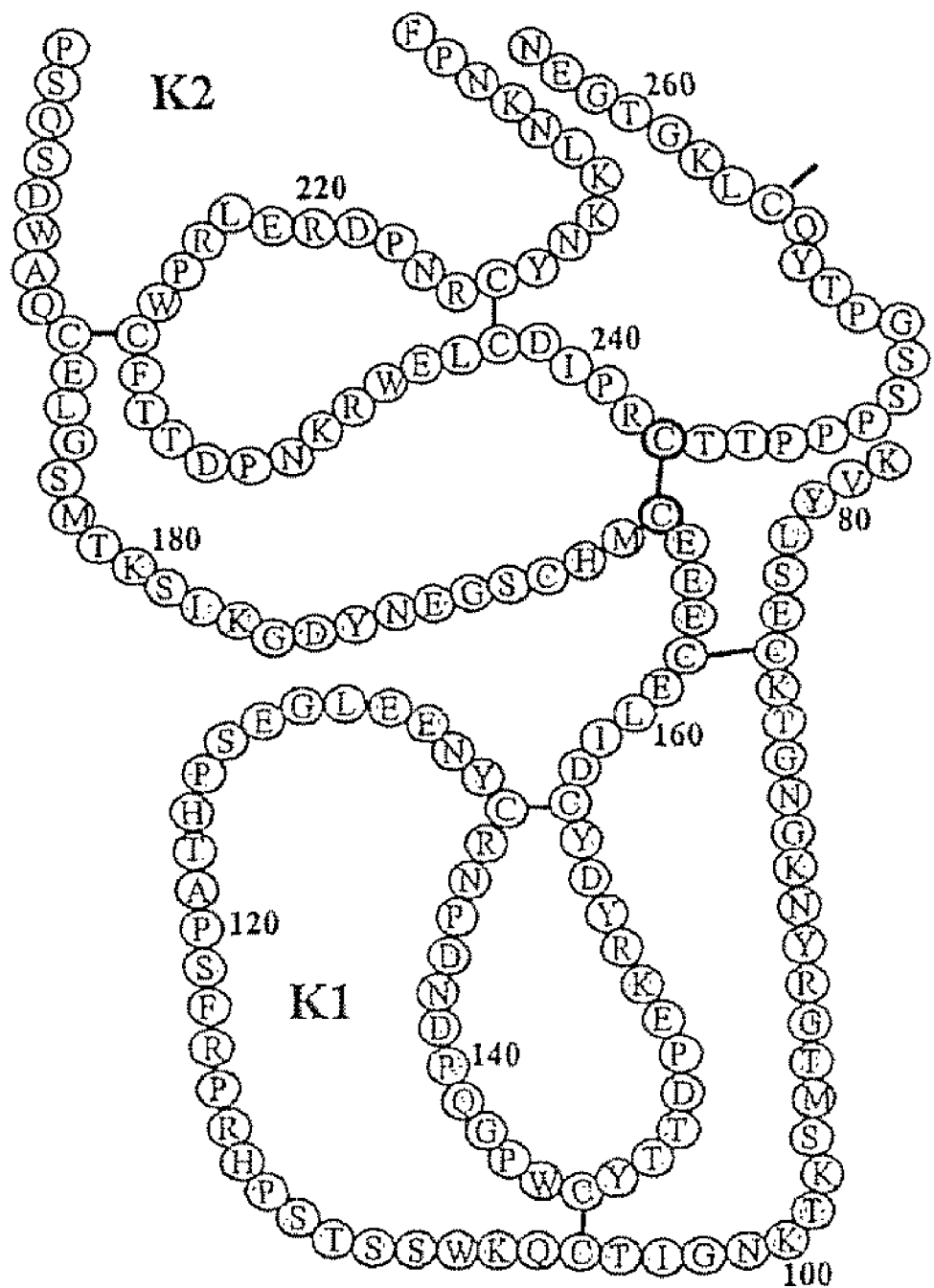
FIG. 14 is a diagrammatic illustration of the structure of p22.

FIG. 14 is a diagrammatic illustration of the structure of p22. The amino acids are indicated using single-letter abbreviations. The shaded region represents the structure of p22.

The amino acids, the 3 letter abbreviations and single letter abbreviations are as follows: alanine—ala—A; arginine—arg—R; asparagine—asn—N; aspartic acid—asp—D; cysteine—cys—C; glutamine—gln—Q; glutamic acid—glu—E; glycine—gly—G; histidine—his—H; isoleucine—ile—I; leucine—leu—L; lysine—lys—K; methionine—met—M; phenylalanine—phe—F; proline—pro—P; serine—ser—S; threonine—thr—T; tryptophan—trp—W; tyrosine—tyr—Y; valine—val—V.

Mass spectrometry analysis conducted on p22 and recombinant kringle 1 (rK1, a single kringle-comprising fragment of plasminogen, obtained as a gift from Dr. M Llinas, Carnegie Mellon University) by the methods presented for $A_{61}$ in Example 4 revealed that p22 is not glycosylated. The predicted size of p22 calculated from its amino acid sequence is $M_r$ 11,825. In comparison, the molecular weight of p22 as measured using mass spectrometry as described in Example 4 is $M_r$ 11,821. The similarity of the molecular weight of p22 calculated from the amino acid sequence with that of the molecular weight derived from mass spectrometry rules out the possibility of glycosylation or other post translational modifications of p22. By contrast, the $M_r$ of rK1 was 9926 as calculated from the amino acid composition and 9815 by mass spectroscopy. This difference in predicted vs. measured size indicates that recombinant kringle 1 is structurally distinct from p22.

In order to examine the secondary structure of p22 (and rK1 for comparison), Circular dichroism (CD) spectra were obtained as described in Example 1. The CD spectrum of p22 showed a positive band at 227.5 nm and strong negative band at 202.7 nm, which is characteristic of a protein devoid of α-helical structure. The negative ellipticity near 200 nm is consistent with the presence of poly(pro)II helices (31 helices) within the secondary structure of p22. Estimation of the secondary structure content of p22 by the variable selection method (Johnson, W. C. (1999) *Proteins* 35: 307-312) suggested that p22 was composed of approximately 17% 31 helix (Table IV). In contrast, recombinant kringle 1 exhibited a positive band at 227.5 nm and a strong negative band at 197.4 nm.

TABLE V

Comparison of the secondary structure of p22 and K1

| Structure | P22 | K1 |
|---|---|---|
| helix | 0 | 3 |
| $3_{10}$ Helix | 3 | 3 |
| sheet | 21 | 25 |
| -turns | 15 | 7 |
| $3_1$ Helix | 17 | 19 |
| unordered | 43 | 24 |

Figure 15:
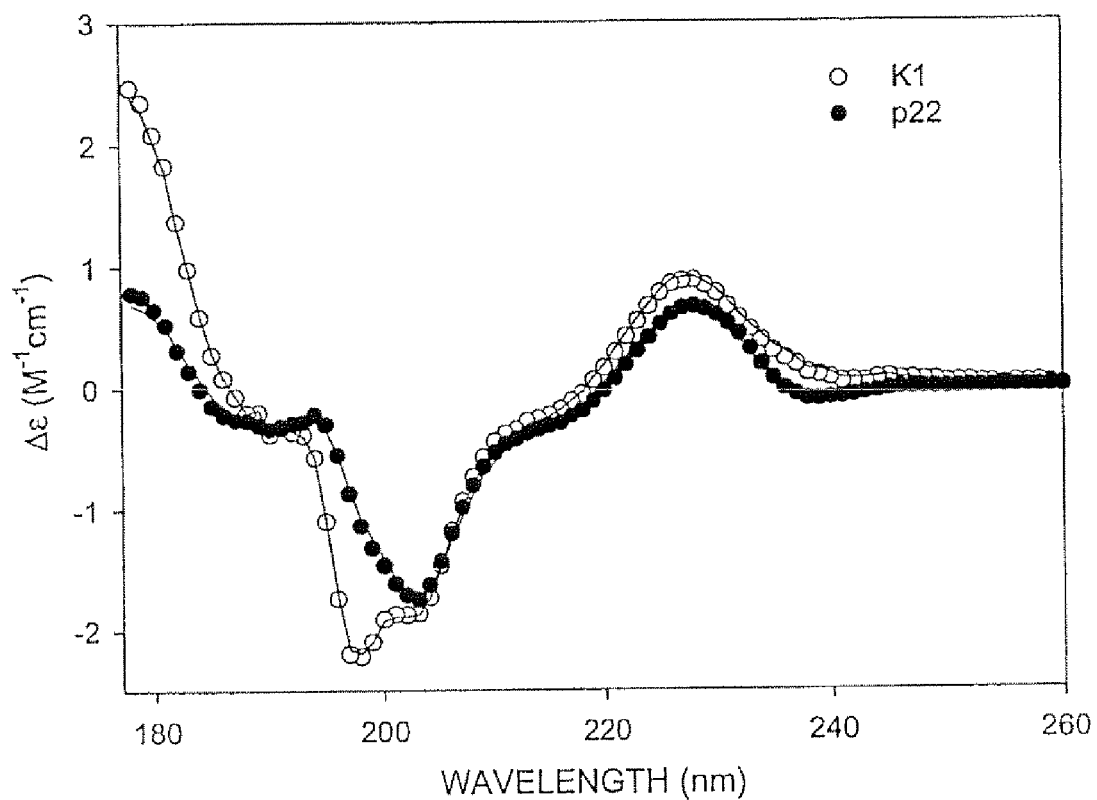
FIG. 15 illustrates the circular dichroism spectra of p22 and kringle 1 (K1).

FIG. 15 presents the CD spectrum of p22 and K1. Wavelength scans were conducted at 20° C. in 10 mM Tris (pH 7.5), 150 mM NaCl. The concentration of p22 and K1 were 41 µM and 25 µM respectively. The line through the points represents the best fit for the data reconstructed from the average of the calculated combinations of secondary structure content.

Intrinsic fluorescence spectroscopy was used to investigate the function of the kringle of p22. Intrinsic fluorescence spectra for p22 and rK1 were obtained as described in Example 1. The intrinsic fluorescence excitation and emission maxima of p22 were 283 nm and 332 nm, respectively. By contrast, the intrinsic fluorescence excitation and emission maxima of rK1 were 283 nm and 229 nm, respectively. The binding of the lysine analogue trans-4-aminomethylcyclohexanecarboxylic acid (AMCHA) to p22 caused a significant increase (22%) in the intrinsic fluorescence emission spectra. Furthermore, although rK1 showed an increase in intrinsic fluorescence emission spectra of 20% upon binding to AMCHA, the emission maximum was blue shifted from 339 to 331 nm. These results establish that the kringle domain of p22 is conformationally distinct from that of rK1. Although not wishing to be bound by theory, the data suggest that amino acids of the N- or C-terminal domains of p22 interact with and modulate the structure of the kringle domain of p22.

Figure 16:
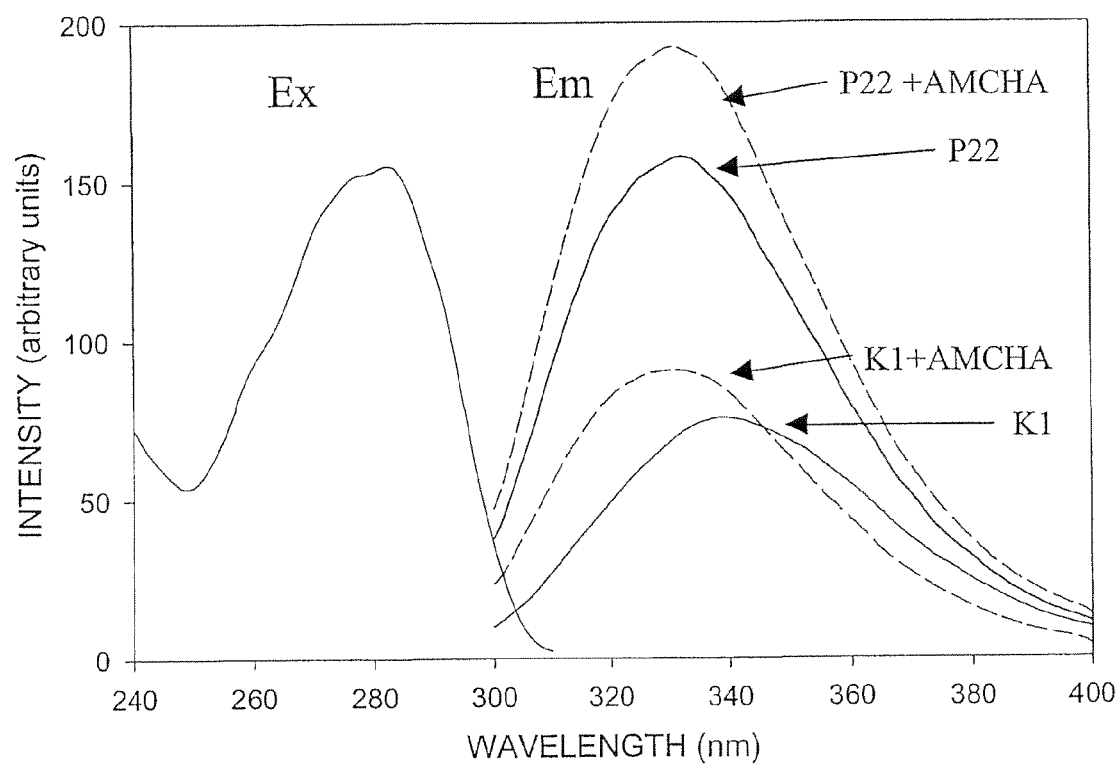
FIG. 16 illustrates the intrinsic fluorescence spectra of p22 and recombinant K1.

FIG. 16 shows the intrinsic fluorescence spectra of p22 and recombinant K1. The excitation ($E_x$) and emission spectrum ($E_m$) of ligand-free (solid line) and AMCHA (1 mM) saturated $A_{61}$ (dotted line) is presented. The spectrum was measured at 20° C. in 20 mM HEPES (pH 7.4) and 140 mM NaCl. The concentration of p22 and K1 were 25 mM and 10 mM respectively.

EXAMPLE 9

This example demonstrates the biological activity of p22.

To examine the effects of p22 on endothelial cell growth, BCE cells were grown and treated as described in Example 1, except that p22 generated by the cell-free method was used in place of $A_{61}$. It was observed that p22 inhibited the growth of BCE cells in a dose-dependent manner. The concentration of p22 required for 50% inhibition ($IC_{50}$) was 14.3+/−2.3 nM (mean+/−standard deviation, n=3), and maximum inhibition was observed at a concentration of 50 nM. The $IC_{50}$ of p22 was lower than $IC_{50}$=35 nM for $A_{61}$ and $IC_{50}$ 39.5+/−9.7 nM (mean+/−standard deviation, n=3) determined for recombinant kringle 1.

Figure 17:
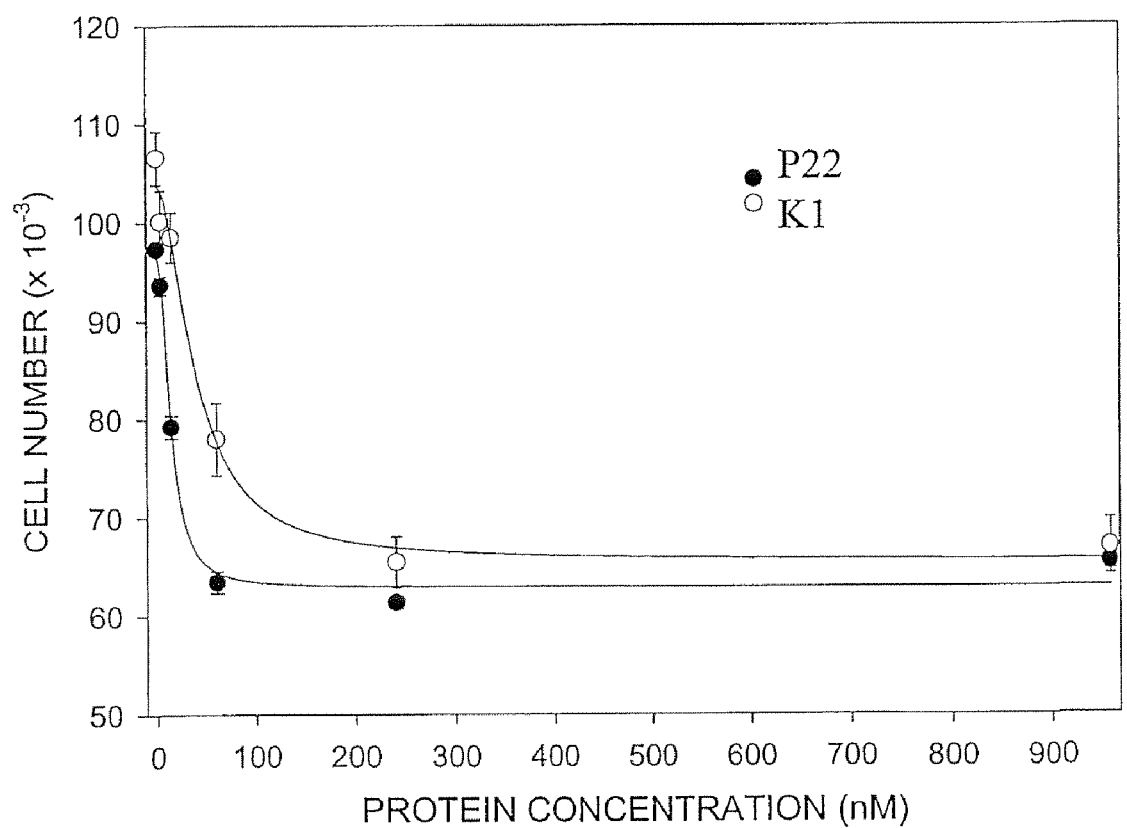
FIG. 17 illustrates the inhibition of bovine capillary endothelial cell proliferation by p22 and recombinant kringle 1.

FIG. 17 demonstrates inhibition of bovine capillary endotheil cell proliferation by p22 and recombinant kringle 1. BCE cells were incubated with various concentrations of p22 or rK1 in the presence of 1 ng/ml basic fibroblast growth factor. After 72 hour incubation, the cells were trypsinized, resuspended inIsoton II solution, and counted with a Coulter counter. The results indicate that p22 is a highly potent inhibitor of bovine capillary endothelial cell proliferation.

To determine whether p22 possess antiangiogenic activity in vivo, the effect of p22 on de novo growth of blood vessels on chick chorioallantoic membranes (CAMs) was examined. For these experiments, three-day-old fertilized white Leghorn eggs (Lillydale, Calgary, Alberta Canada) were cracked, and chick embryos with intact yolks were placed in 100×20 mm culture dishes. After 3 days of incubation in 5% $CO_2$ at 37° C., disks of methylcellulose containing phosphate-buffered saline (PBS; 137 mM NaCl, 8 mM $Na_2HPO_4$, 1.4 mM $KH_2PO_4$, 2.7 mM KCl, pH 7.4) or 5 μg of p22 (70 μl of 8.3 μM) were implanted on the CAM of embryos. After 48 hours of incubation, embryos and CAMs were analyzed for the formation of avascular zones under the stereomicroscope, and photographs were taken at 40× magnification. Compared with the PBS control, 5 μg of p22 prevented vascular growth under these conditions.

Figure 18:
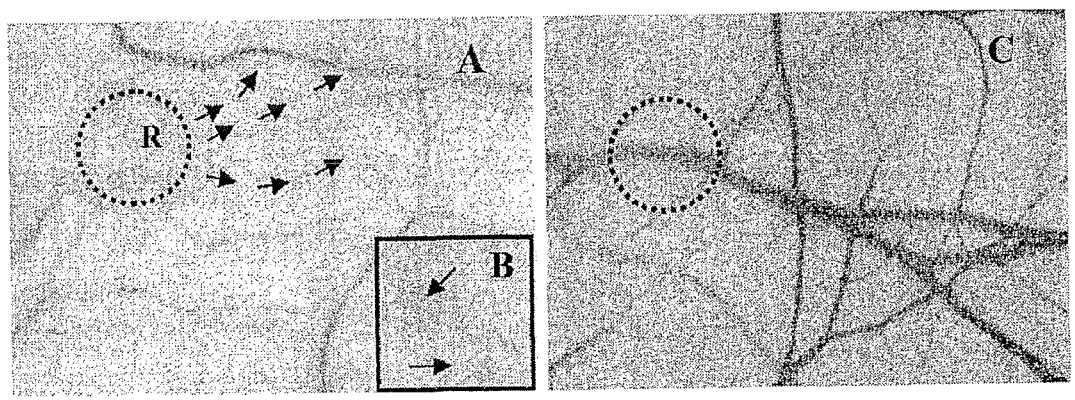
FIG. 18 illustrates the inhibition of neovascularization on the chick chorioallantoic membrane (CAM) by p22.
Figure 19A:
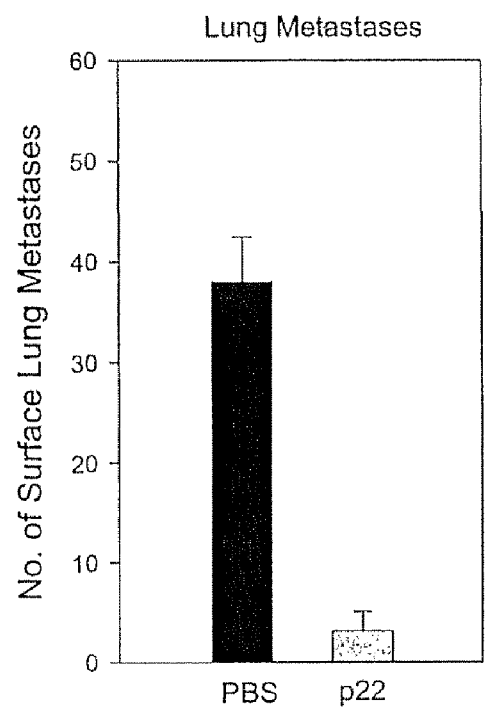
FIG. 19 illustrates the inhibition of metastatic tumor growth in mice lungs.
Figure 19B:
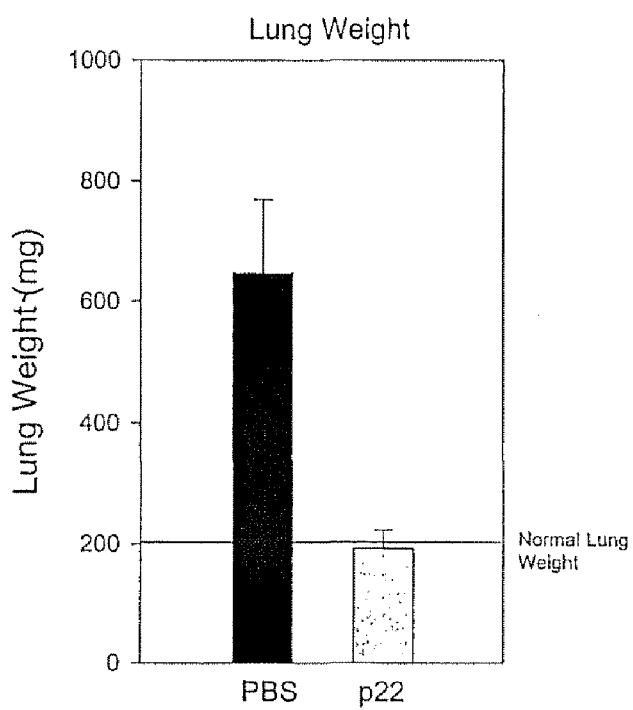
Figure 19C:
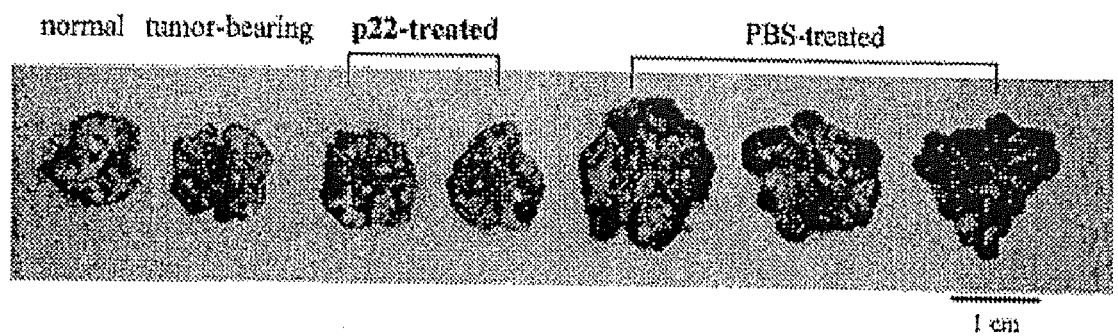

FIG. 18 shows the inhibition of neovascularization on the chick chorioallantoic membrane (CAM) by p22. Methylcellulose disks containing PBS or 5 μg of p22 were implanted on the CAM of 6-day-old chick embryos. After 48 hours, the formation of avascular zones was analyzed. The photographs are representative of 10 experiments. The dotted circles in panels A and C indicate the position of the methylcellulose disks. (A) A CAM treated with a methylcellulose disc containing p22. The area of the avascular zone is marked by arrows. (B) The high-magnification insert of the area marked by "R" in panel A shows the regressed vessels (arrows) in the adjacent area of the avascular zone. (C) A control CAM with a methylcellulose disk containing PBS. These results further indicate that p22 is has antiangiogenic activity.

Anti-tumor activity of p22 in vivo was investigated using a Lewis Lung Carcinoma assay (U.S. Pat. No. 5,776,704 to O'Reilly et al). Lewis lung carcinoma cells were grown, harvested at log phase, and resuspended in PBS. Approximately $10^6$ cells were injected subcutaneously in the middle dorsum of 6-8-week-old C57BL/6 male mice. When tumors reached 1500 $mm^3$ in size (about 14 days after implantation), the mice were randomly separated into two groups. The first group underwent surgical removal of the tumor, and the second group was subjected to a sham surgical procedure in which tumors were manipulated but were left intact. Animals from the tumor-resected group were randomly placed into test and control groups. The test group of mice received daily intraperitoneal injections of p22 in PBS (dose=2.5 mg/kg/day, i.e., 500 μl of 8.3 μM p22), whereas the control group received PBS alone. After 14 days all mice were sacrificed, the lungs were weighed, and the number of lung metastatic foci were counted.

The lungs of mice treated with PBS after tumor resection had 38+/−4 (mean+/−standard deviation, n=18) metastatic foci while mice treated with p22 had only 3+/−2 (mean+/−standard deviation, n=18) metastatic foci. The lung weight of mice with the primary tumor resected and treated with PBS increased over time and 14 days after primary tumor resection had reached 646.5+/−123 mg (mean+/−standard deviation, n=18). In contrast to the lung weight of mice treated with PBS, the average lung weight of the mice that had received daily doses of p22 only increased to 191.8+/−31 mg (mean+/−standard deviation, n=18). By comparison, the average weights of the lungs from normal mice or 14-day primary tumor bearing mice were 191+/−25 mg (mean+/−standard deviation, n=5) and 199+/−20 mg (mean+/−standard deviation, n=10), respectively. These results establish that p22 is a potent anti-metastatic agent.

FIG. 18 shows inhibition of metastatic tumor growth in mice lungs. Mice were injected intraperitoneally with PBS or p22 (in PBS) (2.5 mg/kg/day) immediately after removal of the primary tumor. p22 treatment inhibited the growth of metastatic foci (A) and blocked an increase in lung weight (B) after removal of the primary tumor. (C) Visual comparison of PBS- or p22-treated mice lungs at 14 days after resection of the primary tumor. Lungs from normal and primary tumor-bearing mice are also shown. While not wishing to be limited by theory, it is believed that the anti-metastatic activity is due to the anti-endothelial cell proliferation activity of p22, which manifests as anti-angiogenic activity in vivo.

EXAMPLE 10

This example illustrates the role annexin II tetramer plays as an extracellular receptor for plasminogen and the involvement of annexin II tetramer in the formation of plasminogen fragments.

Figure 20:
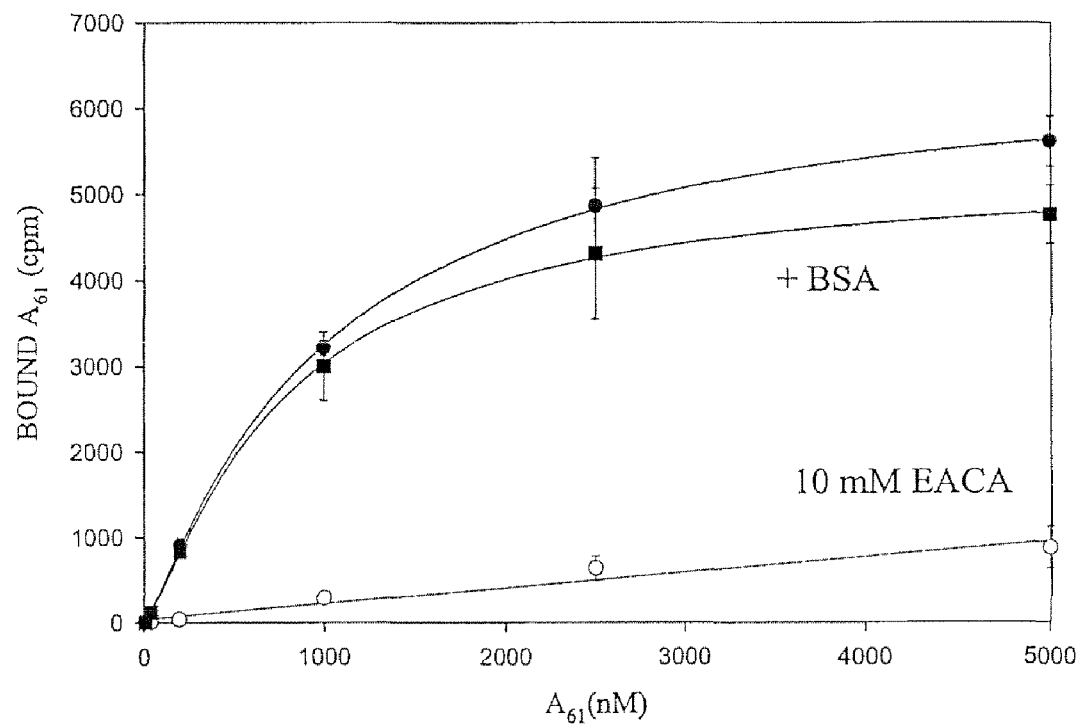
FIG. 20 illustrates the binding of $A_{61}$ to annexin II tetramer.

The $Ca^{2+}$-binding protein, annexin II tetramer is a major extracellular receptor for plasminogen. This substance regulates the conversion of plasminogen to plasmin and the autoproteolysis of plasmin (Kassam et al., *Biochemistry* 37, 16958-16966, 1998a; Kassam et al., *J. Biol. Chem.* 273:4790-4799, 1998b; Fitzpatrick et al., *Biochemistry* 39:1021-1028, 2000; Kang et al. *Trends Cardiovasc. Med.* 9:92-102, 1999). These studies have established that annexin II tetramer binds tissue plasminogen actibator, plasminogen and plasmin. We have also found that anti-angiogenic plasminogen fragment $A_{61}$ binds to annexin II tetramer (see FIG. 20). In this study, the wells of plastic plates were coated with phospholipid, incubated with annexin II tetramer and extensively washed. Various concentrations of $^{125}I\text{-}A_{61}$ were incubated with the annexin II tetramer-coated wells in the absence (filled circles) of presence of 1 mg/ml bovine serum albumin (filled squares) or 10 nM•-aminocaproic acid (open circles).

Figure 21:
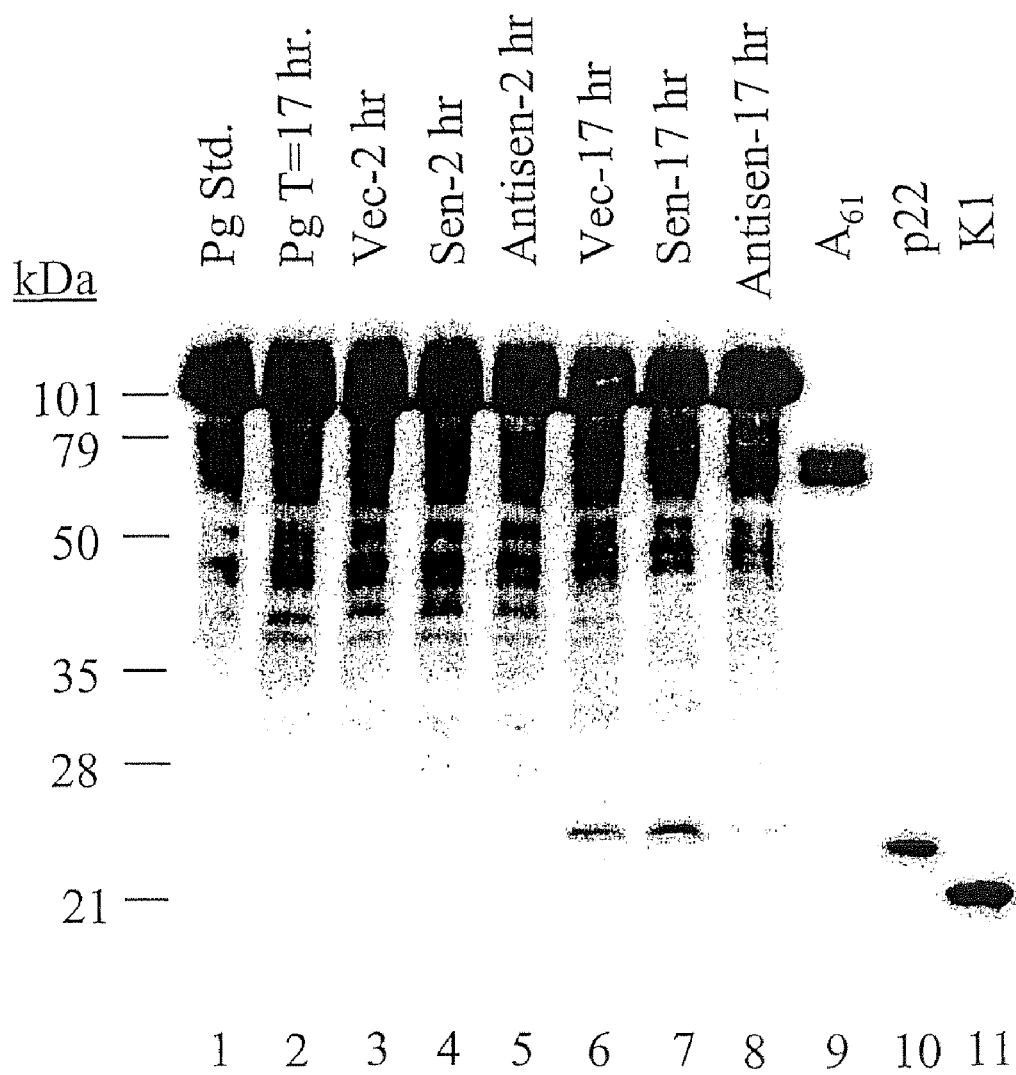
FIG. 21 illustrates the decrease in p22 and $A_{61}$ production in HeLa cells transfected with an expression vector containing antisense to p11 subunit of annexin II tetramer.
Figure 22:
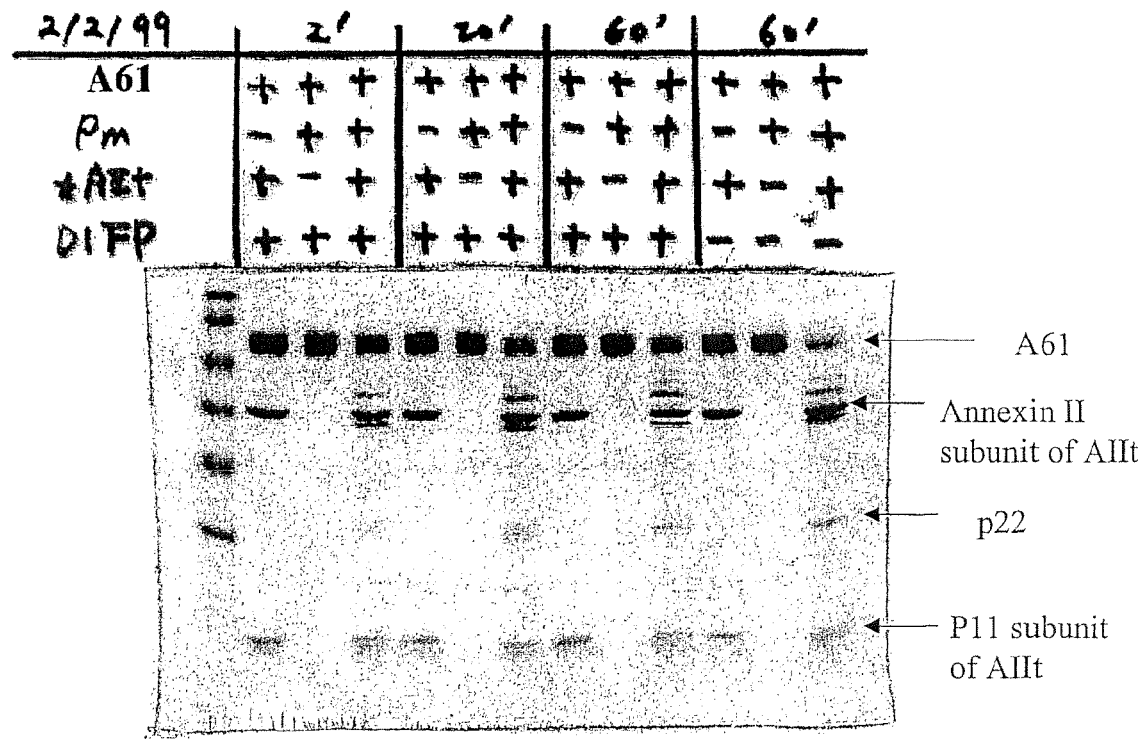
FIG. 22 demonstrates that the generation of p22 from $A_{61}$ requires plasmin and annexin II tetramer.

Since plasminogen or plasmin are the precursors for the anti-angiogenic plasminogen fragments, $A_{61}$ and p22, any agent that influences the activity of annexin II tetramer or its subunits, annexin II or p11 will affect the production or destruction of the anti-angiogenic plasminogen fragments. For example, HeLa cells in which extracellular annexin II tetramer is decreased due to transfection with an expression vector containing antisense to the p11 subunit of annexin tetramer, show diminished production of p22 (see FIG. 21). In this study, HeLa cells were transfected with an expression vector containing antisense to p11. The HeLa cells were incubated with plasminogen and after the indicated times, the plasminogen fragments were analyzed by SDS PAGE. Interestingly, when the extracellular concentration of the p11 subunit was increased by stably transfecting Hela cells with a p11 sense expression vector, the production of p22 was increased (FIG. 22). It is, therefore, believed that annexin tetramer and/or its annexin II or p11 subunits plays a key role in the efficacy of the anti-angiogenic plasminogen fragments by regulating their formation on the cell surface.

Our in vitro data also supports the conclusion that annexin tetramer participates in the production of $A_{61}$ and p22. As shown in FIG. 22, the incubation of plasmin with $A_{61}$ results in the generation of p22 only after addition of annexin tetramer. This suggests that annexin tetramer is necessary for the plasminolytic cleavage of $A_{61}$ to p22.

Since $A_{61}$ and annexin tetramer interact as shown in FIG. 22, we believe that annexin tetramer mediates the cytotoxic action of the anti-angiogenic plasminogen fragments on endothelial cells by acting as their extracellular receptors.

In view of the above, it will be seen that the several advantages of the invention are achieved and other advantageous results attained.

As various changes could be made in the above methods and compositions without departing from the scope of the invention, it is intended that all matter contained in the above description be interpreted as illustrative and not in a limiting sense.

All references cited in this specification are hereby incorporated by reference. The discussion of the references herein is intended merely to summarize the assertions made by their authors and no admission is made that any reference constitutes prior art. Applicant reserves the right to challenge the accuracy and pertinency of the cited references.

---

What is claimed is:

1. An isolated nucleic acid, wherein the nucleic acid encodes an amino acid sequence selected from the group consisting of an amino acid sequence consisting of SEQ ID NO:1, an amino acid sequence consisting of SEQ ID NO:2, and an amino acid sequence consisting of SEQ ID NO:3.

2. A vector comprising an isolated nucleic acid, wherein the nucleic acid encodes an amino acid sequence selected from the group consisting of an amino acid secquence consisting of SEQ ID NO:1, an amino acid sequence consisting of SEQ ID NO:2, and an amino acid sequence consisting of SEQ ID NO:3.

3. An isolated eukaryotic cell, the cell comprising the vector of claim 2.

* * * * *